(12) United States Patent
Gerson et al.

(10) Patent No.: US 10,718,028 B2
(45) Date of Patent: Jul. 21, 2020

(54) FLUORESCENT PROBES FOR ABASIC SITE DETECTION

(71) Applicant: CASE WESTERN RESERVE UIVERSITY, Cleveland, OH (US)

(72) Inventors: Stanton L. Gerson, Hunting Valley, OH (US); Yanming Wang, Beachwood, OH (US); Allison G. Condie, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 176 days.

(21) Appl. No.: 15/567,050

(22) PCT Filed: Apr. 14, 2016

(86) PCT No.: PCT/US2016/027541
§ 371 (c)(1),
(2) Date: Oct. 16, 2017

(87) PCT Pub. No.: WO2016/168467
PCT Pub. Date: Oct. 20, 2016

(65) Prior Publication Data
US 2018/0127830 A1 May 10, 2018

Related U.S. Application Data

(60) Provisional application No. 62/147,322, filed on Apr. 14, 2015.

(51) Int. Cl.
*C12Q 1/68* (2018.01)
*C12Q 1/6886* (2018.01)
*C12Q 1/6827* (2018.01)
*A61K 49/00* (2006.01)

(52) U.S. Cl.
CPC ........ *C12Q 1/6886* (2013.01); *A61K 49/0019* (2013.01); *A61K 49/0032* (2013.01); *A61K 49/0039* (2013.01); *C12Q 1/6827* (2013.01); *C12Q 2600/136* (2013.01)

(58) Field of Classification Search
CPC .................................................... C12Q 1/6886
USPC .......................................................... 435/6.11
See application file for complete search history.

(56) References Cited

U.S. PATENT DOCUMENTS 4,465,691 A 8/1984 Bisagni et al.
2009/0298077 A1* 12/2009 Xu ........................ C12Q 1/6827
435/6.16

FOREIGN PATENT DOCUMENTS

WO 00039345 A1 7/2000
WO 2008/066990 A2 6/2008
WO 2015/151071 A2 10/2015

OTHER PUBLICATIONS

Boturyn, Didier, et al., "Synthesis of Fluorescent Probes for the Detection of Absaic Sites in DNA", Tetrahedron, vol. 53, No. 15, pp. 5485-2492, 1997.
Carnelly, Trevor J., et al. "Synthesis, Characterization, and Applications of a Fluorescent Probe of DNA Damage", Chem. Res. Toxicol. 2001, 14, 1513-1522.
Condie, Allison G., et al., "Development of Molecular Probes for Biomedical Imaging of Cancer and Neurological Disease", Department of Chemistry Thesis, Aug. 2015.
Condie, Allison G., et al., "A Fluorescent Probe to Measure DNA Damage and Repair", Plus One, DOI:10:1371, Aug. 26, 2015.

\* cited by examiner

*Primary Examiner* — Jezia Riley
(74) *Attorney, Agent, or Firm* — Tarolli, Sundheim, Covell & Tummino LLP

(57) ABSTRACT

A fluorescent probe for binding to and detection of AP sites of DNA includes the following formula: F-L-X where F is a fluorescent moiety, X is an aminooxy group ($-ONH_2$), and L is a linker that links or couples the fluorescent moiety to the oxyamine.

12 Claims, 12 Drawing Sheets

Specification includes a Sequence Listing.

Fig. 2A-B

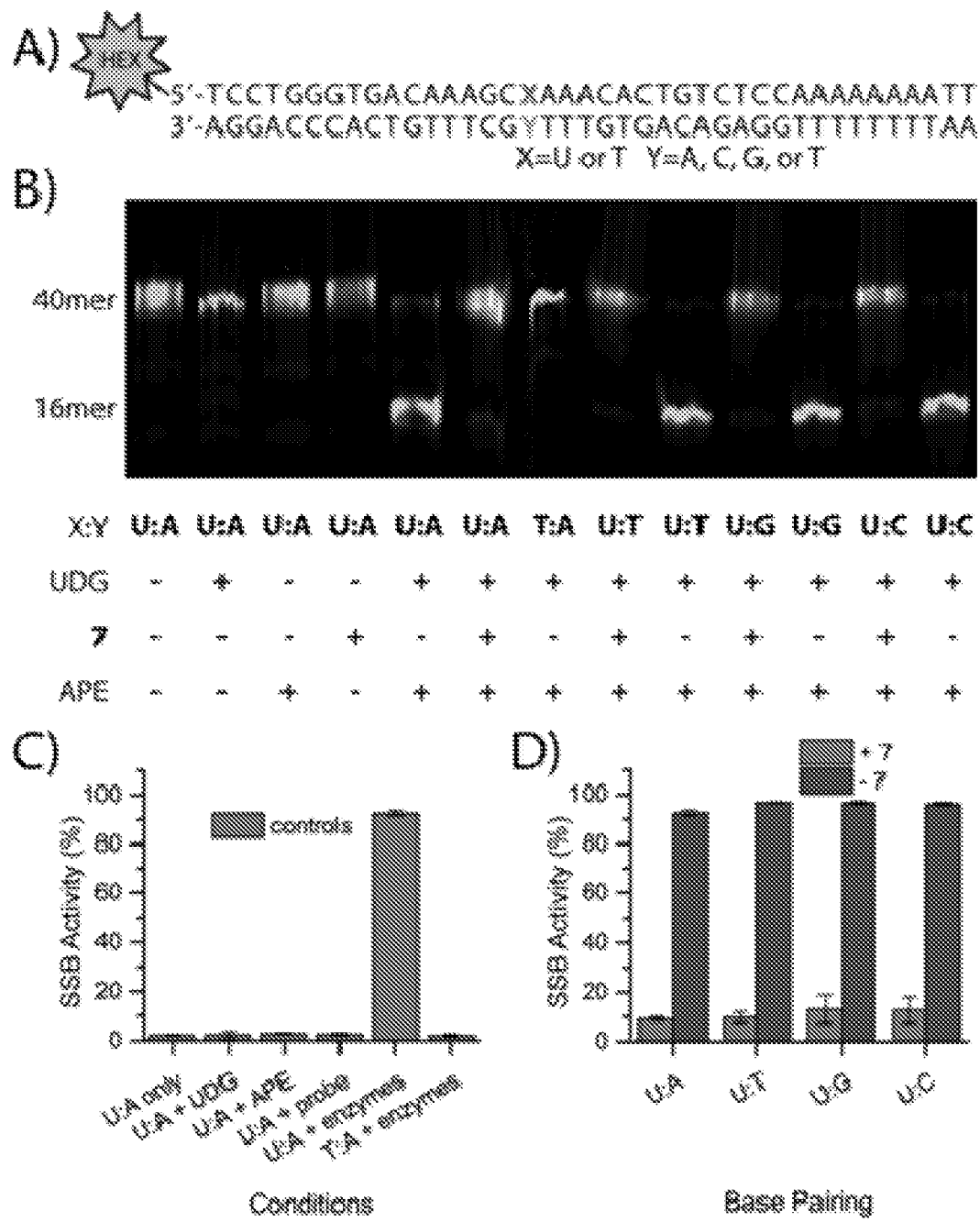
Figs. 5A-D

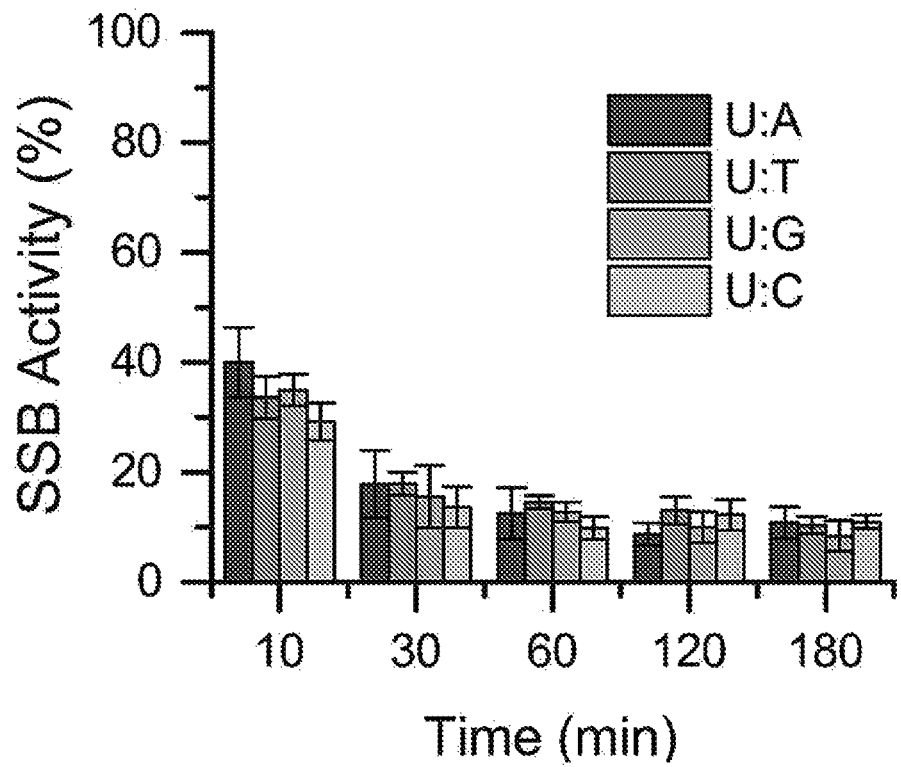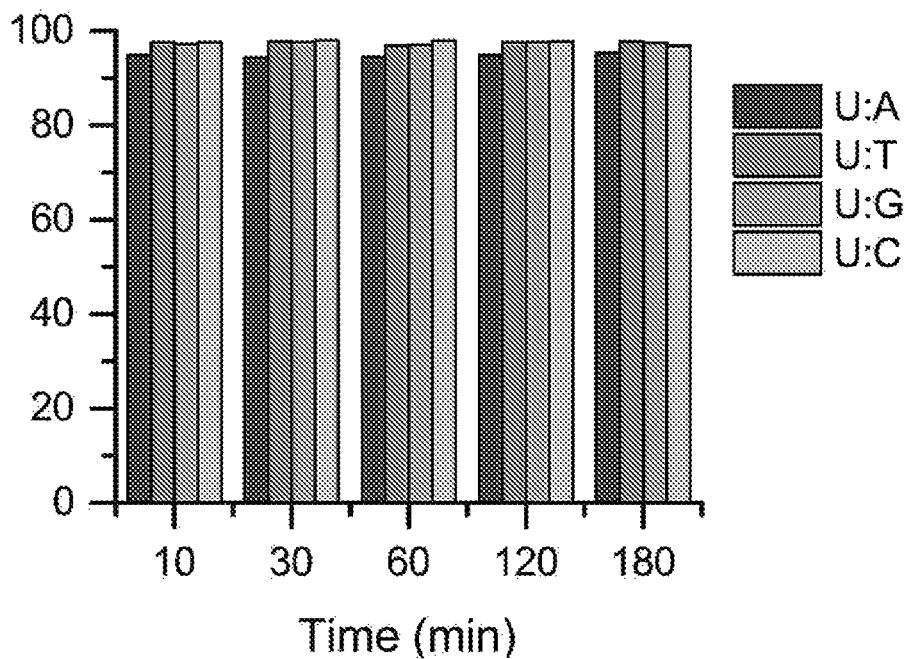
Figs. 6A-B

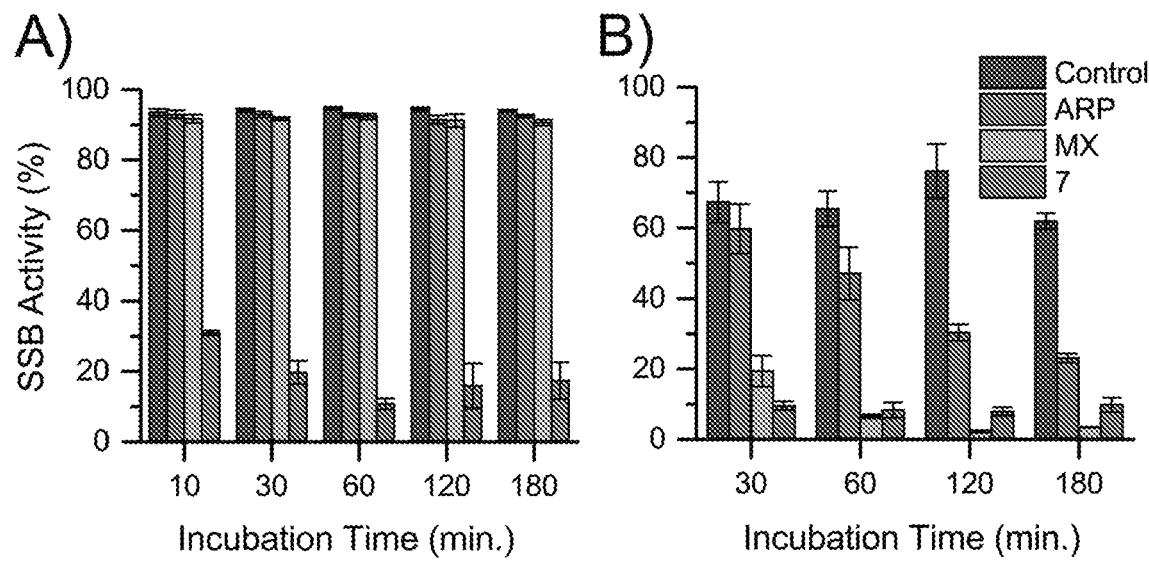
Figs. 9A-B
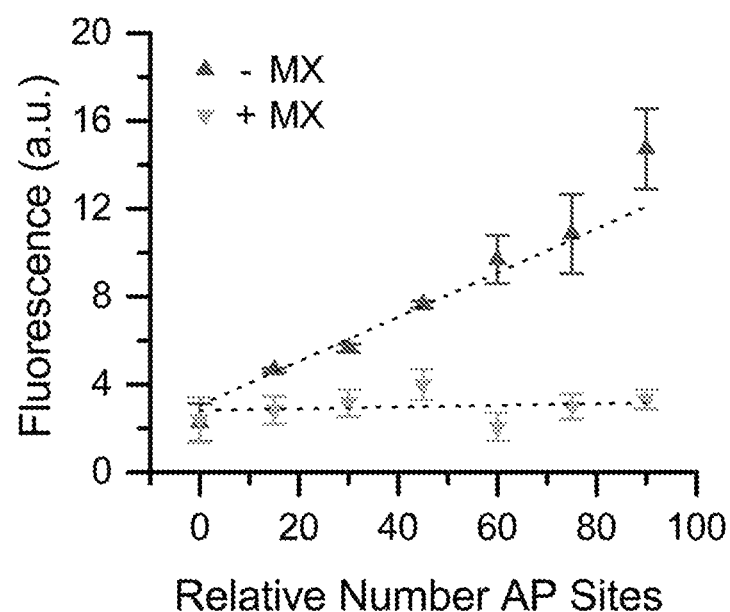
Fig. 10

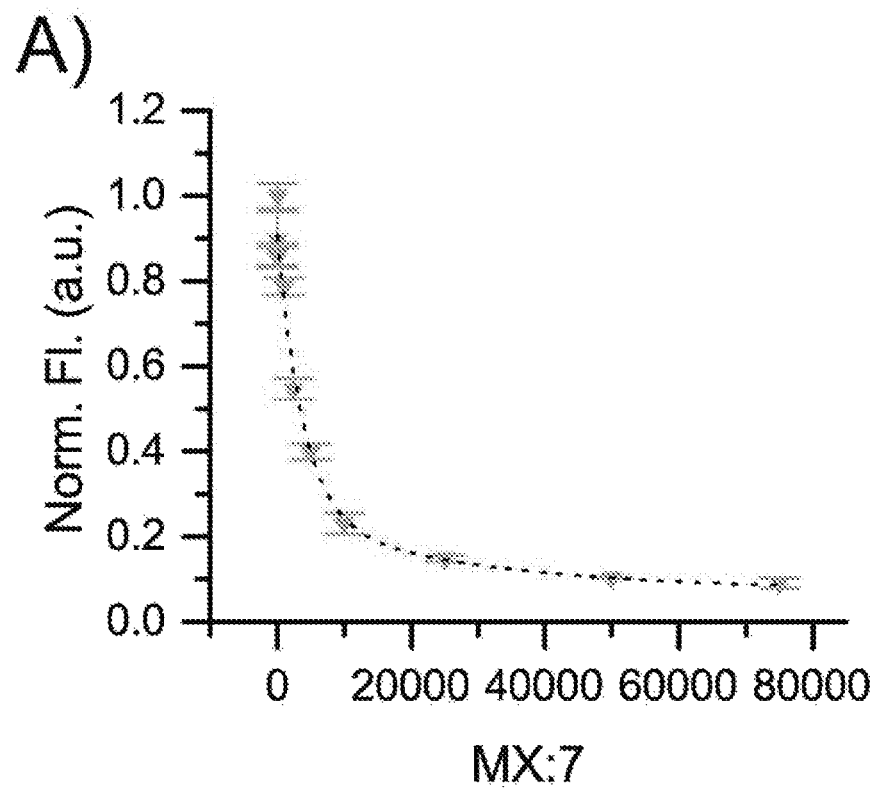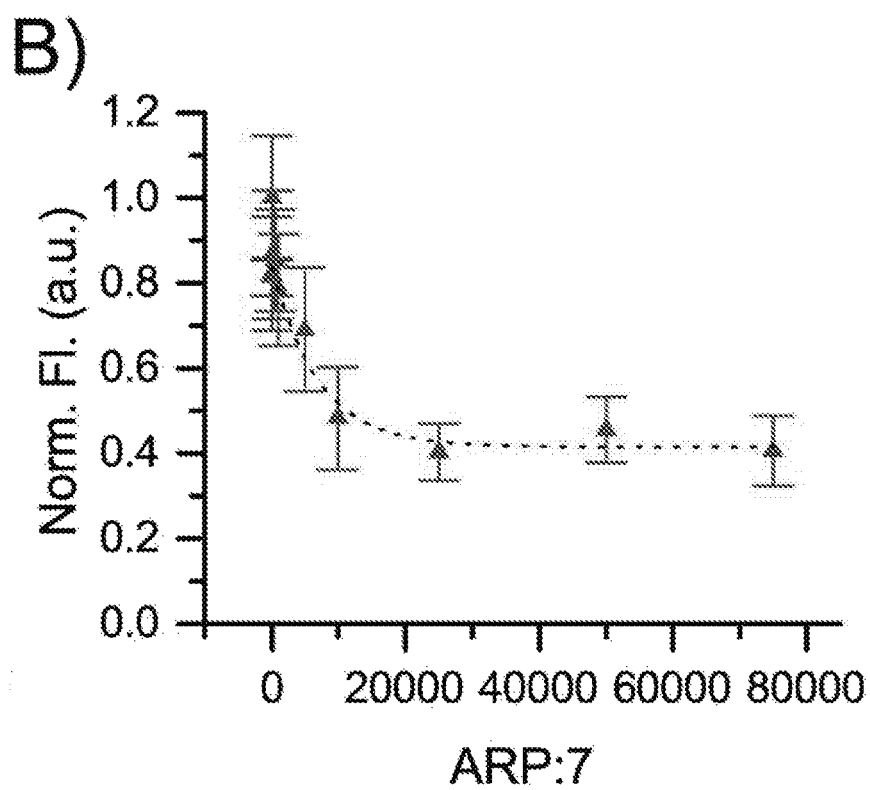
Figs. 13A-B

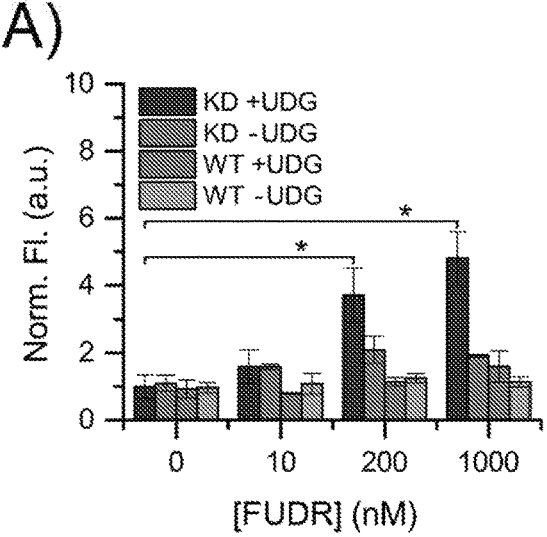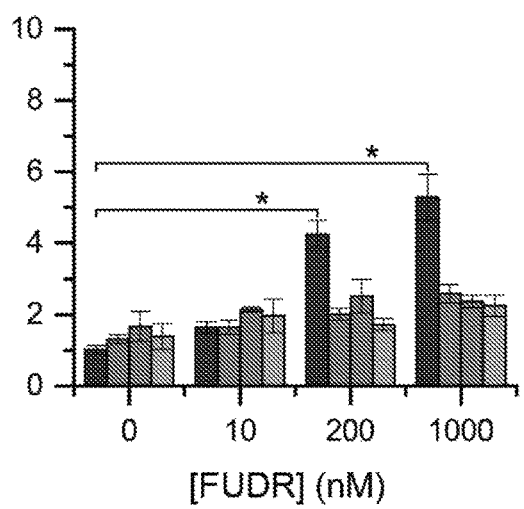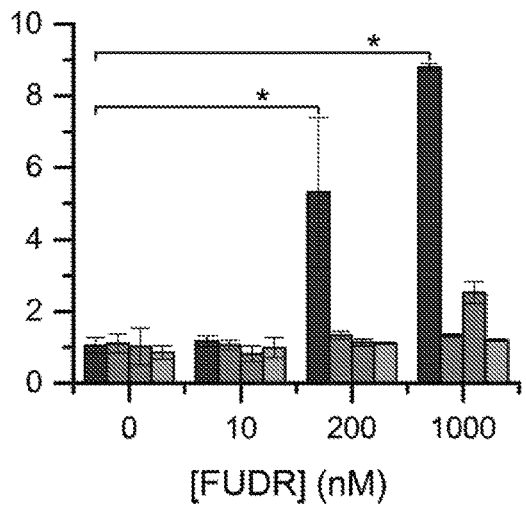
Figs. 14A-C

FLUORESCENT PROBES FOR ABASIC SITE DETECTION

RELATED APPLICATION

This application claims priority from U.S. Provisional Application 62/147,322, filed Apr. 14, 2015, the subject matter of which is incorporated herein by reference in their entirety.

GOVERNMENT FUNDING

This invention was made with government support under Grant Nos. CA043703 and CA148052 awarded by The National Institutes of Health. The United States government has certain rights in the invention.

TECHNICAL FIELD

This application relates to fluorescent probes for detection and/or measurement of genomic apurinic/apyrimidinic (AP) sites, and to methods and systems of detecting and quantifying AP site formation in DNA.

BACKGROUND

As cancer continues to be a public health concern, efforts are being directed toward the development of new chemotherapies. Many chemotherapeutic agents induce DNA damage ultimately leading to cell death. Under normal physiological conditions, multiple pathways exist for the repair of damaged DNA. However, such pathways can subvert the effects of chemotherapy targeting DNA in cancer cells and trigger drug resistance. These repair pathways include homologous recombination, non-homologous end joining, nucleotide excision repair, mismatch repair, and base excision repair (BER). While all these pathways repair DNA damage, the types of damage they repair vary, with BER being particularly relevant to exogenous chemical damage such as that caused by chemotherapy.

Damage to DNA can result from direct chemical modification of nucleotides or from accumulation of aberrant bases, such as uracil. Regardless of the type of damage, the first step in the BER pathway is the excision of the damaged base by a glycosylase, which leaves the free ribose sugar termed abasic or AP (apurinic/apyrimidinic) site. For example, uracil DNA glycosylase (UDG) rapidly excises uracil from DNA to initiate the repair sequence (FIG. 3). AP sites are the most common lesions in DNA, and if left unrepaired, can be mutagenic. AP sites are formed following oxidative damage of DNA by reactive oxygen species (ROS) and this oxidative damage is associated with cancer, heart disease, Parkinson disease, and aging. Therefore, tools that detect and quantify AP sites are of broad interest to the medical and scientific communities.

Several research groups have developed tools to detect AP sites based on methods including fluorescence, nanopore ion detection, mass spectrometry, atomic force microscopy, electrochemistry, and electron paramagnetic resonance. Some of these techniques employ a variety of molecular probes targeted to the AP site through various chemical features of the lesions. Several probes containing an aminooxy moiety have been developed that covalently bind to the AP site aldehyde and form an oxime ether. Among them, aldehyde reactive probe (ARP), based on biotin tethered to an alkoxyamine, detects AP sites in a colorimetric streptavidin-horseradish peroxidase in vitro assay.

Previously developed aldehyde-reactive probe (ARP) and similar compounds that fluoresce in the UV-visible range are commonly used for in vitro detection and quantification of AP sites. Such assays have several drawbacks in studying DNA-targeted chemotherapies: 1) they are often limited to the study of AP sites in DNA of circulating cells in plasma induced by chemotherapeutic agents, which is only an indirect measure of AP site formation; 2) for direct detection and quantification of AP sites in tumor regions, dissection and homogenization of tumor tissues are required at each time point after therapeutic treatments, which make longitudinal studies impossible; 3) these assays are not readily repeatable due to sophisticated procedures.

SUMMARY

Embodiments described herein relate to fluorescent probes for detection and/or measurement of genomic apurinic/apyrimidinic (AP) sites, and to methods and systems of detecting and quantifying AP site formation in DNA. The fluorescent probes for binding to and detection of AP sites can have the following formula:

F-L-X where F is a fluorescent moiety, X is an aminooxy group (—ONH$_2$), and L is a linker that links or couples the fluorescent moiety to the aminooxy group.

In some embodiments, the fluorescent moiety can be a cyanine fluorophore or dye, coumarin fluorophore or dye, or dansyl fluorophore or dye. In other embodiments, the fluorescent moiety can be a cyanine fluorophore, such as Cy3, Cy5, Cy5.5, Cy7, Cy7.5, ZW800-1, and CW-800.

In other embodiments, the fluorescent probe can be selected from the group consisting of:

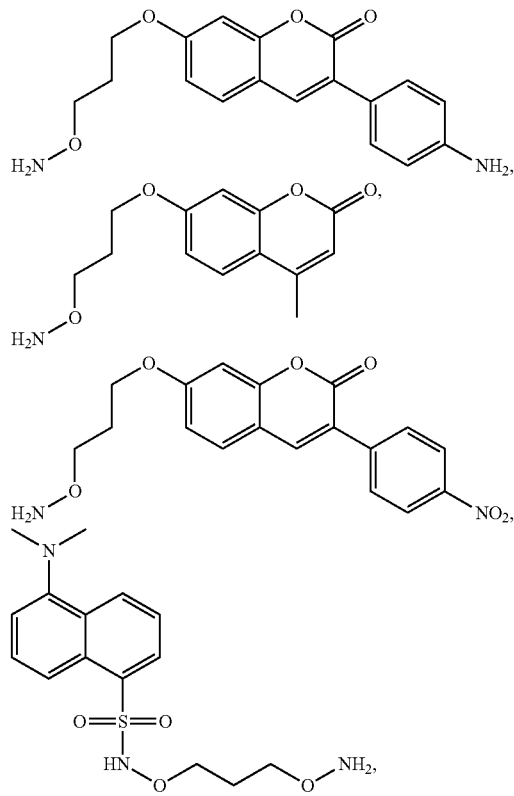

-continued

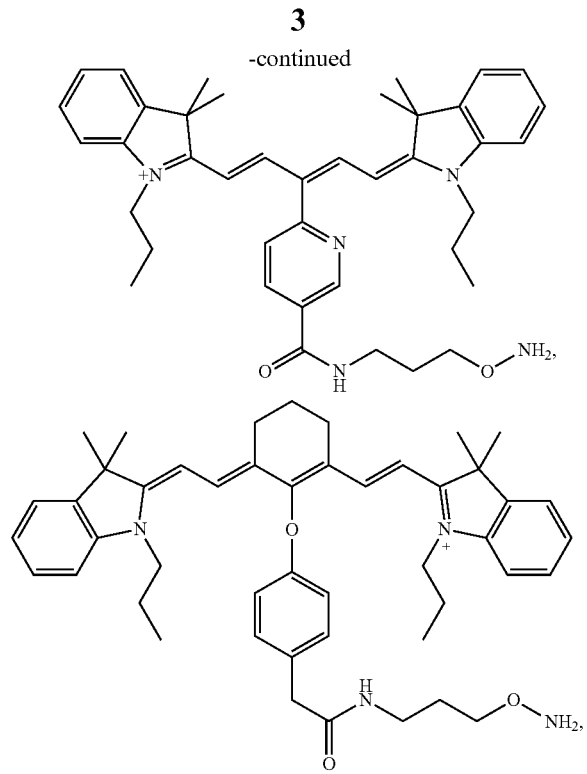

and pharmaceutically acceptable salts thereof.

In some embodiments, the DNA can be extracted from the subject's cells before contacting the DNA with the fluorescent probe. The number of AP sites in the sample of DNA can be correlated to the number of AP sites in a control DNA specimen. The control DNA specimen can comprise individual AP-DNA standards having known concentrations of AP sites. The number of AP sites of sample DNA and the control DNA specimen can be determined substantially simultaneously. Unbound fluorescent probe can be removed from the sample of DNA after contacting the DNA with the fluorescent probe.

Other embodiments relate to a method of quantitating AP sites in DNA of a biological sample obtained from a subject. The method includes isolating a sample of DNA. The isolated sample of DNA is contacted with the fluorescent probe. Unbound fluorescent is then removed from the isolated DNA sample. The number of AP sites in the sample of DNA is quantitatively assessed.

In some embodiments, the fluorescence intensity of the sample of DNA can be correlated to the concentration of AP sites in the sample of DNA by comparing the fluorescence intensity in the sample of DNA to the fluorescence intensity of at least one control DNA specimen. The control DNA specimen can comprise an individual AP-DNA standard having a known concentration of AP sites.

Other embodiments, relate to a method of screening therapeutic agents for inhibiting base excision repair (BER). The method includes contacting a sample of AP-DNA with the fluorescent probe and one or more therapeutic agents. Unbound fluorescent probe and the one or more therapeutic agents is then removed from the sample of AP-DNA. The fluorescent probe labeled AP sites in the sample of AP-DNA are subsequently detected. The level or number of fluorescent probe labeled AP sites in the sample of AP-DNA are then correlated to or compared with a sample of AP DNA contacted with the fluorescent probe in the absence of the therapeutic agent. A reduced level of fluorescent probe labeled AP sites in the sample of AP-DNA compared to the sample of AP-DNA not containing the therapeutic agent is indicative of an effective therapeutic agent or an effective combination of therapeutic agents.

In some embodiments, the therapeutic agent can include a DNA repair inhibitor. The DNA repair inhibitor can include a base excision repair inhibitor. The base excision repair inhibitor can include an AP endonuclease inhibitor. The therapeutic agent can also include a compound capable of forming a covalent linkage with an aldehyde group on AP-DNA.

Other embodiments relate to a method of measuring the efficacy of an anticancer agent in generating abasic (AP) sites in DNA of cancer cells of a subject. The method includes administering to the subject an anticancer agent that generates AP sites in at least one cancer cell. The fluorescent probe can then be administered to DNA of cancer cells to which the anticancer agent was previously administered. The amount of probe bound to AP sites of DNA of cancer cells of the subject is then measured. The amount of probe bound to cancer cells of the subject is indicative of the efficacy of the anticancer agent in generating AP sites in cancer cells of the subject.

BRIEF DESCRIPTION OF THE DRAWINGS

FIGS. 5(A-D) illustrate a summary of SSB activity assay. (A) 5'-HEX labeled dsDNA 40mer used for fluorescence-based cutting assay; (B) SSB assay visualized by denaturing gel electrophoresis to separate intact 40mer from 16mer. (C) Analysis of the gel electrophoresis controls with SSB activity %=(F1 16mer)/(F1 16mer+F1 40mer)×100. (D) Analysis of gel electrophoresis with Cy7MX or vehicle control.

FIGS. 6(A-B) illustrate the evaluation of base pairing on SSB activity. Time course represents incubation time of U:X DNA before APE addition with UDG and (A) compound Cy7MX or (B) with vehicle control.

The baseline reduction in cutting is due to competition of APE and Cy7MX for the AP-DNA substrate.

Figure 8:
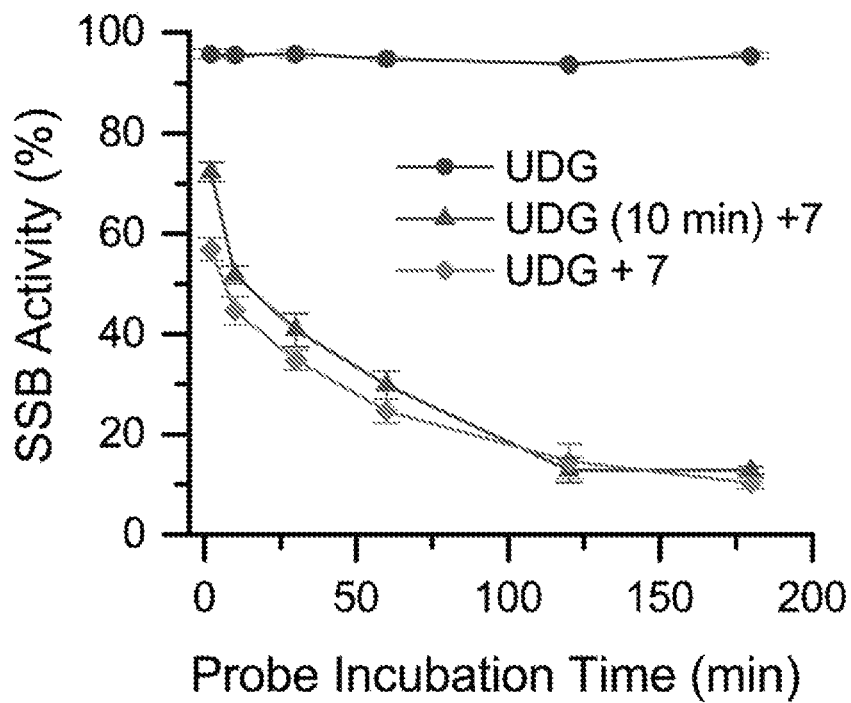

FIG. 8 illustrates the evaluation of UDG inhibition by Cy7MX. Time course represents incubation time of U:A DNA before APE addition with UDG alone, 10 minutes UDG pretreatment then Cy7MX, and UDG and Cy7MX without pretreatment.

FIGS. 9(A-B) illustrate SSB activity assay comparison of ARP, MX, and Cy7MX. (A) ARP (1 nmol), MX (1 nmol), and Cy7MX (1 nmol) with UDG (5 units) and U:A DNA (5 pmol) as a function of incubation time prior to APE (10 units) addition. (B) ARP (200 nmol), MX (200 nmol), and Cy7MX (2 nmol) with UDG (5 units) and U:A DNA (5 pmol) as a function of incubation time prior to APE (1 unit) addition.

FIG. 10 illustrates fluorescence response and MX blocking of Cy7MX. Calf thymus DNA treated with heat and acid for increments of 15 min to give a linear relative number of AP sites. AP DNA was then pretreated with MX (50 mM, +MX) or NaCl (50 mM, −MX) followed by incubation with Cy7MX (0.05 mM). Fluorescence measures show a linear response to Cy7MX when not blocked by MX.

Figure 11:
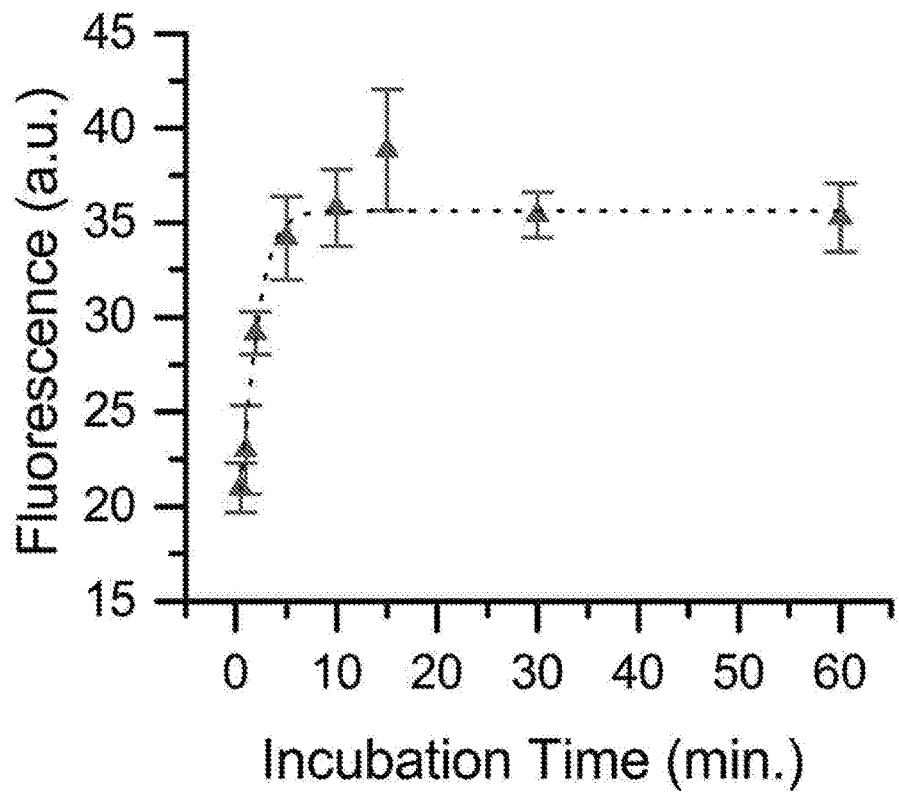

FIG. 11 illustrates time course of Cy7MX binding to calf thymus AP DNA.

Figure 12:
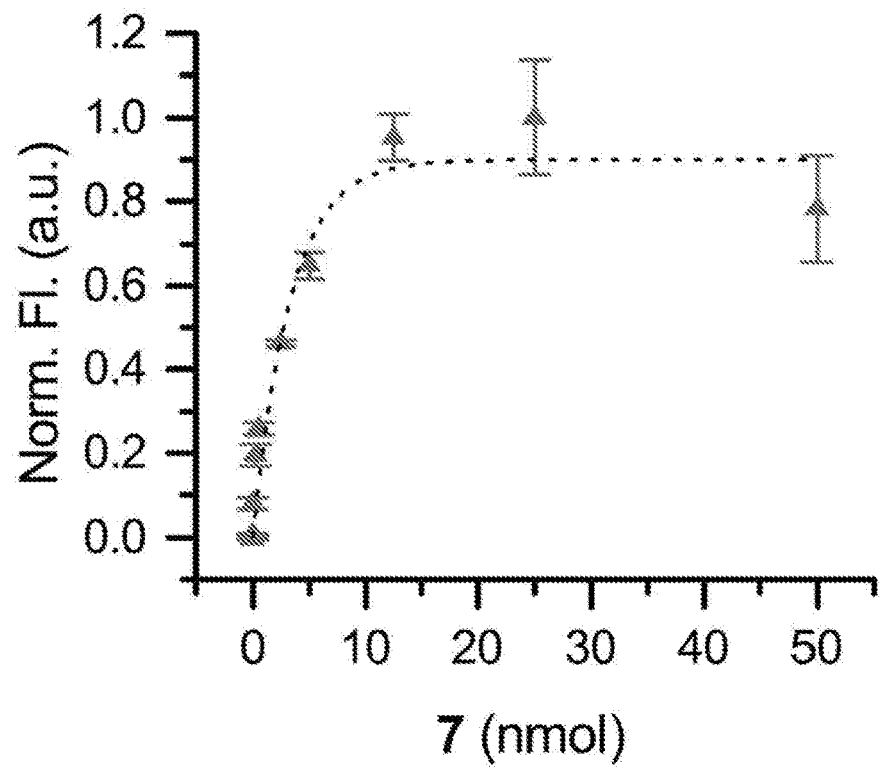

FIG. 12 illustrates the dose-response of Cy7MX in calf thymus AP DNA.

FIGS. 13(A-B) illustrate competition studies between Cy7MX and MX or ARP in genomic DNA. (A) MX or (B) ARP for AP sites in calf thymus DNA treated with heat and acid for 45 min are shown. The molar ratio of probe to Cy7MX was increased by increasing [probe] and maintaining a constant. ED50 values were calculated from the fittings to be 2600-fold excess for ARP and 3000-fold excess for MX.

FIGS. 14(A-C) illustrate the detection of AP sites in DNA isolated from FUDR treated DLD1 cells. DNA extracted from UDG knockdown (KD) and control (WT) cells after (A) 24 h, (B) 48 h, and (C) 72 h of continuous FUDR exposure. Purified DNA was treated in vitro with UDG (+UDG) or vehicle control (−UDG). * Indicates significance ($p<0.001$) using a one-way ANOVA test.

Figure 15:
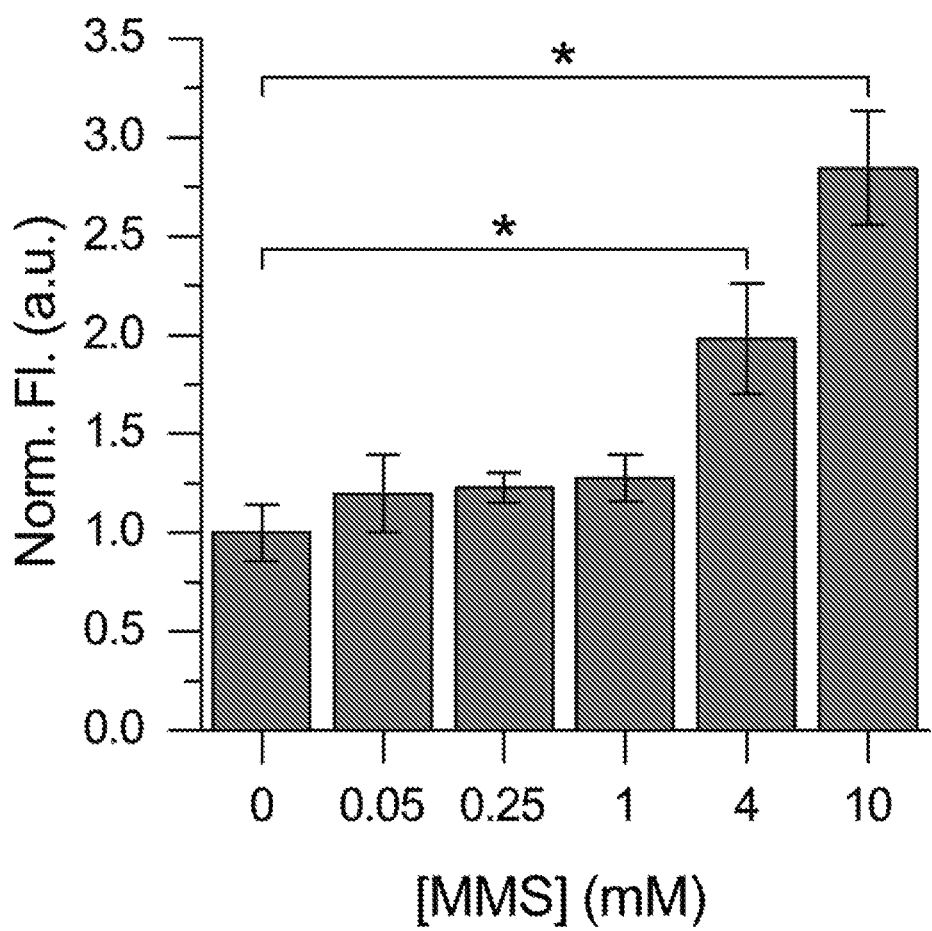

FIG. 15 illustrates the detection of AP sites in DNA isolated from MMS treated DLD1 cells. DNA extracted from DLD1 WT cells after 3 h of continuous MMS exposure. Purified DNA was treated with Cy7MX without enzyme pretreatment. * Indicates significance ($p<0.001$) using a one-way ANOVA test.

DETAILED DESCRIPTION

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

In the context of the application, the term "sample" can refer to a specimen or culture obtained from any source, as well as clinical, research, biological and environmental samples. Biological samples may be obtained from animals (including humans) and encompass cells, fluids, solids, tissues, and organs, and whole organisms.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprins, equines, or canines felines, ayes, etc.).

As used herein, the terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma.

Embodiments described herein relate to fluorescent probes that bind to an abasic (apurinic/apyrimidinic) (AP) site of DNA (or fluorescent AP site binding probes) and to the use of the fluorescent probes in direct imaging and quantifying the generation of AP sites in DNA and assessing DNA damage and repair. Direct imaging and quantitative assessment of AP sites in DNA can be used for efficacy evaluation of DNA-targeted chemotherapies and/or anticancer agents that produce AP sites and invoke base excision repair (BER). Understanding the dynamic of AP site formation and repair can allow clinicians and researchers to determine optimal dose strategies of single and combination chemotherapeutic treatment schedules. Furthermore, with the advent of agents to block BER, direct imaging of AP sites in DNA can be used to determine the optimal dose schedule to potentiate drug administration based on persistence of AP sites. For instance, if one agent induces AP sites, and another blocks BER repair, while a third induces Topo II, understanding the relationship between these events can impact therapeutic efficacy. In addition, direct imaging of AP sites can facilitate screening of new agents that are designed to either induce AP sites in tumor or cancer cells or block AP sites from DNA repair.

The fluorescent probes described herein can have following formula:

F-L-X where F is a fluorescent moiety, X is an aminooxy group (—ONH$_2$), and L is a linker that links or couples the fluorescent moiety to the aminooxy group.

The fluorescent moiety can include any fluorescent molecule the upon exposure or excitement by light of specific wavelength is capable of fluorescing. In some embodiments, the fluorescent moiety allows the probe to be detectable upon in vivo, in vitro, or ex vivo administration to DNA or cells containing DNA and particularly allows AP sites of DNA of cells to be optically imaged in vivo, in vitro, or ex vivo. Examples of fluorescent moieties include fluorophores, such as, fluorescent lanthanide complexes, including those of Europium and Terbium, fluorescein, fluorescein isothiocyanate, dichlorotriazinylamine fluorescein, rhodamine, tetramethylrhodamine, umbelliferone, eosin, erythrosin, coumarin, methyl-coumarins, pyrene, Malacite green, Cy3, Cy5, Cy5.5, Cy7, Cy7.5, ZW800-1 (i.e., N-hydroxysuccinimide (NHS) ester), CW-800, stilbene, *Lucifer* Yellow, Cascade Blue, Texas Red, alexa dyes, dansyl chloride, phycoerythin, luciferin, green fluorescent protein and its wavelength shifted variants, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066.

In some embodiments, the fluorescent moiety can include a light emitting red fluorescence or near infrared fluorescence (NIRF) moiety, such as cyanine fluorophores or dyes, (e.g., Cy5, Cy5.5, Cy7, Cy7.5, ZW800-1, and CW-800), that can be linked to the aminooxy moiety with the linker. Red and near infrared fluorescence moieties are more readily excited and detected in tissue and have less nonspecific absorption than UV or visible fluorescent moieties or dyes. Biological tissues possess "near infrared window" of transparency above 700 nm (actual value depends on tissue type). This allows for in-depth imaging of organisms in real-time, non-destructive fashion. Labeling of AP sites of DNA with a fluorescent probe that includes a near infrared fluorescent moiety makes it possible to track it, and study distribution of the fluorescent probe when administered to the subject.

The linker that links or couples the fluorescent moiety to the aminooxy group can include any linker, chemical, and/or or biological moiety. In some embodiments, the linker can enhance solubility of the fluorescent probe in an aqueous media and enhances the binding affinity of the fluorescent probe to AP sites of the DNA. The linker can be of any suitable length and contain any suitable number of atoms and/or subunits. In one example, the linker can be selected from the group consisting of $C_1$-$C_2$4 alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), and combinations thereof.

In some embodiments, the linker can be about 3 to about 15 atoms in length and include an alkyl end (e.g., methyl, ethyl, propyl, butyl) that that is covalently bonded to the aminooxy group.

In some embodiments, the fluorescent probe that binds to AP sites for imaging and/or detecting AP sites in DNA can be selected from the group consisting of

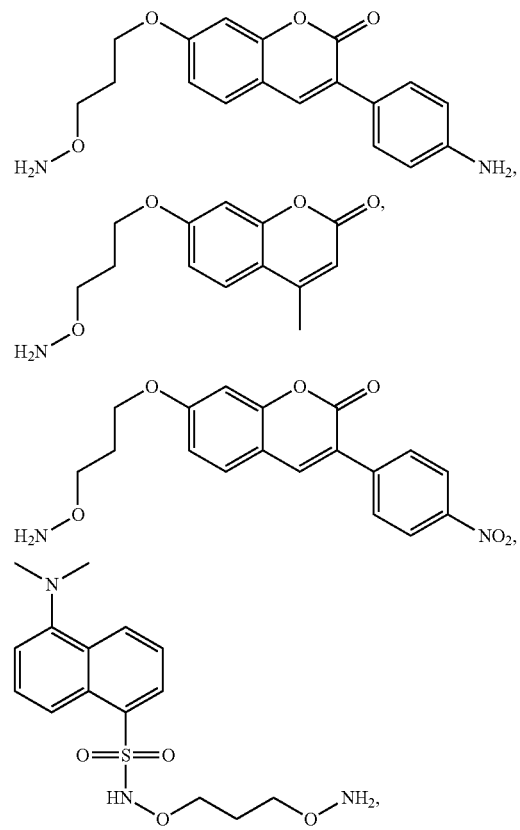

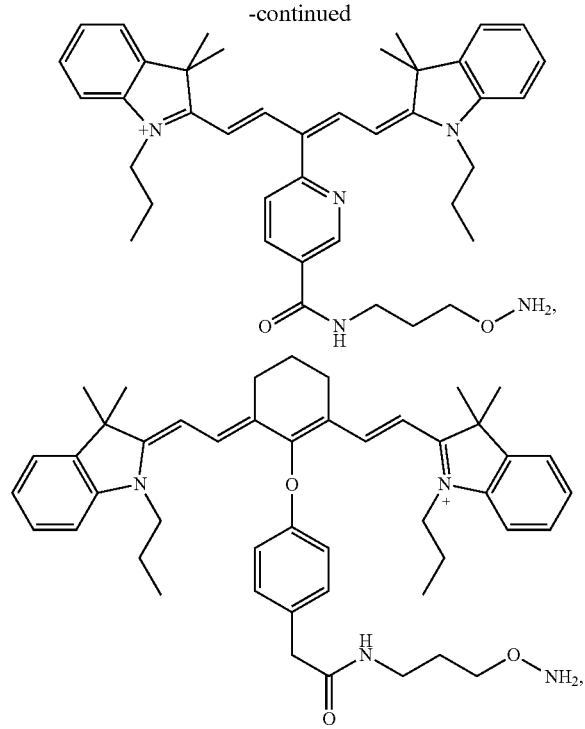

and pharmaceutically acceptable salts thereof.

The fluorescent probes described herein when administered to DNA of subject can readily react with or covalently bind to an aldehyde of an AP site generated, for example, by an anticancer agent, and form an oxime ether. In some embodiments, the fluorescent probe once covalently bound to the AP site can prevent AP endonuclease cleavage of phosphodiester bonds of the AP site. Advantageously, the fluorescent probes described herein can react with an aldehyde of the AP site at a rate faster than the AP endonuclease can cleave phosphodiester bonds of the AP site.

By way of example, a sample of DNA can be isolated from a biological sample, such as a biological sample obtained from a subject under examination and/or a subject treated with a DNA damaging agent, such as an anti-neoplastic agent and/or anti-mitotic agent. The biological sample obtained from the subject can include blood, tissue, as well individual cells. In one example, the sample of DNA can be isolated from peripheral blood mononuclear cells obtained from a subject.

The DNA sample can be isolated from the biological sample using conventional DNA isolation and purification methods. Conventional approaches to DNA isolation and purification are based on multi-step procedures involving phenol/chloroform (see for example Sambrook. J. et al, Molecular Cloning: A Laboratory Manual, $2^{ND}$ Edition, Cold Spring Harbor Laboratory Press, 1989). An example of a commonly used method for isolating DNA from a DNA source, e.g., blood, saliva, tissue samples, etc., involves lysing the DNA source with a combination of a proteolytic enzyme and a detergent followed by extracting the mixture with an organic solvent, e.g., phenol and chloroform, so that the DNA enters the aqueous phase and the hydrolyzed products enter the organic phase. The DNA in the aqueous phase is then precipitated by the addition of alcohol.

In another approach, DNA can be isolated by lysing the DNA source with a chaotropic substance, for example guanidinium salt, urea and sodium iodide, in the presence of a DNA binding solid phase. The released DNA is bound to the solid phase in a one step reaction, where the beads are washed to remove any residual contaminants. Although these methods have proven to be less time consuming and toxic, they have resulted in a moderate level of DNA shearing and some level of contamination. In a further approach, a sample of DNA can be isolated from a starting source by mixing the starting source with a cationic detergent, which forms a hydrophobic complex between the DNA and detergent. The hydrophobic complex is separated from the solubilized contaminants and the DNA recovered by addition of a salt.

Following isolation of the DNA from the biological sample, the isolated DNA sample can be contacted with the fluorescent probes described herein that bind to AP sites of the DNA. The fluorescent probes can be provided in a buffer, such as a phosphate buffer, to provide an AP detection reagent. In one example, about 5 μM of the fluorescent probe can be included in about 100 μL of a phosphate buffer (10 mM, pH 7.0). An excess amount of the AP detection reagent can be contacted with a sample of DNA taken from a subject in order to assure that each available AP-site comes in contact with the AP detection reagent.

Following contact of the DNA sample with the AP detection reagent, excess fluorescent probe can be removed from the sample to avoid background fluoresence. The excess fluorescent probe can be removed by washing the sample without detaching the DNA bound fluorescent probe. For example, an about 70% ethanol solution can be added to the sample, removed, and then discarded. The sample may be washed one or more times in order to assure removal of unbound fluorescent probe.

Following removal of the excess fluorescent probe, the fluorescent probe labeled AP sites of the DNA sample can be detected and quantitated. The fluorescent probe labeled AP sites can be quantitatively detected fluorometrically or through other types of electromagnetic spectroscopy, which analyze fluorescence from the sample. Devices that measure fluorescence are commonly referred to as fluorometers, fluorimeters, or fluorescence spectrophotometers.

The measured fluorescence can be compared with the fluorescence of standard control specimens of known AP-DNA concentrations to quantitate or determine the number of AP sites in the DNA sample. Blank AP-DNA background readings from the control DNA can also be used to quantitatively determine the number of AP sites of the DNA sample. In some embodiments, the concentration of AP sites in the DNA sample can be quantitatively determined by plotting the fluorescence intensity versus the concentration of AP sites of the DNA sample. The concentration AP sites of the DNA sample can then be correlated with the concentration of plotted AP sites of the control specimen to determine the amount of AP-DNA in the isolated DNA from the biological sample.

To produce control DNA of known AP-DNA concentrations against which the sample of DNA can be compared, double stranded calf thymus can be obtained and specific numbers of AP sites can be selectively produced, as known in the art. Typically a heat/acid depurination buffer treatment can be used to produce useful control samples. Multiple working solution AP-DNA controls of varying concentrations can be produced and utilized in the methods provided. In one embodiment, controls and samples can be assayed by treating the sample of DNA and control DNA specimens in parallel so that the sample and control DNA specimen(s) are each subjected to the same or similar environmental and process conditions so as to remove any such variables from the respective samples when interpreting the results of their comparisons.

In some embodiments, the fluorescent probes described herein may be used in conjunction with non-invasive imaging techniques for in vivo imaging of the fluorescent probe. The term "in vivo imaging" refers to any method, which permits the detection of a fluorescent probe, as described above. For purposes of in vivo imaging, the type of detection instrument available is a major factor in selecting a given fluorescent moiety.

For in vivo imaging, the fluorescent probes can be administered to a subject by, for example, systemic, topical, and/or parenteral methods of administration. These methods include, e.g., injection, infusion, deposition, implantation, or topical administration, or any other method of administration where access to the tissue by the fluorescent probe is desired. In one example, administration of the fluorescent probe can be by intravenous injection of the probe in the subject. Single or multiple administrations of the probe can be given. "Administered", as used herein, means provision or delivery of the fluorescent probe in an amount(s) and for a period of time(s) effective to label cancer cells in the subject.

Fluorescent probes described herein can be administered to a subject in a detectable quantity of a pharmaceutical composition containing a molecular probe or a pharmaceutically acceptable water-soluble salt thereof, to a patient. A "detectable quantity" means that the amount of the detectable compound that is administered is sufficient to enable detection of binding of the compound to the cancer cells. An "imaging effective quantity" means that the amount of the detectable compound that is administered is sufficient to enable imaging of binding of the fluorescent probes to AP sites of the cancer cells.

In some embodiments, the fluorescent probe can be used to measure the efficacy of an anticancer agent in generating AP sites in cancers cells of a subject to which the anticancer agent is administered. Measuring the ability of the anticancer agent to generate AP sites in the cancer cells can be used to determine whether a specific anticancer is effective in treating a subject or a specific cancer. If an anticancer agent administered to a subject is found to not generate AP sites, a therapy using an anticancer agent can be halted and another or different anticancer agent can be selected and be administered to the subject. Additionally, the amount or quantity of AP sites generated by an anticancer agent in a subject to which the anticancer agent is administered can be measure and quantified using the fluorescent probe to determine the efficacy of the therapy. For example, the fluorescent probe can be used to measure quantity of AP sites generated by an anticancer agent. The greater the number or amount of AP sites generated in cancer cells of the subject measured using the fluorescent probe the more effective the anticancer agent can be at treating the cancer in the subject.

One example of an anticancer agent that can be administered to a subject and induce the formation of AP sites in cancer cells of a subject is an intercalating agent, such as bleomycin, adriamycin, quinacrine, echinomycin (a quinoxaline antibiotic), and anthrapyrazoles.

Another example of an anticancer agent that can induce the formation of AP sites in cancer cells of a subject is radiation. Radiation, such as gamma radiation, UVA, and UVB, can also be used to generate AP sites according to the methods of the invention. Ultraviolet light is absorbed in DNA with the formation of UV-specific di-pyrimidine photoproducts. Exposure to gamma irradiation, UVA, and UVB can induce damaged pyrimidine photodimers Anticancer agents that induce the formation of AP sites can further include DNA oxidizing agents, such as hydrogen peroxide.

Anticancer agents that induce the formation of AP sites can also include alkylating agents, such as temozolomide (TMZ), 1,3-bis(2-chloroethyl)-I-nitrosourea (BCNU), $MeOSO_2(CH_2)_2$-lexitropsin (Me-Lex), cis-diamminedichloroplatinum II (cisplat; cis-DDP), mitomycin bioreductive alkylating agents, quinones, streptozotocin, cyclophosphamide, nitrogen mustard family members such as chloroambucil, pentostatin (and related purine analogs), fludarabine, bendamustine hydrochloride, chloroethylating nitrosoureas (e.g., lomustine, fotemustine, cystemustine), dacarbazine (DTIC), and procarbazine. In certain embodiments, the alkylating agent is a nitrosoruea, such as a mustine, carmustine, fotemustine, lomustine, nimustine, ranimustine, or semustine.

In certain embodiments, the anticancer agent is selected from radiosensitizers, such as 5-iodo-2'-deoxyuridine (IUdR), 5-fluorouracil (5-FU), 6-thioguanine, hypoxanthine, uracil, fludarabine, ecteinascidin-743, and camptothecin and analogs thereof.

In some embodiments, a method of monitoring the efficacy of an anticancer agent in generating AP sites in cancer cells of a subject in vivo can include the steps of administering in vivo to the subject an anticancer agent at an amount effective to generate AP sites in cancer cells of the subject. The fluorescent probe can be administered to the subject before, concurrently with the administration of the anticancer agent, and/or after administration of the anticancer agent. The amount or number of the fluorescent probes bound to the AP sites of the cancer cells of the subject can be measured to determine the formation number or amount of AP sites generated or induced by the anticancer agent. In some embodiments, the amount of AP endonuclease inhibitor probes bound to the AP sites of cancer cells of the subject can be measured by visualizing a distribution of the fluorescent probes in the subject (e.g., with an in vivo imaging modality as described herein), and then correlating the distribution of the fluorescent probe with the efficacy of the anticancer agent in generating AP sites.

The number or amount of fluorescent probes bound to AP sites in cancer cells of the subject can be correlated with the amount of AP sites generated by the anticancer agent by comparing the number or amount of bound fluorescent probes to a predetermined value. The predetermined value can be based, for example, upon the number or amount fluorescent probes bound to cancer cell lines after administration of the fluorescent probe but prior to administration of the anticancer agent. An increase or substantial increase in the number of bound fluorescent probes to AP sites of the cancer cells of the subject following administration of the anticancer agent is indicative of the anticancer agent being effective to generate AP sites in the cancer cells of the subject. Conversely, where the number of fluorescent probes bound to AP sites of the cancer cells is substantially the same or only moderately increased following administration of the anticancer agent, the anticancer is not effective or only moderately effective in generating AP sites in cancer cells of the subject.

Other embodiments described herein relate to a kit for assaying AP site of a DNA sample. The kit can include a control DNA specimen having a known concentration of AP-sites and an AP detection reagent that include the fluorescent probe. The kit can also include instructions to explain how one may fluorometrically compare a given sample of DNA and control DNA. The instructions can further include directions on contacting the sample DNA and a set of control DNA specimens each having a known number of AP sites with the AP detection reagent. The kit may also include further instructions on performing fluorometric analysis to correlate the amount of AP-sites in a sample of DNA relative to the control DNA specimens.

Other embodiments described herein relate to a screening assay that can be used to screen for compounds that inhibit repair of AP sites of injured or damaged DNA, such as by base excision repair (BER). Base excision repair (BER) is initiated during replication of DNA and allows for correction of damaged bases/mispaired bases prior to completion of replication. In single-nucleotide BER, the deoxyribose phosphate (dRP) in the abasic site is removed by the lyase activity of DNA pol β. Compounds such as methoxyamine can react with the aldehyde of an AP site, making it refractory to the β-elimination step of the dRP lyase mechanism, thus blocking single-nucleotide BER. AP endonuclease inhibitors may act by binding to AP sites and preventing APE-mediated cleavage of phosphodiester bonds, or by acting directly on AP endonuclease.

The screening assay can be used for identifying compounds that are capable of binding (e.g., covalent binding) with an aldehyde group on an AP site of the DNA. Examples therapeutic agents can include an AP endonuclease inhibitor. Compounds useful as BER inhibitors include AP endonuclease inhibitors such as methoxyamine (MX), N-ethylmaleimide, $O^6$-benzylguanine, and their derivative compounds. It is not intended that the application be limited by the nature of the agents screened in the screening assay. A variety of compounds, including peptides, organic compounds, nonorganic compounds, as well as, formulations of more than one compound, are contemplated.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

This Example describes the synthesis and characterization of fluorescent AP site binding probes.
General Methods
NMR spectra were recorded on a Varian Mercury 300 MHz, a Varian Inova 400, and a Varian Inova 600 MHz spectrometer at room temperature, except where otherwise noted. Chemical shifts for 1H NMR were reported as δ, parts per million, and referenced to $CHCl_3$ at 7.26 ppm or TMS at 0 ppm. Chemical shifts for $^{13}C$ NMR were reported as δ and referenced to the center line of the CDCl3 triplet at 77.0 ppm or $CH_2Cl_2$ pentet at 54.0 ppm. Low resolution mass spectra were recorded on a ThermoScientific LCQ Advantage or a Finnigan LCQ Deca mass spectrometer. Fluorescence data were collected on a Varian Cary Eclipse fluorescence spectrophotometer in a quartz cuvette with a 1 cm pathlength or on a Tecan Infinite M200 scanner. Absorbance data were collected on a Varian Cary 50 Bio UV-Visible Spectrophotometer in a quartz cuvette with a 1 cm path length.
Synthesis

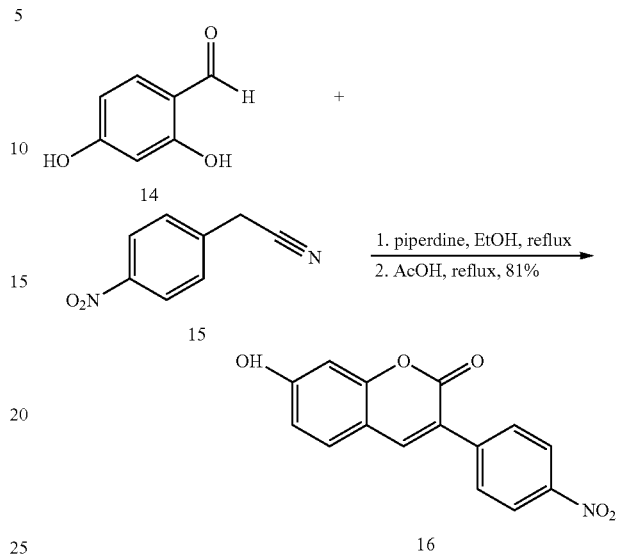

7-hydroxy-3-(4-nitrophenyl)-2H-chromen-2-one (16)

para-Nitrophenylacetonitrile (15, 597 mg, 3.68 mmol) was added to a 25 mL round bottom flask fitted with a magnetic stir bar. A water reflux condenser was fitted to the round bottom. Ethanol (6.0 mL) was added and the solid dissolved upon gentle warming. 2,4-dihydroxybenzaldehyde (14, 500 mg, 3.62 mmol) was added and allowed to dissolve before piperidine (20.0 μL, 0.202 mmol, 0.862 g/mL) was added. The reaction was stirred at reflux for 4 h. The reaction was cooled to r.t. then filtered. The red solid was suspended in glacial acetic acid (7.5 mL) and stirred at reflux for 16 h. The reaction was cooled to r.t., poured into ice water, and filtered. The solid was collected to afford 16 as a yellow solid (827 mg, 81%) without further purification. Rf=0.26 (DCM/PhMe/EtOAc, 5:4:1); $^1H$ NMR (600 MHz, d6-DMSO): δ=10.81 (br s, 1H), 8.39 (s, 1H), 8.29 (d, J=8.9 Hz, 2H), 8.01 (d, J=8.9 Hz, 2H), 7.65 (d, J=8.5 Hz, 1H), 6.85 (dd, J=8.5, 2.0 Hz, 1H), 6.78 (d, J=2.0 Hz, 1H); $^{13}C$ NMR (150 MHz, $d_6$-DMSO): δ=162.1, 159.5, 155.3, 146.5, 143.1, 141.8, 130.6, 129.2, 123.2, 119.7, 113.7, 111.7, 101.7.

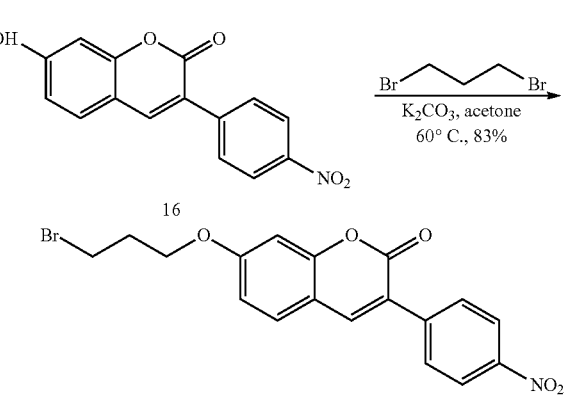

7-(3-bromopropoxy)-3-(4-nitrophenyl)-2H-chromen-2-one (17)

An oven-dried 25 mL round bottom flask fitted with a magnetic stir bar was cooled under a stream of argon. Coumarin 16 (200 mg, 0.708 mmol) and $K_2CO_3$ (203 mg, 1.47 mmol) were added. The flask was evacuated and filled with argon four times. The solids were suspended in dry acetone (9.8 mL) and dibromopropane (600 µL, 5.88 mmol, 1.977 g/mL) was added quickly and all at once. A water reflux condenser was attached and the reaction was stirred at reflux under argon shielded from light for 24 h. The reaction mixture was filtered and the filtrate was concentrated in vacuo. The crude residue was extracted from water with DCM (3×). The combined organic layers were washed with water (2×) and brine, dried over MgSO4, filtered, and concentrated to afford 17 without need for further purification as a yellow solid (236 mg, 83%). Rf=0.71 (EtOAc/hexanes, 1:1); $^1$H NMR (600 MHz, $d_6$-DMSO): δ=8.43 (s, 1H), 8.30 (d, J=8.8 Hz, 2H), 8.02 (d, J=8.8 Hz, 2H), 7.74 (d, J=8.6 Hz, 1H), 7.09 (d, J=2.2 Hz, 1H), 7.04 (dd, J=8.6, 2.2 Hz, 1H), 4.22 (t, J=6.1 Hz, 2H), 3.69 (t, J=6.4 Hz, 2H), 2.29 (tt, J=6.4, 6.1 Hz, 2H); $^{13}$C NMR (125 MHz, $d_6$-DMSO): δ=162.1, 159.4, 155.2, 146.7, 142.8, 141.5, 130.3, 129.3, 123.2, 120.9, 113.2, 112.9, 100.8, 66.2, 31.5, 30.9.

Tert-butyl (3-((3-(4-nitrophenyl)-2-oxo-2H-chromen-7-yl)oxy)propoxy)carbamate (18)

An oven-dried 50 mL round bottom flask fitted with a magnetic stir bar was cooled under argon. Sodium hydride (399 mg, 16.6 mmol) and tert-butylhydroxycarbamate (1.97 g, 14.8 mmol) were added and the flask was purged with argon 5 times. Dry DMF (25 mL) was added and the reaction was stirred at r.t. under argon for 70 minutes. To an oven-dried 100 mL round bottom flask fitted with a magnetic was added coumarin 17 (1.00 g, 2.47 mmol). The flask was purged with argon five times before dry DMF (12.5 mL) was added. The sodium hydride mixture was added to the coumarin solution dropwise. The 50 mL round bottom flask was rinsed with dry DMF (2×6 mL) and the rinsate added to the reaction mixture. The reaction was stirred at room temperature under argon in the dark for 3 h. The reaction was quenched with water (125 mL) then 10% HCl (15 mL). The reaction mixture was extracted with EtOAc (1×50 mL, 2×75 mL). The combined organic layer were washed with water (2×50 mL) and brine (50 mL), dried over $MgSO_4$, filtered, and concentrated. The crude residue was dissolved in DCM and dry loaded onto silica. The crude residue was purified by silica gel chromatography with a mobile phase of 12:7:1 DCM/hexanes/EtOAc gradually increasing to 6:3:1 DCM/hexanes/EtOAc. Concentration afforded 18 as a yellow powder (549 mg, 48%). Rf=0.15 (EtOAc/hexanes, 3:7); $^1$H NMR (400 MHz, CDCl3): δ=8.29 (d, J=8.8 Hz, 2H), 7.91 (d, J=8.8 Hz, 2H), 7.89 (s, 1H), 7.48 (d, J=8.4 Hz, 1H), 7.15 (br s, 1H), 6.92 (dd, J=8.4, 2.4 Hz, 1H), 6.89 (d, J=2.4 Hz, 1H), 4.22 (t, J=6.0 Hz, 2H), 4.07 (t, J=6.0 Hz, 2H), 2.17 (tt, J=6.0, 6.0 Hz, 2H), 1.49 (s, 9H); $^{13}$C NMR (125 MHz, $d_6$-DMSO): δ=162.3, 159.4, 156.1, 155.2, 146.7, 142.9, 141.6, 130.3, 129.3, 123.3, 120.9, 113.2, 112.7, 100.7, 79.5, 71.7, 68.9, 28.0, 27.3.

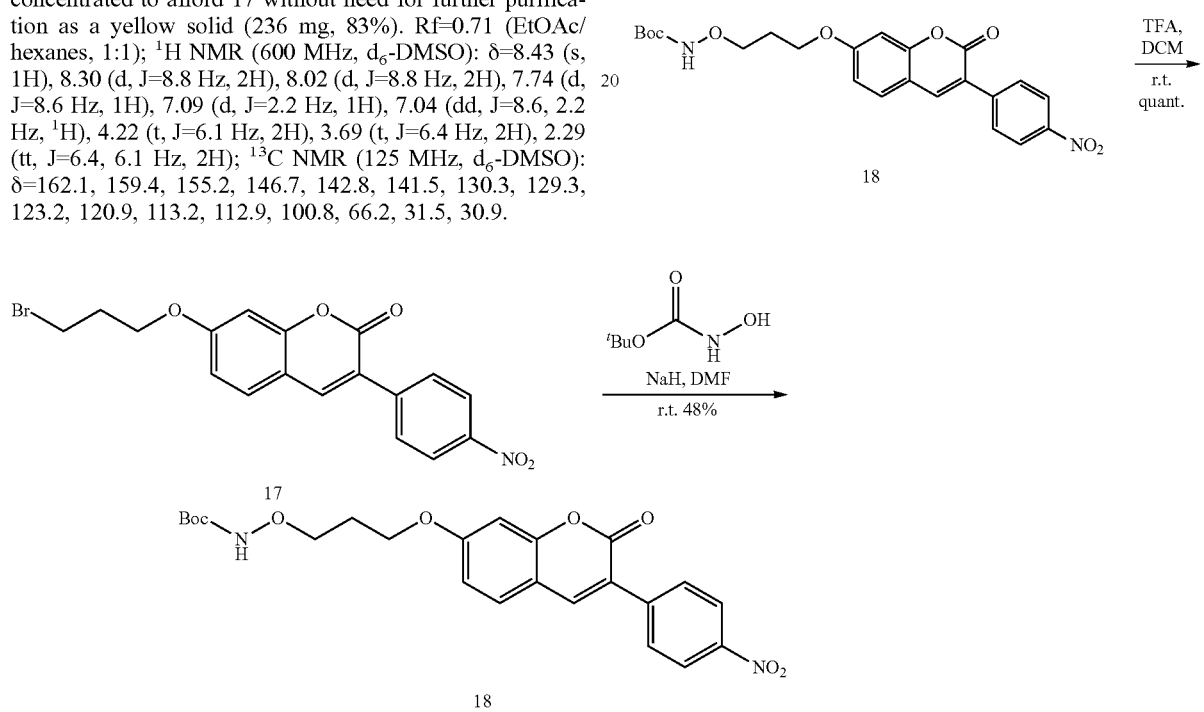

7-(3-(aminooxy)propoxy)-3-(4-nitrophenyl)-2H-chromen-2-one (NpCMX)

To a 100 mL round bottom flask fitted with a magnetic stirbar was added 18 (339 mg, 0.742 mmol) and DCM (50.0 mL). After the coumarin dissolved completely, TFA (1.0 mL, 13.0 mmol, 1.48 g/mL) was added dropwise while stirring. The reaction was stirred at r.t. in the dark for 23 h. Saturated aqueous $NaHCO_3$ (10 mL) was added to quench the reaction. The reaction was then extracted with 40 mL water. The reaction was extracted again with fresh DCM (2×15 mL). The combined organic layers were washed with water (2×40 mL) and brine (1×40 mL). The crude reaction mixture was dried over MgSO$_4$, filtered and concentrated to afford NpCMX without further purification as a yellow solid (268 mg, quant.). R$_f$=0.29 (EtOAc/hexanes, 3:1); $^1$H NMR (400 MHz, CDCl3): δ=8.29 (d, J=8.8 Hz, 2H), 7.91 (m, 3H), 7.48 (d, J=8.6 Hz, 1H), 6.91 (dd, Page|58 J=8.6, 2.3 Hz, 1H), 6.88 (d, J=2.3 Hz, 1H), 5.43 (br s, 2H), 4.15 (t, J=6.3 Hz, 2H), 3.87 (t, J=6.1 Hz, 2H), 2.15 (tt, J=6.3, 6.1 Hz, 2H); $^{13}$C NMR (100 MHz, CDCl$_3$): δ=162.9, 160.2, 147.4, 141.8, 141.5, 129.4, 129.2, 123.6, 122.2, 113.7, 112.8, 101.0, 71.9, 65.6, 28.1.

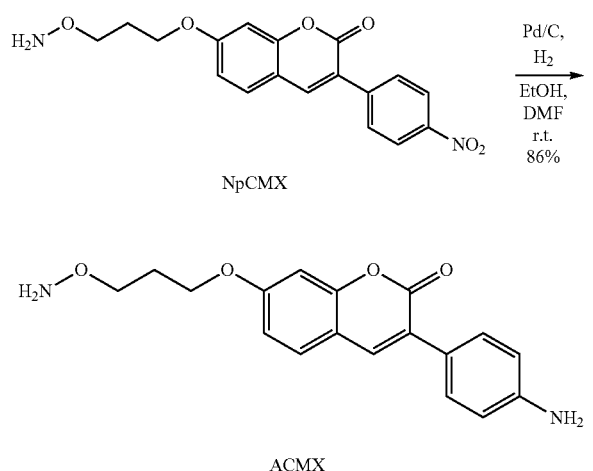

NpCMX

ACMX 7-(3-(aminooxy)propoxy)-3-(4-aminophenyl)-2H-chromen-2-one (ACMX, ACMX)

Palladium on carbon (10 wt %, 15 mg, 0.014 mmol) and coumarin NpCMX were added to a 100 mL round bottom flask fitted with a magnetic stir bar. The flask was purged with argon three times. The coumarin was dissolved in DMF (12 mL) then EtOH (200 proof, 12 mL) was added to the reaction mixture. The flask was purged twice with hydrogen gas (1 atm). The reaction was stirred in the dark at r.t. for 2.5 h in the dark. The reaction mixture was diluted with EtOAc and filtered through a plug of celite. The filtrate was concentrated under vacuum then diluted with water (75 mL). The crude reaction mixture was extracted with EtOAc (1×50 mL, 2×25 mL). The combined organic layers were washed with water (2×50 mL) and brine (1×50 mL). The organic layer was dried over MgSO$_4$, filtered, and concentrated. The crude residue was diluted in DCM then dry loaded on silica. The product was purified by silica gel chromatography with a mobile phase of 75:25:2 EtOAc/hexanes/Et$_3$N gradually increasing to 50:1 EtOAc/Et$_3$N. Concentration afforded ACMX as a yellow solid (78.8 mg, 86%). R$_f$=0.14 (EtOAc/hexanes/Et3N, 75:25:2); $^1$H NMR (600 MHz, d6-DMSO): δ=8.00 (s, 1H), 7.62 (d, J=8.6 HZ, 1H), 7.44 (d, J=8.6 Hz, 2H), 6.96 (d, J=2.3 Hz, 1H), 6.93 (dd, J=8.6, 2.3 Hz, 1H), 6.60 (d, J=8.6 Hz, 2H), 5.38 (s, 2H), 4.66 (t, J=5.3 Hz, 1H), 4.13 (t, J=6.3 Hz, 2H), 3.56 (dt, J=6.1, 5.3 Hz, 2H), 1.88 (tt, J=6.3, 6.1 Hz, 2H); $^{13}$C NMR (125 MHz, d$_6$-DMSO): δ=160.9, 160.2, 154.0, 149.0, 137.0, 128.9, 123.5, 123.4, 121.7, 113.3, 113.2, 112.6, 100.4, 68.9, 57.0, 31.8.

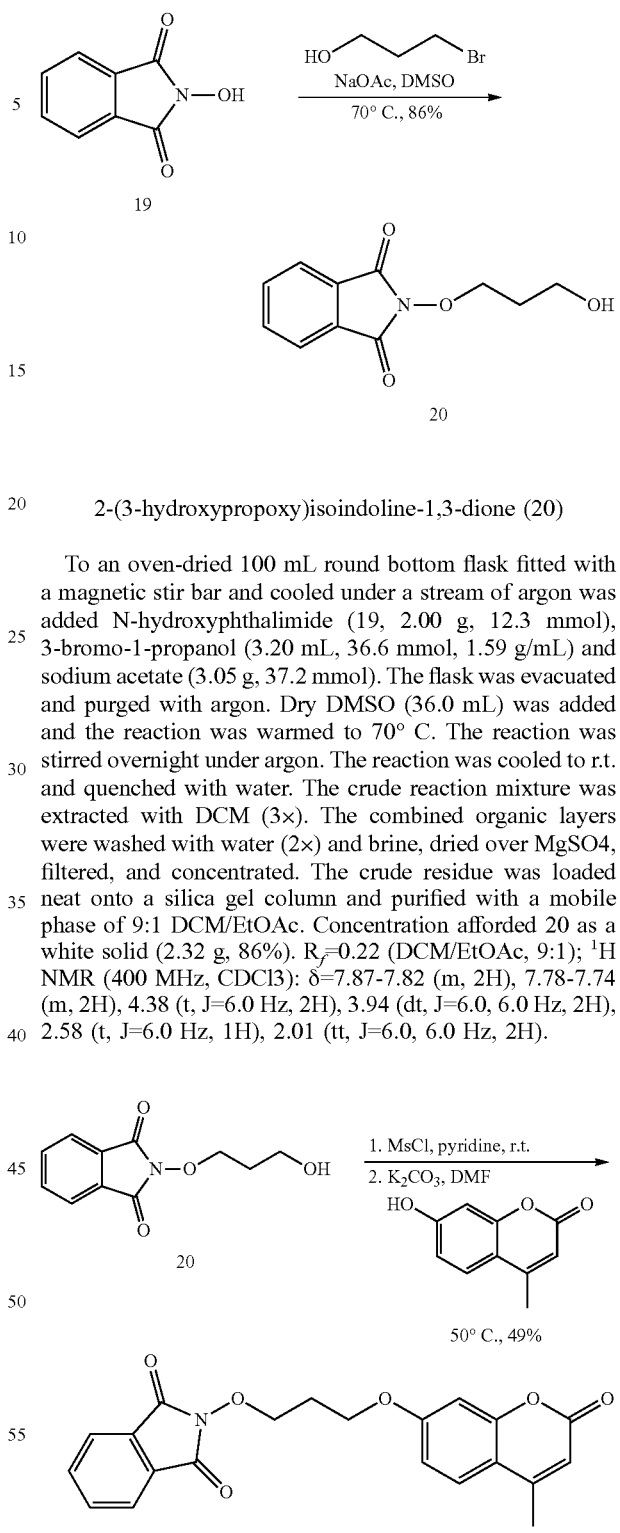

2-(3-hydroxypropoxy)isoindoline-1,3-dione (20)

To an oven-dried 100 mL round bottom flask fitted with a magnetic stir bar and cooled under a stream of argon was added N-hydroxyphthalimide (19, 2.00 g, 12.3 mmol), 3-bromo-1-propanol (3.20 mL, 36.6 mmol, 1.59 g/mL) and sodium acetate (3.05 g, 37.2 mmol). The flask was evacuated and purged with argon. Dry DMSO (36.0 mL) was added and the reaction was warmed to 70° C. The reaction was stirred overnight under argon. The reaction was cooled to r.t. and quenched with water. The crude reaction mixture was extracted with DCM (3×). The combined organic layers were washed with water (2×) and brine, dried over MgSO4, filtered, and concentrated. The crude residue was loaded neat onto a silica gel column and purified with a mobile phase of 9:1 DCM/EtOAc. Concentration afforded 20 as a white solid (2.32 g, 86%). R$_f$=0.22 (DCM/EtOAc, 9:1); $^1$H NMR (400 MHz, CDCl3): δ=7.87-7.82 (m, 2H), 7.78-7.74 (m, 2H), 4.38 (t, J=6.0 Hz, 2H), 3.94 (dt, J=6.0, 6.0 Hz, 2H), 2.58 (t, J=6.0 Hz, 1H), 2.01 (tt, J=6.0, 6.0 Hz, 2H).

2-(3-((4-methyl-2-oxo-2H-chromen-7-yl)oxy)propoxy)isoindoline-1,3-dione (21)

To an oven-dried 100 mL round bottom flask fitted with a magnetic stir bar and cooled under a stream of nitrogen was added N-(3-hydroxypropoxy)phthalamide (20, 1.00 g, 4.53 mmol). The flask was purged with argon. The solid was dissolved in dry pyridine (50 mL, 620 mmol, 0.978 g/mL). Methanesulfonyl chloride (950 µL, 12.3 mmol, 1.48 g/mL) was added and the reaction stirred at r.t. under argon for 2 h. Water was added to quench the reaction and the mixture was quickly extracted with EtOAC (2×). The combined organic layers were washed with water and brine, dried over MgSO4, filtered, and concentrated. 7-Hydroxy-4-methyl-coumarin (519 mg, 2.95 mmol) and potassium carbonate were added. The mixture was suspended in dry DMF and heated to 50° C. The reaction was stirred under argon overnight. The reaction was cooled and extracted with water and EtOAc (3×). The combined organic layers were washed with water (2×) and brine, dried over MgSO4, filtered, and concentrated. The crude residue was purified by silica gel chromatography with a mobile phase of 9:1 DCM/EtOAc. Concentration afforded 21 as a white solid (553 mg, 49%, 60% based on recovered starting material). $R_f$=0.47 (DCM/EtOAc, 9:1); $^1$H NMR (400 MHz, CDCl3): δ=7.87-7.82 (m, 2H), 7.78-7.74 (m, 2H), 7.51 (d, J=8.8 Hz, 1H), 6.90 (dd, J=8.8, 2.4 Hz, 1H), 6.87 (d, J=2.4 Hz, 1H), 6.14 (q, J=1.2 Hz, 1H), 4.43 (t, J=6.2 Hz, 2H), 4.33 (t, J=6.2 Hz, 2H), 2.40 (d, J=1.2 Hz, 3H), 2.3 (tt, J=6.2, 6.2 Hz, 2H); $^{13}$C NMR (100 MHz, CDCl3): δ=161.8, 161.3, 155.2, 152.5, 134.7, 128.8, 125.5, 123.6, 113.7, 112.4, 112, 101.7, 73.7, 66.3, 37.1, 28.1, 18.7.

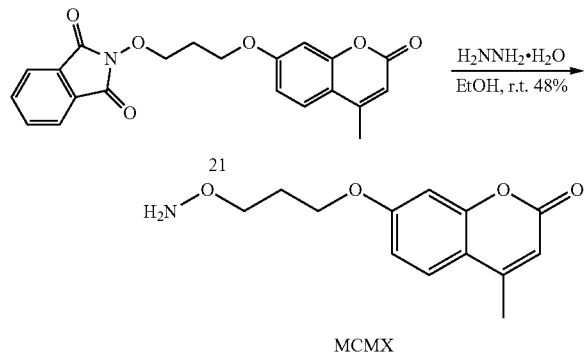

7-(3-(aminooxy)propoxy)-4-methyl-2H-chromen-2-one (MCMX,)

Phthalamide 21 (165 mg, 0.435 mmol) was added to a 100 mL round bottom flask fitted with a magnetic stir bar. The solid was dissolved in DCM (20 mL) and EtOH (20 mL). Hydrazine monohydrate (530 µL, 10.9 mmol, 1.032 g/mL) was added all at once. The reaction was stirred at r.t. loosely capped (to retard evaporation) overnight while shielded from light. The solvents were removed in vacuo. The crude residue was suspended in water and extracted with DCM (3×). The combined organic layers were washed with water (2×) and brine, dried over MgSO4, filtered and concentrated to afford MCMX as a colorless solid (75.8 mg, 70%). $R_f$=0.41 (DCM/hexanes/Et3N, 40:20:1); $^1$H NMR (600 MHz, DMSO): δ=7.67 (d, J=9.4 Hz, 1H), 6.96 (m, 2H), 6.20 (d, J=0.8 Hz, 1H), 4.13 (t, J=6.4 Hz, 2H), 3.67 (t, J=6.2 Hz, 2H), 2.39 (s, 3H), 1.98 (tt, J=6.4, 6.2 Hz, 2H); $^{13}$C NMR (125 MHz, d$_6$-DMSO): δ=161.6, 160.0, 154.6, 153.3, 126.4, 113.0, 112.3, 111.0, 101.1, 71.0, 65.4, 27.6, 18.0.

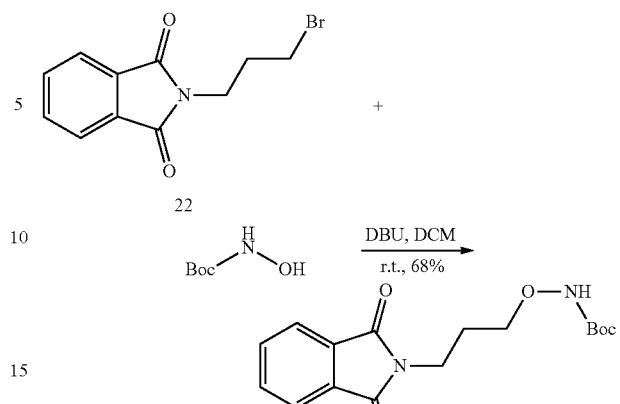

tert-butyl 3-(1,3-dioxoisoindolin-2-yl)propoxycarbamate (23)

22 (10.1 g, 37.5 mmol) and tert-butyl hydroxycarbamate (9.99 g, 75.0 mmol) were added to a dry 250 mL round bottom flask fitted with a stir bar. The flask was sealed with a rubber septum then the atmosphere was evacuated and refilled with argon 5 times. The reagents were dissolved in anhydrous DCM (60.0 mL), added via syringe. DBU was then added via a syringe and the reaction was stirred under argon at room temperature. After five hours, the reaction was quenched with 10% citric acid (50 mL) and extracted with DCM (3×30 mL). The combined organic layers were washed with 10% citric acid (2×50 mL), water (50 mL), then brine (50 mL). The organic layer was dried over MgSO4, filtered, and concentrated. The crude residue was diluted in a trace amount of DCM and purified by silica gel chromatography with a mobile phase of pure DCM then gradually increasing polarity to 9:1 DCM/EtOAc. Concentration gave 23 as a white solid (8.14 g, 68%). $R_f$=0.45 (DCM/EtOAc, 9:1); $^1$H NMR (400 MHz, CDCl3): δ=7.85-7.81 (m, 2H), 7.73-7.68 (m, 2H), 7.34 (br s, 1H), 3.91 (t, J=6.4 Hz, 2H), 3.81 (t, J=6.7 Hz, 2H), 1.99 (tt, J=6.7, 6.4 Hz, 2H), 1.46 (s, 9H); $^{13}$C NMR (100 MHz, CDCl3): δ=168.4, 156.8, 133.9, 132.0, 123.2, 81.7, 73.9, 35.0, 28.2, 27.2.

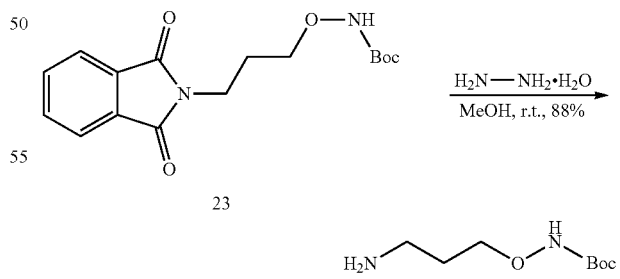

tert-butyl 3-aminopropoxycarbamate (24)

24 was prepared following modification of a literature procedure. Briefly, 23 (1.95 g, 6.10 mmol) was added to a 250 mL round bottom flask fitted with a magnetic stir bar. Methanol (100 mL) was added and the mixture was stirred until the solid was completely dissolved. Hydrazine hydrate (6.0 mL, 124 mmol, 1.032 g/mL) was added all at once while rapidly stirring. The reaction was stirred overnight at room temperature. The next morning, a white precipitate had formed. The methanol was removed in vacuo. The remaining residue was suspended in CHCl$_3$ and filtered. The solid was washed several times with CHCl$_3$ before the filtrate was transferred to a separatory funnel, diluted with water, and extracted. The water was extracted twice more with fresh CHCl$_3$. The organic layers were combined and washed twice with water and once with brine. The organic layer was dried over Na$_2$SO$_4$, filtered, and concentrated to afford 24 as a pale yellow oil (1.02 g, 88%), which was used without further purification. $^1$H NMR (400 MHz, CDCl3): δ=3.95 (t, J=6.1 Hz, 2H), 2.85 (t, J=6.5 Hz, 2H), 1.77 (tt, J=6.5, 6.1 Hz, 2H), 1.47 (s, 9H); $^{13}$C NMR (100 MHz, CDCl$_3$): δ=156.8, 80.8, 74.3, 38.8, 31.0, 28.0.

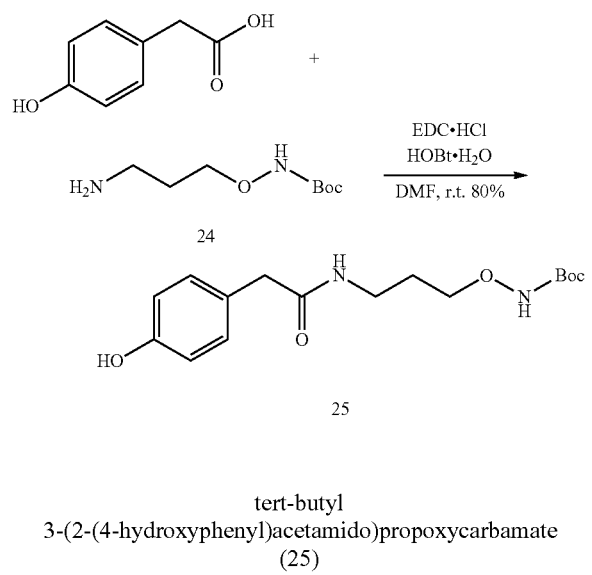

tert-butyl
3-(2-(4-hydroxyphenyl)acetamido)propoxycarbamate
(25)

4-hydroxyphenylacetic acid (350 mg, 2.30 mmol), 24 (416 mg, 2.19 mmol), EDC.HCl (629 mg, 3.28 mmol), and HOBt.H$_2$O (503 mg, 3.28 mmol) were added to an oven-dried 50 mL round bottom flask fitted with a magnetic stir bar. The solids were dissolved in dry DMF (20.0 mL) and the reaction was stirred at room temperature under argon for 24 h. The reaction was then diluted with water (100 mL) and EtOAc (50 mL) and extracted. The aqueous layer was extracted twice more with EtOAc (25 mL). The combined organic layers were washed with water (2×40 mL) and brine (40 mL) then dried over MgSO4, filtered, and concentrated. The crude residue was diluted in a trace amount of DCM and purified by silica gel chromatography with a mobile phase of pure DCM then gradually increasing polarity to 3:2 DCM/MeCN. This product was then further purified by diluting it in EtOAc (25 mL) and washing with sat. NaHCO$_3$ (3×25 mL) and brine (1×25 mL). The organic layer was dried over MgSO4, filtered, and concentrated to afford pure 25 as a white solid (527 mg, 74%). R$_f$=0.23 (DCM/MeCN, 3:2); $^1$H NMR (400 MHz, CDCl$_3$): δ=8.64 (br s, 1H), 8.21 (br s, 1H), 7.34 (br s, 1H), 7.07 (d, J=8.6 Hz, 2H), 6.74 (d, J=8.6 Hz; 2H), 3.84 (t, J=5.6 Hz, 2H), 3.46 (s, 2H), 3.35 (dt, J=6.0, 12 Hz, 2H), 1.71 (tt, J=6.0, 5.6 Hz, 2H), 1.47 (s, 9H); $^{13}$C NMR (100 MHz, CDCl$_3$): δ=172.8, 157.3, 155.7, 130.0, 125.7, 115.6, 81.6, 74.6, 42.4, 37.0, 28.0, 26.8.

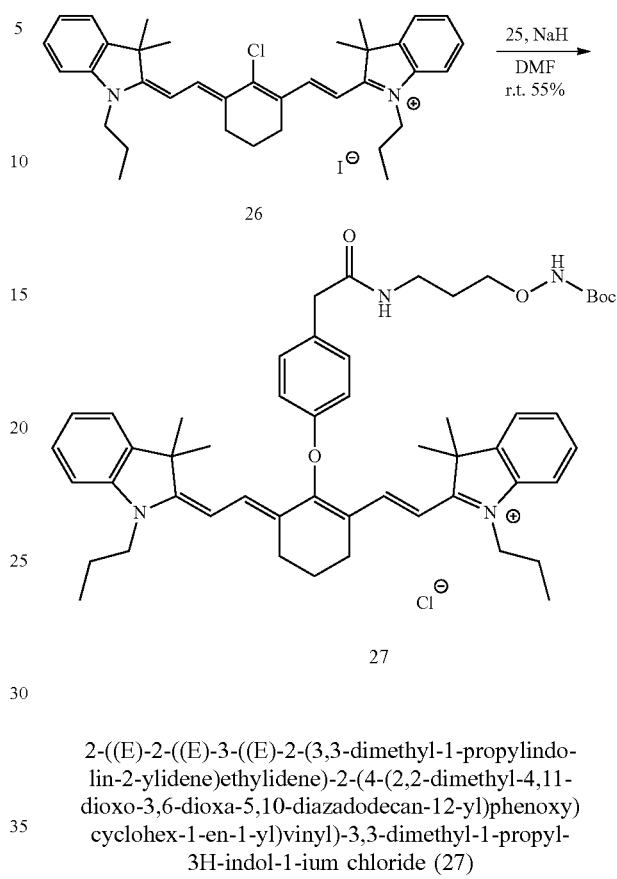

2-((E)-2-((E)-3-((E)-2-(3,3-dimethyl-1-propylindo-lin-2-ylidene)ethylidene)-2-(4-(2,2-dimethyl-4,11-dioxo-3,6-dioxa-5,10-diazadodecan-12-yl)phenoxy)cyclohex-1-en-1-yl)vinyl)-3,3-dimethyl-1-propyl-3H-indol-1-ium chloride (27)

NaH (14.1 mg, 0.588 mmol) and 25 (129 mg, 0.398 mmol) were added to an oven-dried 25 mL round bottom flask fitted with a magnetic stir bar. Dry DMF (3.0 mL) was added and the mixture was stirred under argon at room temperature for 30 min. Meanwhile, IR-780 iodide (26, 230.1 mg, 0.345 mmol) was added to a 15 mL oven-dried heart-shaped flask fitted with a magnetic stir bar. DMF (5.0 mL) was added and 26 was stirred under argon at room temperature shielded from light. After 30 min, the solution of 26 was transferred to the NaH mixture via syringe. The heart-shaped flask was rinsed with dry DMF (4×2 mL) and the rinsate was added to the reaction mixture via syringe. The reaction was stirred at room temperature under argon in the dark for 5 h. The reaction was quenched with water (100 mL) and 10% NH$_4$Cl (aqueous, 50 mL). The aqueous mixture was extracted with DCM (1×100 mL, 1×25 mL) until the aqueous layer remained colorless. The combined organic layers were washed with water (2×50 mL) and brine (1×50 mL), dried over MgSO4, filtered, and concentrated. The crude residue was diluted in a minimal amount of eluent and purified by silica gel chromatography with a mobile phase of 5:20:175 MeOH/MeCN/DCM gradually increasing to 10:15:75 MeOH/MeCN/DCM. Impure fractions were concentrated and this chromatographic method was repeated one time. Pure fraction were combined and concentrated to afford 27 as an emerald solid (163 mg, 55%). R$_f$=0.15 (MeOH/MeCN/DCM, 1:3:16); $_1$H NMR (400 MHz, CDCl$_3$): δ=8.94 (br s, 1H), 8.78 (br t, J=5.6 Hz, 1H), 7.94 (d, J=14.0 Hz, 2H), 7.55 (d, J=8.4 Hz, 2H), 7.35-7.28 (m, 4H), 7.19 (dd, J=7.6, 7.2 Hz, 2H), 7.05 (d, J=8.0 Hz; 2H), 6.95 (d, J=8.8 Hz, 2H), 5.95 (d, J=14.0 Hz, 2H), 3.96 (t, J=7.2 Hz, 4H), 3.92 (t, J=5.6 Hz, 2H), 3.62 (s, 2H), 3.28 (dt, J=6.0, 6.0 Hz, 2H), 2.67 (dd, J=6.0, 5.6 Hz, 4H), 2.04 (dd, J=6.0, 5.6 Hz, 2H), 1.86 (tq, J=7.6, 7.2 Hz, 4H), 1.70 (tt, J=6.0, 5.6 Hz, 2H), 1.45 (s, 9H), 1.32 (s, 12H), 1.04 (t, J=7.6 Hz, 6H); $^{13}$C NMR (75 MHz, CDCl$_3$): δ=172.1, 171.6, 164.8, 158.3, 156.8, 142.3, 141.9, 140.8, 131.3, 131.2, 128.3, 124.9, 122.1, 121.7, 114.1, 110.2, 99.2, 80.3, 73.5, 48.9, 45.6, 42.3, 35.7, 28.1, 27.6, 27.2, 24.1, 20.9, 20.5, 11.4; MS-ESI: m/z [M]$^+$ calcd for C$_{52}$H$_{67}$N$_4$O$_5^+$: 827.51, found: 827.47.

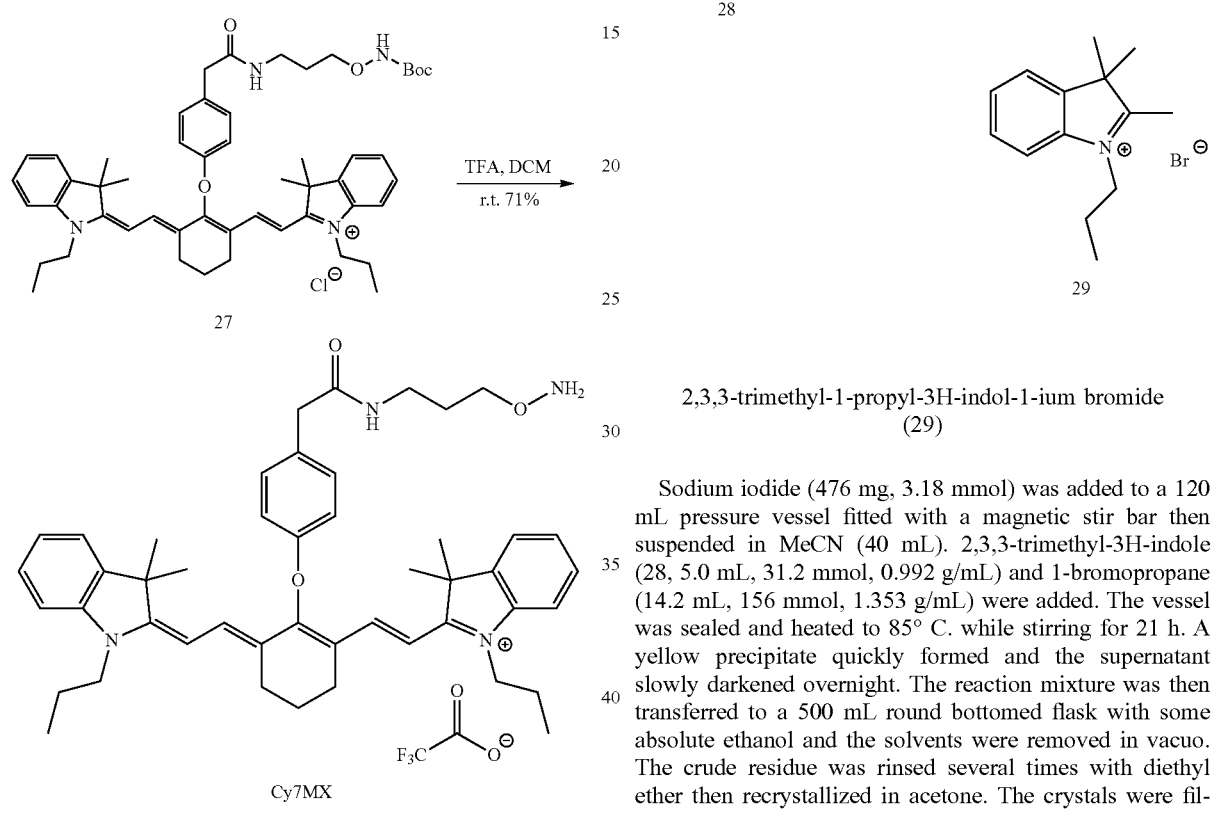

2-((E)-2-((E)-2-(4-(2-((3-(aminooxy)propyl)amino)-2-oxoethyl)phenoxy)-3-((E)-2-(3,3-dimethyl-1-propylindolin-2-ylidene)ethylidene)cyclohex-1-en-1-yl)vinyl)-3,3-dimethyl-1-propyl-3H-indol-1-ium 2,2,2-trifluoroacetate (Cy7MX)

27 (23.0 mg, 0.027 mmol) was dissolved in DCM (1.0 mL). TFA (1.0 mL, 13.0 mmol, 1.48 g/mL) was added and the solution immediately turned from dark green to dark red. The reaction was stirred for 1 h in the dark. The solvents were removed by rotary evaporation to afford pure Cy7MX as an emerald green solid (16 mg, 71%). R$_f$=0.21 (MeOH/DCM, 1:9); $^1$H NMR (600 MHz, CDCl$_3$): δ=8.93-8.20 (br s, 2H), 8.0-7.87 (m, 3H), 7.37-7.26 (m, 6H), 7.19 (dd, J=7.8, 7.2 Hz, 2H), 7.02 (d, J=7.8 Hz, 2H), 6.97 (J=8.4 Hz, 2H), 5.93 (bs d, J=12.6 Hz, 2H), 4.09 (br s, 2H), 3.91 (bs t, J=7.2 Hz, 4H), 3.48 (br s, 2H), 3.23 (br m, 2H), 2.65 (br s, 4H), 2.02 (br m, 2H), 1.83 (tq, J=7.2, 7.2, 4H), 1.67 (br s, 2H), 1.30 (s, 12H), 1.02 (t, J=7.2 Hz, 6H); $^{13}$C NMR (150 MHz, CD2Cl2, −10° C.): δ=174.2, 172.4, 164.7, 161.0, 159.2, 142.5, 141.3, 131.2, 129.6, 128.7, 125.3, 122.6, 122.1, 115.1, 110.7, 99.8, 72.2, 49.3, 46.0, 41.9, 35.8, 27.7, 27.6, 24.4, 21.3, 20.9, 11.7; UV/Vis (EtOH): λ$_{max}$ (ε)=705 nm (29200 L·mol$^{-1}$·cm$^{-1}$), 770 nm (127000 L·mol$^{-1}$·cm$^{-1}$); HRMS-ESI: m/z [M]$^+$ calcd for C$_{47}$H$_{59}$N$_4$O$_3^+$: 727.4587, found: 727.4615.

2,3,3-trimethyl-1-propyl-3H-indol-1-ium bromide (29)

Sodium iodide (476 mg, 3.18 mmol) was added to a 120 mL pressure vessel fitted with a magnetic stir bar then suspended in MeCN (40 mL). 2,3,3-trimethyl-3H-indole (28, 5.0 mL, 31.2 mmol, 0.992 g/mL) and 1-bromopropane (14.2 mL, 156 mmol, 1.353 g/mL) were added. The vessel was sealed and heated to 85° C. while stirring for 21 h. A yellow precipitate quickly formed and the supernatant slowly darkened overnight. The reaction mixture was then transferred to a 500 mL round bottomed flask with some absolute ethanol and the solvents were removed in vacuo. The crude residue was rinsed several times with diethyl ether then recrystallized in acetone. The crystals were filtered and washed three times with diethyl ether to yield 29 as lavender crystals (5.36 g, 61%). R$_f$=0.41 (DCM/MeOH, 9:1); $^1$H NMR (400 MHz, CD3OD): δ=7.94-7.90 (m, 1H), 7.82-7.77 (m, 1H), 7.68-7.64 (m, 1H), 4.81 (s, 3H), 4.54 (dd, J=7.6, 7.6 Hz, 2H), 2.03 (tq, J=7.6, 7.6 Hz, 2H), 1.63 (s, 6H), 1.11 (t, J=7.6 Hz, 3H); $^{13}$C NMR (100 mHz, CD$_3$OD): δ=197.9, 143.4, 142.5, 131.1, 130.5, 124.6, 116.6, 67.0, 56.0, 50.7, 22.9, 22.5, 11.3.

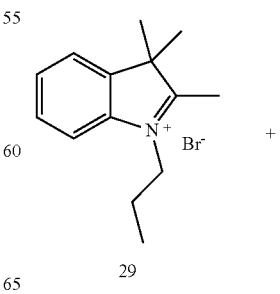

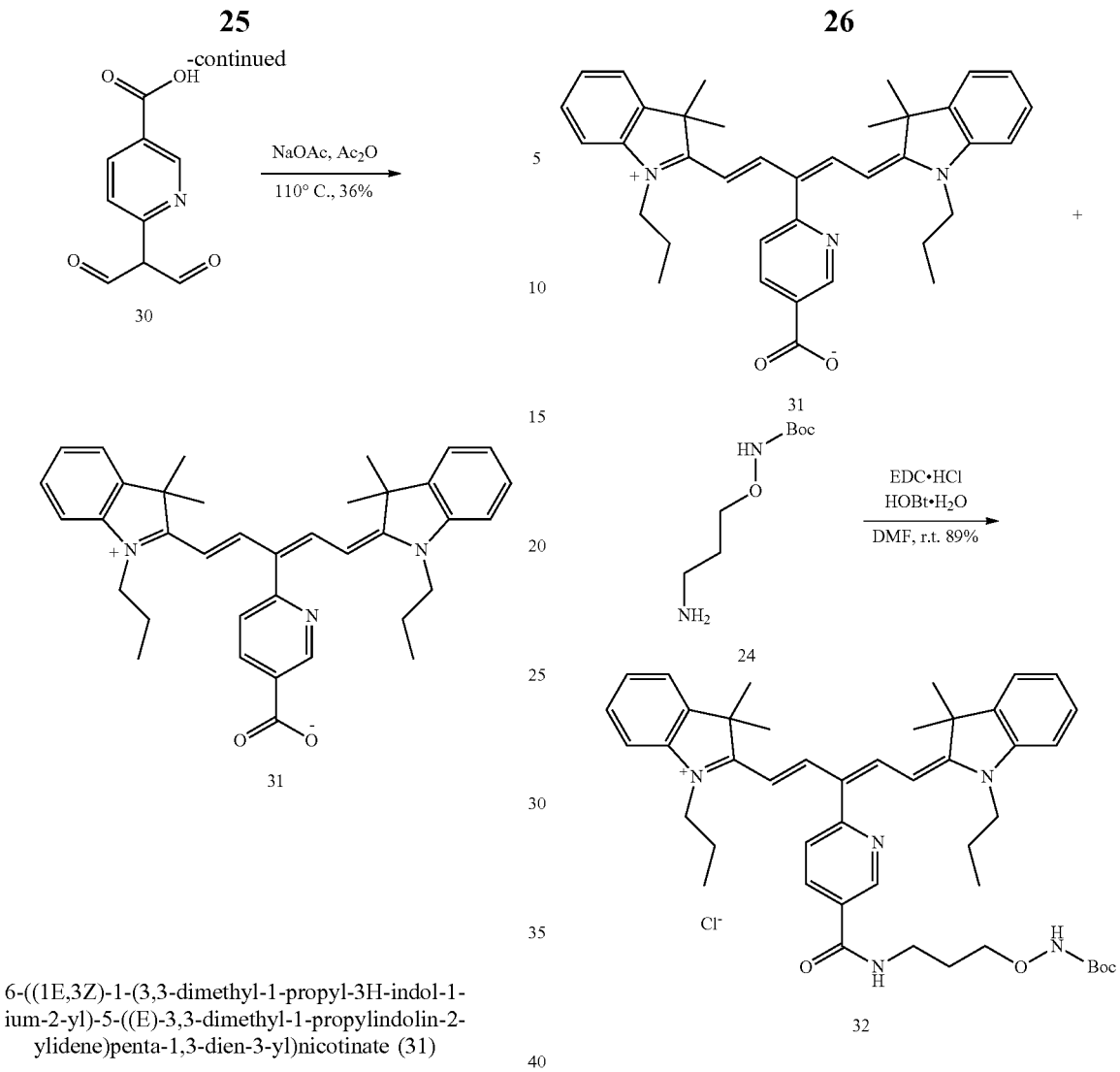

6-((1E,3Z)-1-(3,3-dimethyl-1-propyl-3H-indol-1-ium-2-yl)-5-((E)-3,3-dimethyl-1-propylindolin-2-ylidene)penta-1,3-dien-3-yl)nicotinate (31)

To an oven-dried 48 mL pressure vessel fitted with a magnetic stir bar was added 29 (292 mg, 1.03 mmol), 30 (101 mg, 0.523 mmol), and sodium acetate (130 mg, 1.58 mmol). The solids were suspended in acetic anhydride (4.9 mL, 51.9 mmol, 1.082 g/mL). The vessel was tightly sealed and heated to 110° C., while stirring, shielded from light for 2 h. The reaction was cooled to r.t. and quenched with water (50 mL). The reaction mixture was extracted with DCM (3×25 mL). The combined organic layers were washed with water (2×25 mL) and brine (25 mL), dried over MgSO4, filtered, and concentrated. The crude residue was purified by silica gel chromatography with a mobile phase of 100% DCM increasing to 19:1 DCM/MeOH then 9:1 DCM/MeOH. Concentration afforded 31 as a dark blue solid (50.3 mg, 36%). $R_f$=0.29 (DCM/MeOH, 9:1); $^1$H NMR (400 MHz, CDCl3): δ=9.61 (s, 69 1H), 8.83 (br d, J=6.0 Hz, 1H), 8.02 (d, J=14.0 Hz, 2H), 7.42-7.24 (m, 7H), 7.08 (d, J=8.0 Hz, 2H), 5.88 (d, J=14.0 Hz, 2H), 3.72 (t, J=6.6 Hz, 4H), 1.78 (s, 12H), 1.71 (tq, J=7.2, 6.6 Hz, 4H), 0.84 (t, J=7.2 Hz, 6H); 13C NMR (100 MHz, CDCl$_3$): δ=173.7, 170.9, 155.7, 152.5, 152.0, 141.4, 140.9, 138.5, 132.1, 130.4, 128.2, 125.0, 124.3, 122.0, 110.5, 100.8, 49.2, 45.1, 27.7, 20.3, 11.0.

2-((1E,3Z)-3-(5-((3-(((tert-butoxycarbonyl)amino)oxy)propyl)carbamoyl)pyridin-2-yl)-5-((E)-3,3-dimethyl-1-propylindolin-2-ylidene)penta-1,3-dien-1-yl)-3,3-dimethyl-1-propyl-3H-indol-1-ium chloride (32)

To an oven dried 15 mL round bottom flask fitted with a magnetic stir bar was added 31 (53.0 mg, 0.095 mmol), 24 (22.1 mg, 0.116 mmol), EDC hydrochloride (27.7 mg, 0.144 mmol), and HOBt monohydrate (23.5 mg, 0.153 mmol). The solids were dissolved in dry DMF (5.0 mL). The reaction was stirred under argon at r.t. shielded from light overnight. The reaction was diluted with water (25 mL) and extracted with DCM (3×25 mL). The combined organic layers were washed with water (3×25 mL) and brine (25 mL), dried over Na$_2$SO$_4$, filtered, and concentrated. The crude residue was purified by silica gel chromatography with a mobile phase of 16:3:1 DCM/MeCN/MeOH. The column and collected fractions were shielded from light during purification. Concentration afforded 32 as a dark blue solid (64.4 mg, 89%). $R_f$=0.31 (DCM/MeOH, 9:1); $^1$H NMR (400 MHz, CDCl$_3$): δ=9.66 (br t, J=5.6 Hz, $^1$H); 9.45 (d, J=1.6 Hz, 1H), 9.20 (br s, 1H), 9.02 (dd, J=8.0, 1.6 Hz, 1H), 8.03 (d, J=14.2 Hz, 2H), 7.47 (d, J=8.0 Hz, 1H), 7.42-7.25 (m, 6H), 7.09 (d, J=7.6 Hz, 2H), 5.90 (d, J=14.2 Hz, 2H), 4.11 (t, J=5.6 Hz, 2H), 3.80 (br t, J=7.0 Hz, 4H), 3.73 (dt, J=6.0, 5.6 Hz, 2H), 2.04 (tt, J=6.0, 5.6, 2H), 1.79 (s, 12H), 1.74 (tq, J=7.2, 7.0 Hz, 4H), 1.47 (s, 9H), 0.86 (t, J=7.2 Hz, 6H); $^{13}$C NMR (150 mHz, CDCl$_3$): δ=173.7, 165.8, 157.0, 155.7, 152.1, 150.8, 142.0, 141.0, 137.2, 132.3, 129.9, 128.8, 125.6, 125.0, 122.2, 111.0, 101.5, 80.6, 74.4, 49.4, 45.9, 37.1, 28.3, 28.2, 27.6, 20.8, 11.5.

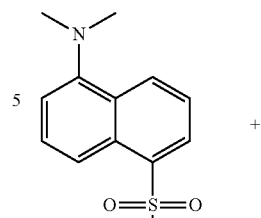

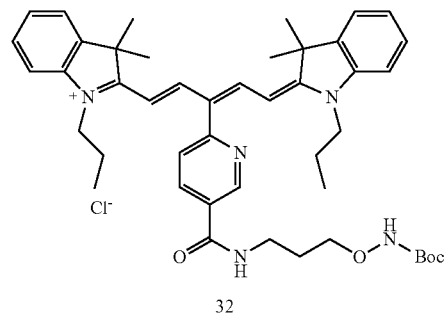

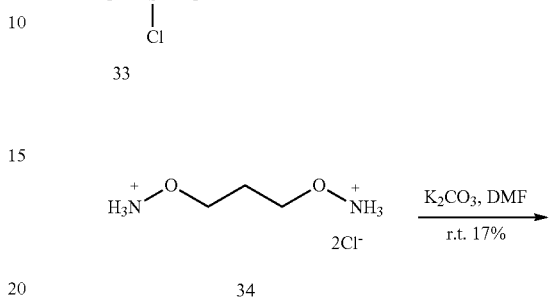

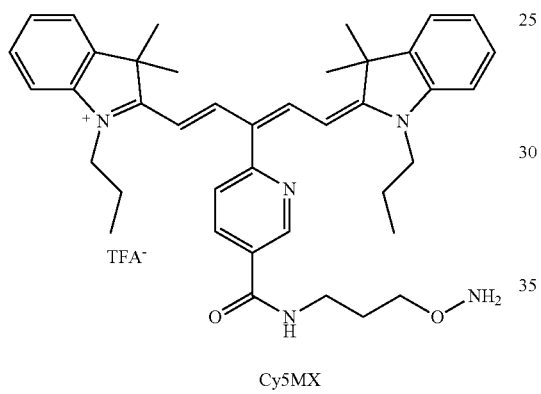

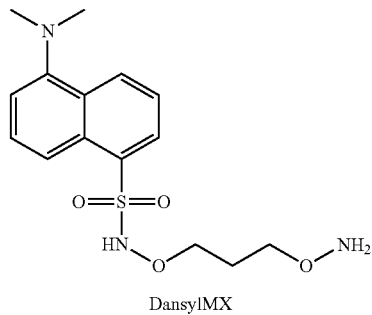

2-((1E,3Z)-3-(5-((3-(aminooxy)propyl)carbamoyl)pyridin-2-yl)-5-((E)-3,3-dimethyl-1-propylindolin-2-ylidene)penta-1,3-dien-1-yl)-3,3-dimethyl-1-propyl-3H-indol-1-ium 2,2,2-trifluoroacetate (Cy5MX, Cy5MX)

To a 4 dram vial fitted with a magnetic stir bar was added 32 (18.1 mg, 0.024 mmol). The solid was dissolved in DCM (1.0 mL) and trifluoroacetic acid (1.0 mL, 13 mmol, 1.48 g/mL) was added. The reaction was shielded from light and stirred at r.t. for 1 h. The reaction was concentrated in vacuo to afford Cy5MX as dark blue solid (18.0 mg, quantitative) without further purification. R$_f$=0.066 (DCM/MeCN/MeOH, 16:3:1); $^1$H NMR (500 MHz, CDCl$_3$): δ=9.51 (br s, 1H), 9.06 (br s, 1H), 8.76 (br s, 1H), 8.08-8.05 (m, 4H), 7.42 (m, 4H), 7.33 (m, 2H), 7.18 (m, 2H), 5.90 (br s, 2H), 4.34 (br s, 2H), 3.90 (m, 4H), 3.68 (br s, 2H), 2.05 (br s, 2H), 1.73 (asymmetric br s, 16H), 0.87 (br s, 6H); $^{13}$C NMR (125 mHz, CDCl3): δ=176.1, 163.2, 160.5 (q, J=39 Hz), 152.2, 144.4, 143.2, 141.3, 131.2, 128.9, 126.8, 122.3, 118.7, 116.4, 114.5 (q, J=284 Hz), 114.2, 111.9, 111.7, 99.9, 73.3, 50.2, 46.0, 37.1, 27.4, 27.1, 20.8, 10.8.

N-(3-(aminooxy)propoxy)-5-(dimethylamino)naphthalene-1-sulfonamide (DansylMX)

To an oven-dried 25 mL round bottom flask fitted with a magnetic stir bar was added 34 (245 mg, 1.37 mmol). The flask was evacuated and purged with argon. The solid was suspended in dry DMF (4.0 mL). To an oven-dried 5 mL pear-shaped flask was added dansyl chloride (33, 403 mg, 1.49 mmol). The solid was dissolved in dry DMF (2.0 mL). The dansyl chloride solution was added to the 25 mL round bottom flask. The pear-shaped flask was rinsed with dry DMF (5×2 mL) and the rinsate was added to the reaction mixture. The reaction was stirred under argon at r.t. overnight. The crude reaction mixture was diluted with water and extracted with EtOAc (3×). The combined organic layers were washed with water (2×) and brine, dried over MgSO4, filtered, and concentrated. The crude residue was purified by silica gel chromatography with a mobile phase of 7:3 DCM/EtOAc. Concentration afforded DansylMX as a yellow solid (79 mg, 17%). R$_f$=0.26 (DCM/EtOAc, 7:3); $^1$H NMR (400 MHz, CDCl$_3$): δ=8.57 (d, J=8.8 Hz, 1H), 8.31 (d, J=7.2 Hz, 1H), 8.27 (d, J=8.4 Hz, 1H), 7.56-7.51 (m, 2H), 7.16 (d, J=7.6 Hz, 1H), 3.90 (t, J=6.4 Hz, 2H), 3.38 (t, J=6.4 Hz, 2H), 2.86 (s, Page|72 6H), 1.74 (tt, J=6.4, 6.4 Hz, 2H); 13C NMR (100 MHz, CDCl$_3$): δ=152.0, 132.1, 131.6, 131.5, 130.0, 129.7, 128.8, 123.2, 118.3, 115.3, 74.2, 72.2, 45.4, 27.0.

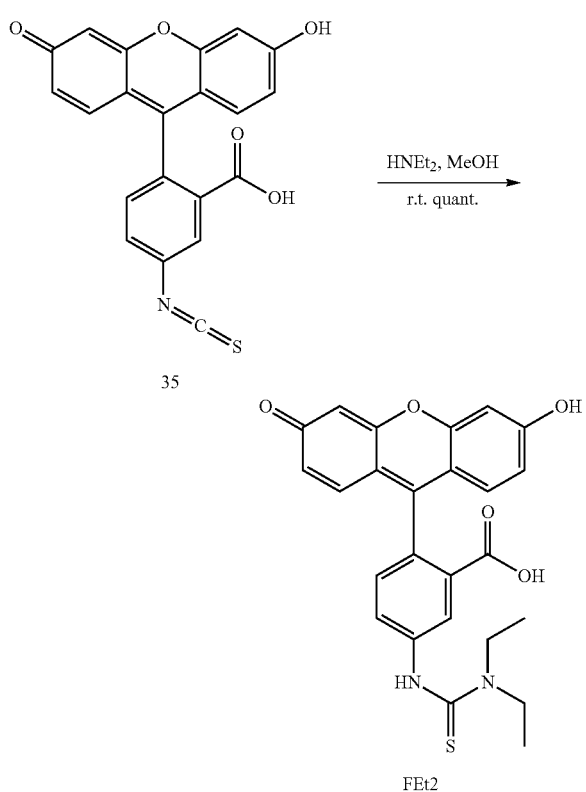

5-(3,3-diethylthioureido)-2-(6-hydroxy-3-oxo-3H-xanthen-9-yl)benzoic acid (FEt2)

Fluorescein isothiocyanate (35, 143 mg, 0.367 mmol) was added to a 25 mL pear-shaped flask and dissolved in methanol (20 mL). Diethylamine (200 μL, 1.93 mmol, 0.707 g/mL) was added all at once. The reaction was stirred at r.t. overnight shielded from light. The solvent was removed in vacuo to afford FEt2 (FEt2) as an orange powder (196 mg, quant.). $R_f$=0.12 (DCM/MeOH/AcOH, 95:5:2); $^1$H NMR (300 MHz, CD3OD): δ=7.95 (s, 1H), 7.61 (d, J=8.1 Hz, 1H), 7.19-7.14 (m, 3H), 6.55-6.51 (m, 4H), 3.87 (q, J=6.9 Hz, 4H), 1.31 (t, J=6.9 Hz, 6H); $^{13}$C NMR (75 MHz, CD$_3$OD): δ=181.8, 181.4, 161.1, 160.1, 143.1, 141.1, 132.7, 131.5, 130.6, 128.9, 128.7, 123.7, 113.7, 104.3, 46.7, 13.1.

Fluorescence Quantum Yield Measurements

Fluorescent quantum yields were determined by a comparative method to an indocyanine green (ICG) standard (Φ=0.132 in EtOH) with refractive index correction according to Equation 1:

$$\Phi = \Phi_R \left(\frac{F}{F_R}\right)\left(\frac{1-10^{-A_R}}{1-10^{-A}}\right)\left(\frac{n^2}{n_{R2}}\right) \quad \text{Equation 1}$$

where Φ is the quantum yield; F is the integrated fluorescence intensity (area); A is the absorbance; n is the refractive index of the solvent (ethanol, 1.3611; acetonitrile, 1.3442; water, 1.333; and chloroform, 1.4459); and R is the reference sample, ICG in EtOH. Sample and reference fluorophores were excited at 700 nm and emission spectra integrated from 705 to 1000 nm and absorption measurements were collected at 700 nm. Data were collected in a quartz cuvette with a 1 cm pathlength. Absorbance maxima for each sample were kept at or below 0.2 absorbance units to avoid inner filter effects. Solvents used were spectroscopic grade ethanol and HPLC grade acetonitrile, HPLC grade chloroform, and HPLC grade water. For the water solution, Cy7MX was first dissolved first in MeCN and diluted at least 200 fold.

Synthesis of Compounds for AP Site Detection

Fluorescent AP site binding probes were intended for three broad applications: detection of damage in purified DNA, in cells, and in small animals. For the two former applications, fluorescence in the visible range is desirable for compatibility with existing microscopes and plate readers as NIR dyes are typically beyond the detection channels of common fluorescent microscopes. Conversely, red and NIR fluorescence, which has better tissue penetration and less nonspecific absorption than UV or visible dyes, is desirable for small animal imaging.

Several compounds were synthesized based on the visible emitting coumarin, dansyl, and pentamethine cyanine cores as well as the NIR heptamethine cyanine frame. To indicate their similar reactivity to MX, the probes are identified with tags ending with MX.

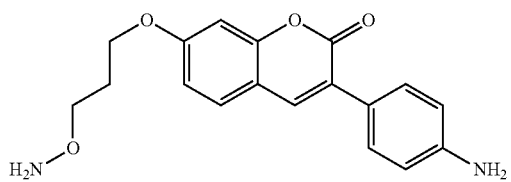

ACMX

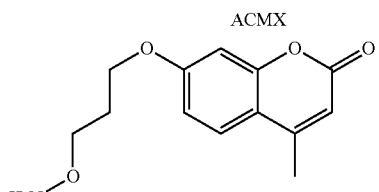

MCMX

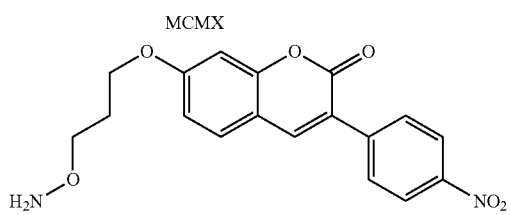

NpCMX

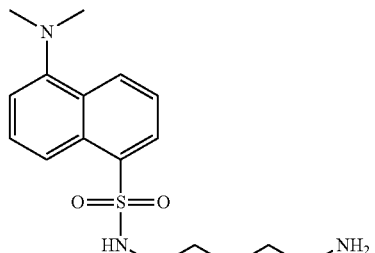

DansylMX

-continued

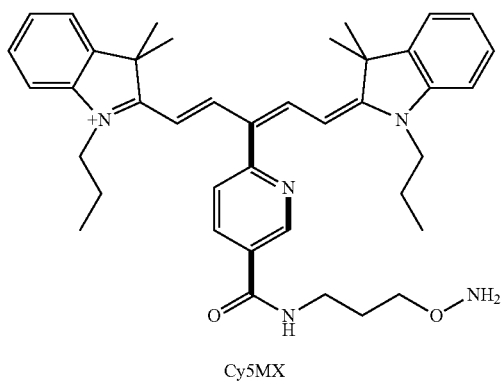

Cy5MX

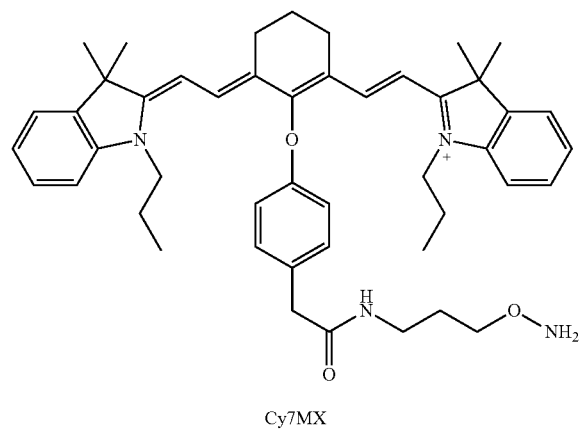

Cy7MX

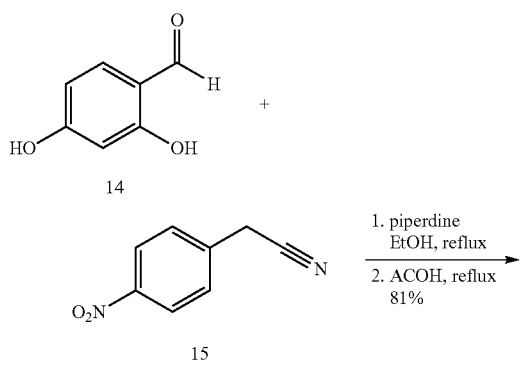

-continued

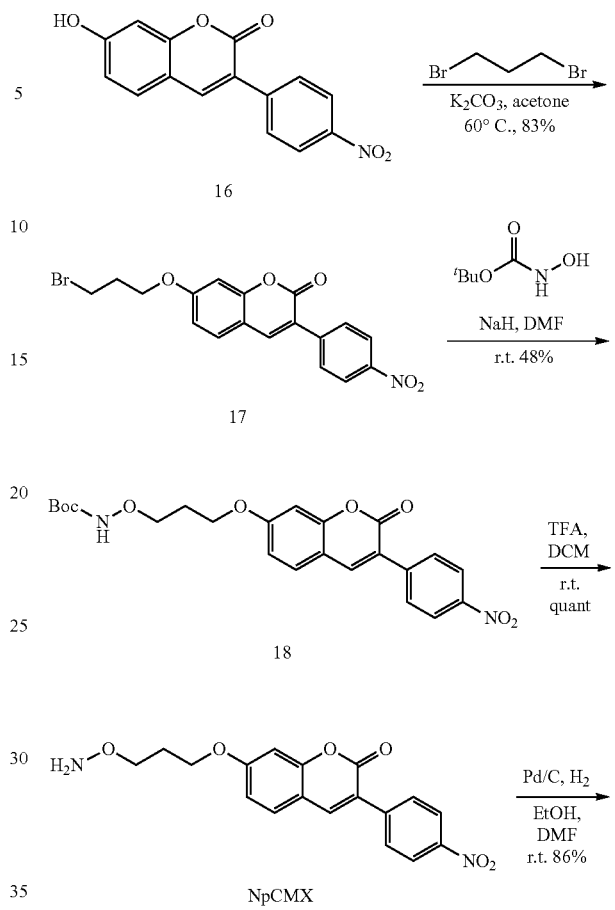

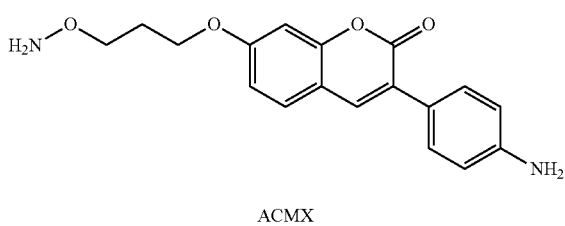

ACMX

The synthesis of two coumarin-based probes began with a piperidine-catalyzed Knoevenagel condensation between 2,4-dihydroxybenzaldehyde (14) and paranitrophenylacetonitrile (15) to afford 16 in 81% yield. An excess of 1,3-dibromopropane ensured only minor dimer formation in the SN2 reaction with 16 to afford 17 in 83% yield. A second SN2 reaction between 17 and tert-butylhydroxycarbamate gave the Bocprotected precursor 18 in moderate 48% yield. A quantitative deprotection of the Boc group gave final compound NpCMX, termed NpCMX for Nitrophenyl Coumarin MX. A palladium catalyzed reduction of the nitro group in NpCMX afforded ACMX, termed ACMX for Aniline Coumarin MX, in 86% yield (Syntheses of NpCMX and ACMX).

A third coumarin-based probe was synthesized starting with an SN2 reaction between N-hydroxyphthalimide, 19, and 3-bromopropan-1-ol to give 20 in 86% yield. A methanesulfonyl chloride promoted dehydration tethered 7-hydroxy-4-methylcoumarin to the phthalimide-protected arm to give 21 in 49% yield over two steps. Hydrazine deprotection afforded MCMX (Methyl Coumarin MX, MCMX) in 20% overall yield (Synthesis of MCMX).

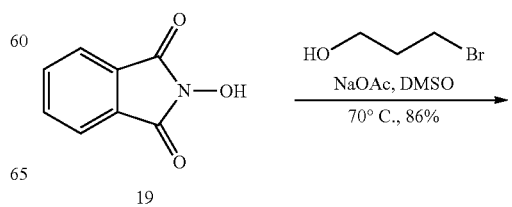

33
-continued

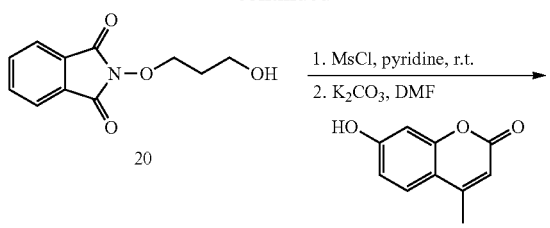

20

50° C., 49%

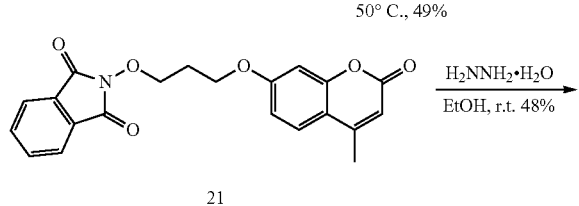

21

34
-continued

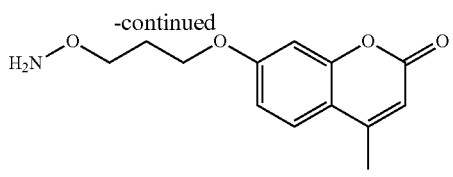

MCMX

Using a modified, two-step procedure, which afforded a higher yield than previously reported, N-(3-bromopropyl) phthalimide, 22, and tert-butyl hydroxycarbamate were coupled to give 23 and subsequent deprotection afforded intermediate 24. An EDC and HOBt amide coupling reaction between 24 and 4-hydroxyphenylacetic acid afforded 25 in 80% yield. An SRN1 reaction between cyanine dye 26 and 25 to give 27, followed by Boc deprotection afforded the heptamethine cyanine Cy7MX (Cy7MX) in 39% yield over two steps (Synthesis of Cy7MX).

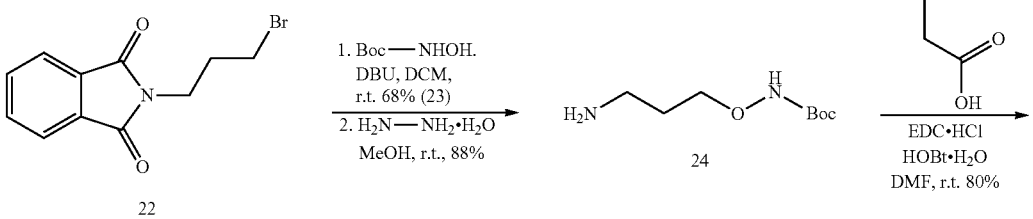

25

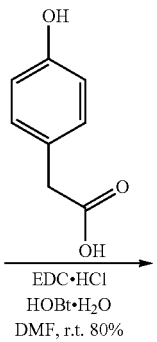

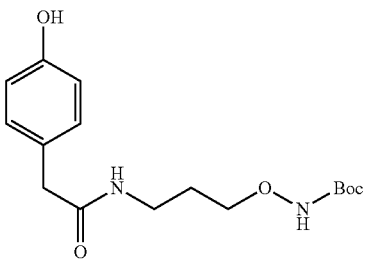

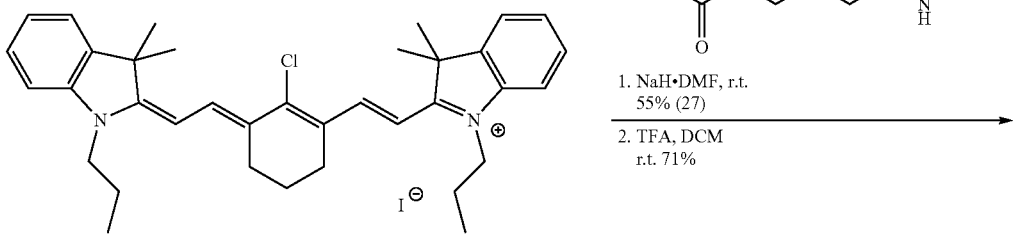

26

-continued
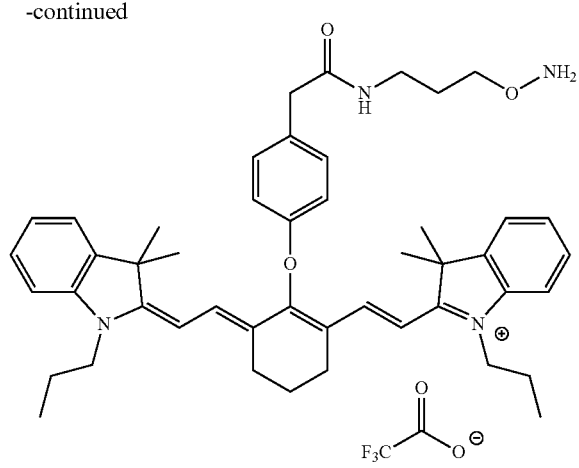
Cy7MX
2,3,3-Trimethyl-3H-indole (28) and 1-bromopropane were reacted to generate the ammonium salt 29 in 61% yield. Two Knoevenagel condensations between two equivalents of 29 and one molar equivalent of 29 generated the zwitterion 31. An amide coupling between 31 and 24 afforded 32 in 89% yield. Boc deprotection of 32 afforded the pentamethine cyanine probe, Cy5MX (Cy5MX, Synthesis of Cy5MX).
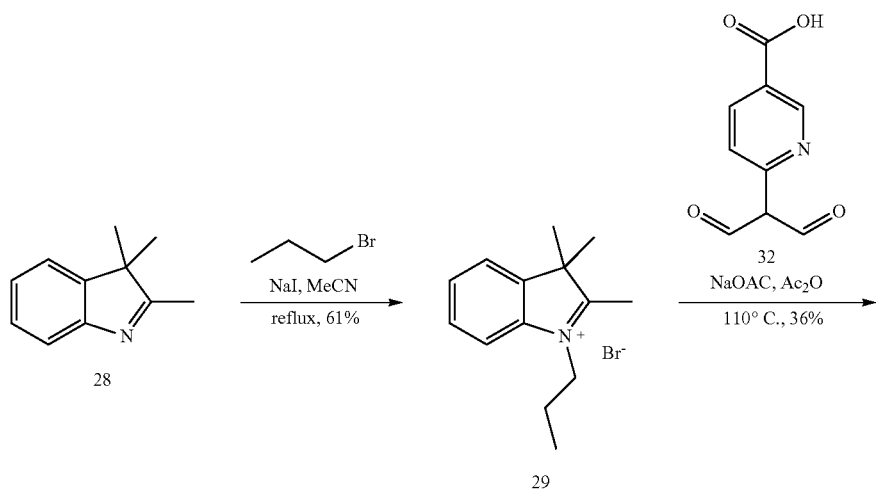

-continued

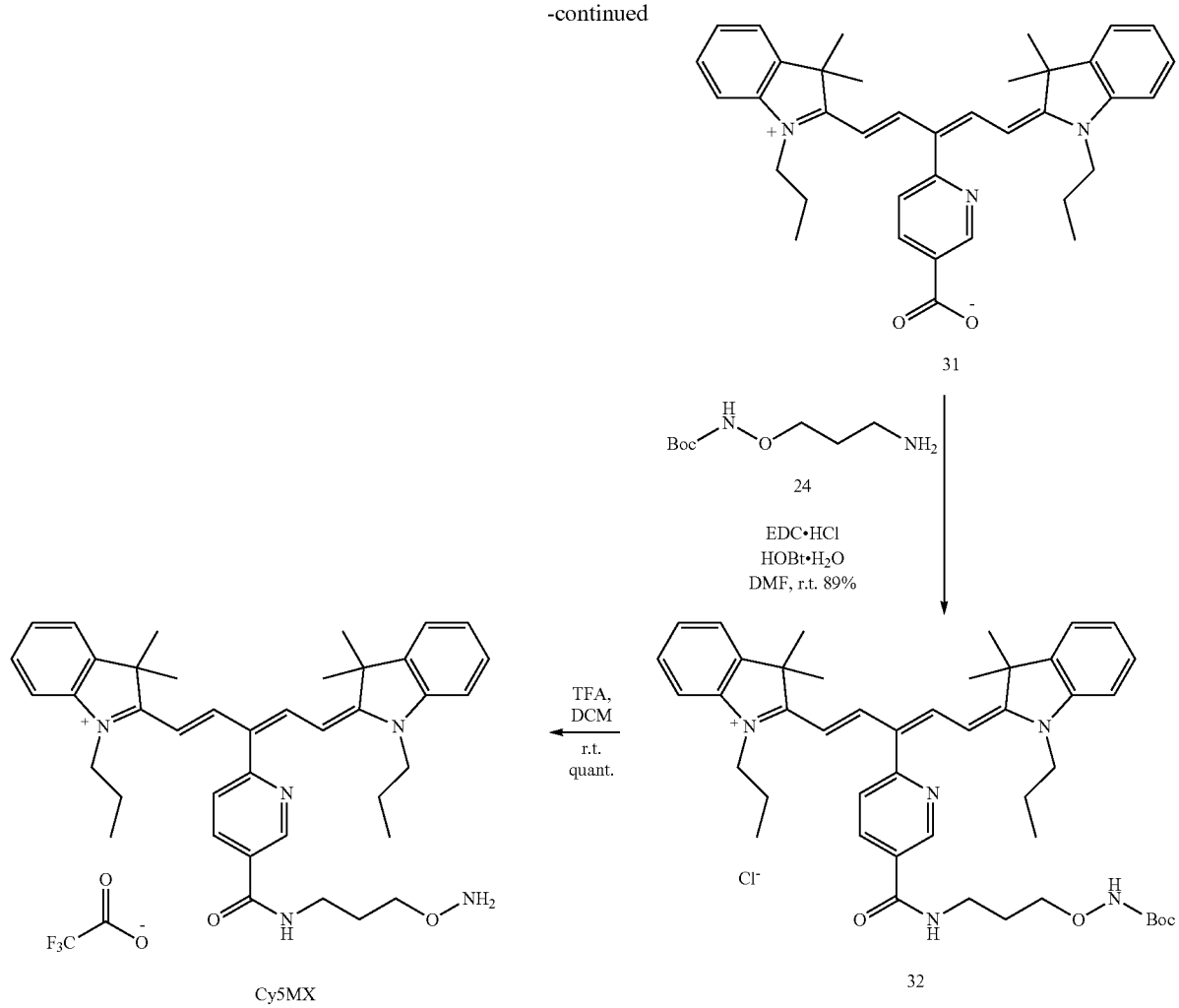

A one step substitution reaction between dansyl chloride (33) and, O,O'-(propane-1,3-diyl)bis(hydroxylamine) hydrochloride (34) afforded dansylMX (DansylMX) in 17% yield (Scheme 9, Synthesis of damsylMX). The yield of DansylMX suffered as a mixture of the title compound, the dimer, and DMF coupled products resulted. The structures of DMF coupled products were confirmed by ¹H NMR.

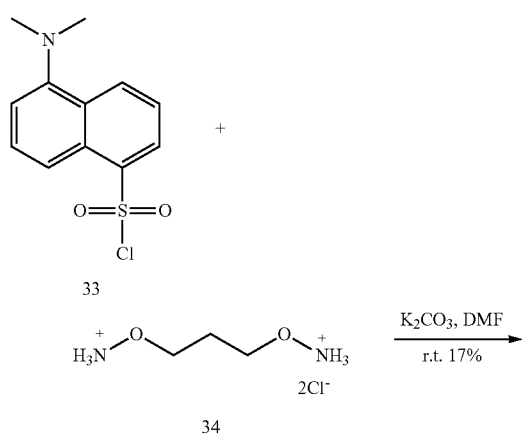

-continued

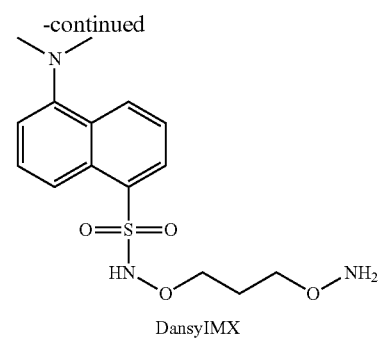

DansylMX

A fluorescein derivative called F422 (F422, Marker Gene product #M1036, Scheme 10) has been used in our labs as a fluorescent probe for AP sites. In order to model nonspecific probe binding using F422, a control compound was synthesized, termed FEt2 (FEt2). A one step reaction starting from fluorescein isothiocyanate (35) and diethylamine afforded FEt2 in quantitative yield (Structure of F422 and synthesis of control compound FEt2).

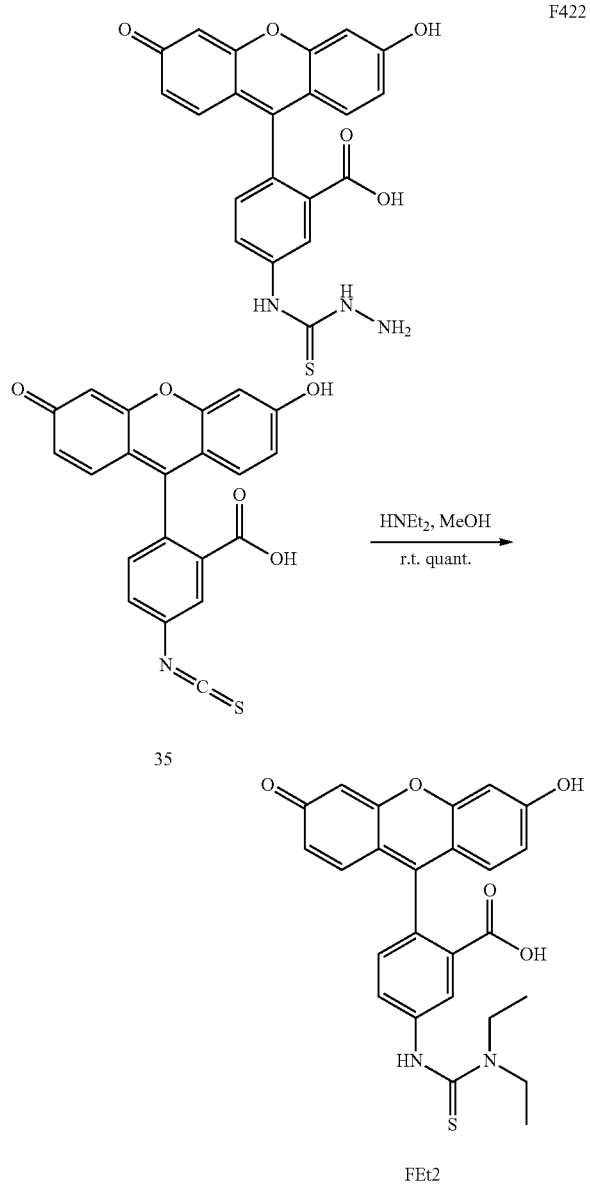

Fluorescent Characterization of Probes

To characterize the fluorescent properties, the absorption and emission spectra were collected for all final compounds. Table 1 summarizes the maxima of absorption and emission for these compounds in ethanol. These data were used to optimize detection channels.

TABLE 1

Summary of absorption and emission wavelengths for AP site binding probes

| Probe | λabs max (nm) | λem max (nm) | Stokes shift (nm) |
|---|---|---|---|
| ACMX | 370 | 450 | 80 |
| MCMX | 325 | 375 | 50 |
| NpCMX | 365 | 550 | 185 |
| DansylMX | 340 | 540 | 200 |
| Cy5MX | 640 | 660 | 20 |
| Cy7MX | 770 | 796 | 20 |

Further characterization was conducted for Cy7MX (Table 2), Cy7MX, because it was chosen for extensive investigation in biological studies. The absorption and emission spectra were collected in polar protic (water and ethanol), polar aprotic (acetonitrile), and relatively nonpolar (chloroform) solvents. No solvatochromism was observed for Cy7MX. The extinction coefficient and the fluorescence quantum yields for Cy7MX compared favorably to other heptamethine cyanine dyes.

TABLE 2

Fluorescence and absorbance properties of Cy7MX in various solvents

| Solvent | ε ($M^{-1}cm^{-1}$) | λabs (nm) | λem (nm) | Φ (%) |
|---|---|---|---|---|
| H$_2$O | 140,000 | 767 | 790 | 6.3 |
| EtOH | 127,000 | 770 | 796 | 36.3 |
| MeCN | 154,000 | 767 | 789 | 45.9 |
| CHCl$_3$ | Not determined | 770 | 791 | 32.6 |

Compound Screening by Dose-Response

Figure 1:
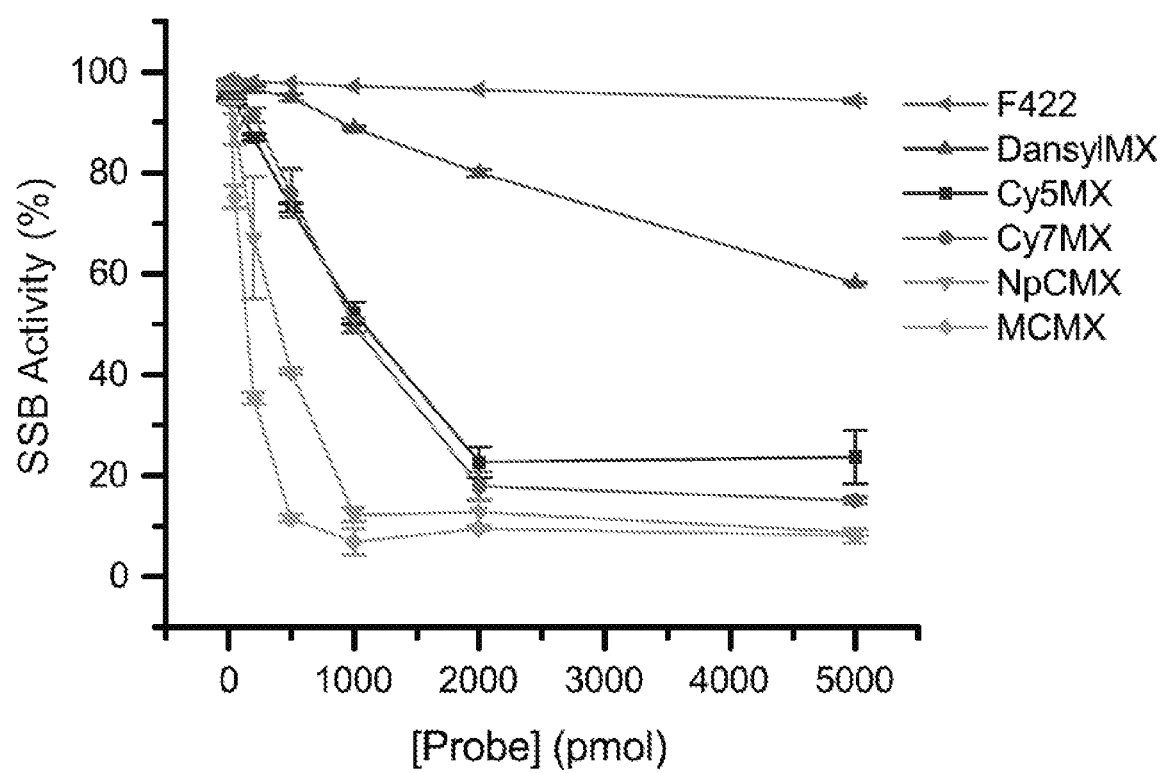
FIG. 1 illustrates SSB activity assay is used to compare the dose-response of AP site binding probes in 5 pmol of AP DNA. Mean and standard deviation of triplicate samples are shown for each concentration.

The single strand break (SSB) assay was proposed as a quick, facile tool to screen AP site binding probes. Therefore, the assay was performed on novel AP site binding probes described above and the commercially available AP site binding probe, F422. ACMX (ACMX) was not studied due to poor aqueous solubility. As shown in FIG. 1, the coumarin-based probes, MCMX and NpCMX, have similar dose-response profiles and are superior to the other probes assayed in dose-response and overall efficacy. The cyanine-based dyes, Cy5MX and Cy7MX, behaved similarly to each other and had acceptable dose-response and overall efficacy. The dansyl-based compound, DansylMX, and F422 showed unacceptable dose-response with an overall reduction in SSB activity of only ca. 60% and 90%, respectively. The reduced response of F422 and DansylMX may be due in part to the compounds being fairly electron rich near the aminooxy binding moiety. This could lead to a Coulombic repulsion with the DNA phosphate backbone.

Comparison to ARP and MX

Figure 2:
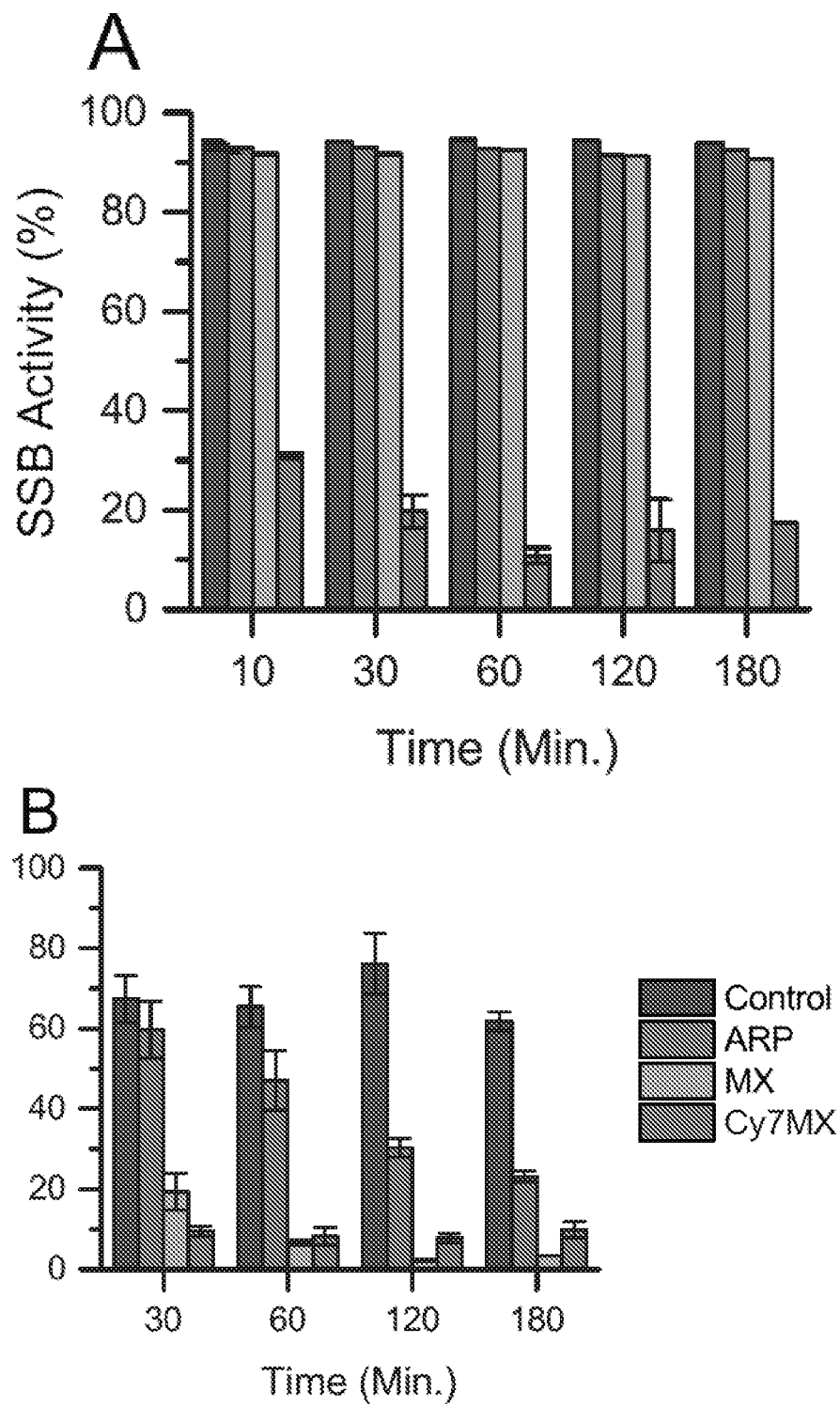
FIGS. 2(A-B) are a comparison of the SSB activity of U:A DNA (5 pmol) treated with UDG and Cy7MX, ARP, MX, or vehicle control as a function of incubation time prior to APE addition. (A) ARP (1 nmol), MX (1 nmol), and Cy7MX (1 nmol) with UDG (5 units) and APE (10 units); (B) ARP (200 nmol), MX (200 nmol), and Cy7MX (2 nmol) with UDG (5 units) and APE (1 unit). Bar represent the average of three samples and error bars are the standard deviation.

The SSB activity assay was used to compare new AP site binding probes to the previously developed ARP and MX. Using the same conditions as the control experiments (1 nmol probe, 5 pmol DNA, 1×APE), Cy7MX time course (before APE addition) showed remarkably superior AP site binding than ARP and MX. The decrease in SSB activity caused by ARP and MX was only slightly better than the vehicle control (FIG. 2A). To verify that this result is not an artifact of the assay, reaction conditions were modified to tease out ARP and MX time courses of binding. To this end, the molar equivalents of ARP and MX were increased 100-fold relative to Cy7MX. As the APE is expected to compete with the probes for the AP site, its concentration was decreased by a factor of ten as well. Using these modified conditions, MX showed a pronounced improvement in the time course and had an overall lower SSB activity than Cy7MX. ARP also showed a steady decrease in SSB activity over time, but never reached the SSB Activity (%) levels of Cy7MX or MX (FIG. 2B). From these data, one may conclude that the initial results were not an artifact of the assay and that Cy7MX shows superior AP site binding ability.

EXAMPLE 2

We developed a cyanine-based NIR probe, Cy7MX, that exhibits promising properties of binding to AP sites for detection and quantitation of DNA damage. This Example shows its physicochemical and binding properties for direct detection and quantification of AP sites.

Materials and Methods

Figure 3:
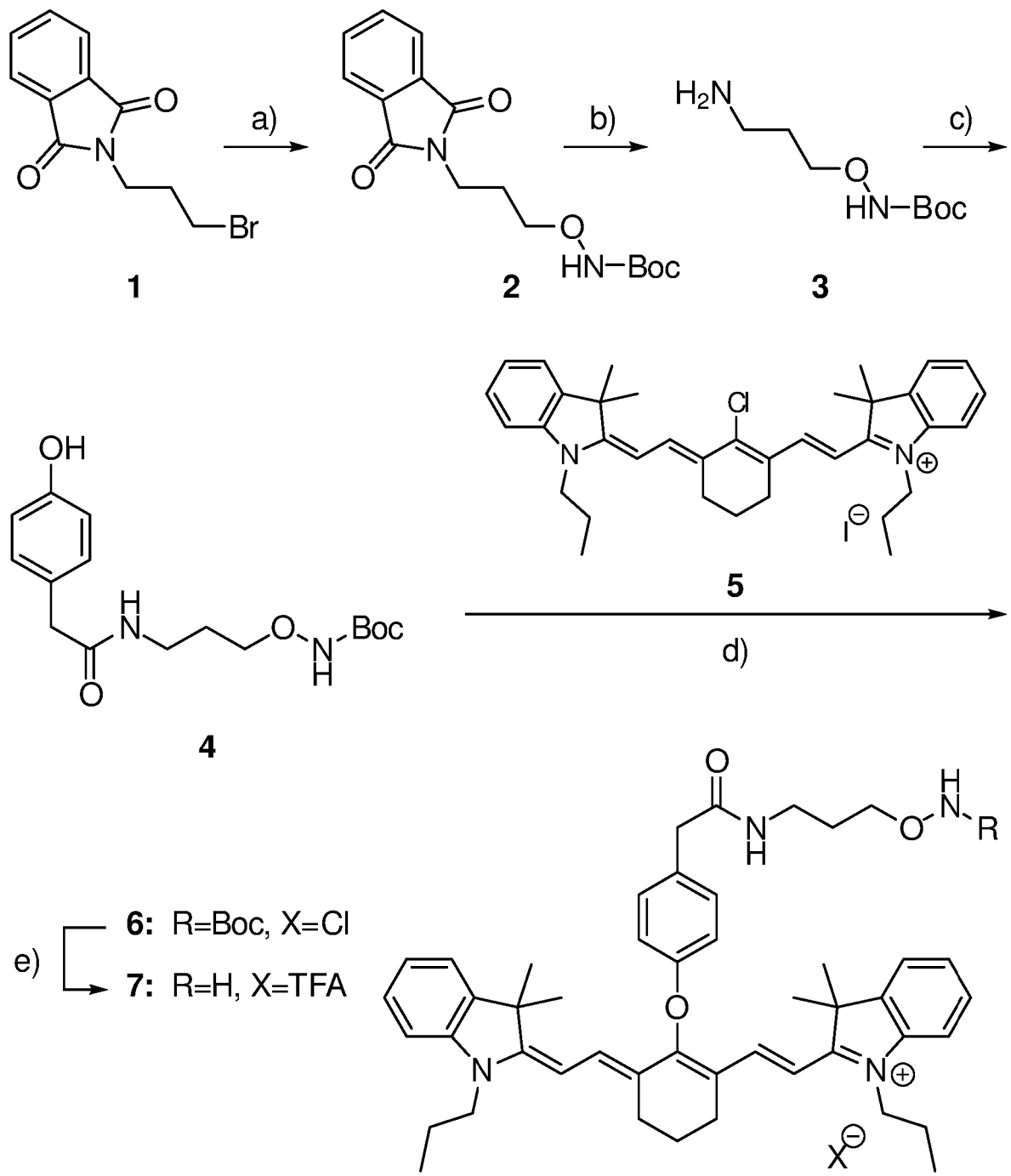
FIG. 3 illustrates synthesis of NIR probe Cy7MX (7). Reagents and conditions: a) N-Boc hydroxylamine, DBU, DCM, r.t., 68%; b) hydrazine monohydrate, MeOH, r.t., 88%; c) 4-hydroxyphenylacetic acid, EDC_HCl, HOBt_H2O, DMF, r.t. 80%; d) 5, NaH, DMF, r.t. 55%; and e) TFA, DCM, r.t. 71%.

Cy7MX was synthesized according to FIG. 3 tert-Butyl 3-(1,3-dioxoisoindolin-2-yl)propoxycarbamate (2) and tert-butyl 3-aminopropoxycarbamate (3) were prepared according to a literature procedure.

tert-butyl 3-(2-(4-hydroxyphenyl)acetamido)propoxycarbamate (4). 4-hydroxyphenylacetic acid (350 mg, 2.30 mmol, 1.05 eq), 3 (416 mg, 2.19 mmol, 1.00 eq), EDC HCl (629 mg, 3.28 mmol, 1.50 eq), and HOBt H$_2$O (503 mg, 3.28 mmol, 1.50 eq) were added to an oven-dried 50 mL round bottom flask fitted with a magnetic stir bar. The solids were dissolved in dry dimethylformamide (DMF, 20.0 mL) and the reaction was stirred at room temperature under argon for 24 h. The reaction was then diluted with water (100 mL) and ethyl acetate (EtOAc, 50 mL) and extracted. The aqueous layer was extracted twice more with EtOAc (25 mL). The combined organic layers were washed with water (2×40 mL) and brine (40 mL) then dried over MgSO$_4$, filtered, and concentrated. The crude residue was diluted in a trace amount of dichloromethane (DCM) and purified by silica gel chromatography with a mobile phase of pure DCM then gradually increasing polarity to 3:2 DCM/acetonitrile (MeCN). This product was then further purified by diluting it in EtOAc (25 mL) and washing with sat. NaHCO$_3$ (3×25 mL) and brine (1×25 mL). The organic layer was dried over MgSO4, filtered, and concentrated to afford pure 4 as a white solid (527 mg, 74%). $R_f$=0.23 (DCM/MeCN, 3:2); $^1$H NMR (400 MHz, CDCl3): δ=8.64 (br s, 1H), 8.21 (br s, 1H), 7.34 (br s, 1H), 7.07 (d, J=8.6 Hz, 2H), 6.74 (d, J=8.6 Hz; 2H), 3.84 (t, J=5.6 Hz, 2H), 3.46 (s, 2H), 3.35 (dt, J=6.0, 12 Hz, 2H), 1.71 (tt, J=6.0, 5.6 Hz, 2H), 1.47 (s, 9H); $^{13}$C NMR (100 MHz, CDCl$_3$): δ=172.8, 157.3, 155.7, 130.0, 125.7, 115.6, 81.6, 74.6, 42.4, 37.0, 28.0, 26.8.

2-((E)-2-((E)-3-((E)-2-(3,3-dimethyl-1-propylindolin-2-ylidene)ethylidene)-2-(4-(2,2-dimethyl-4,11-dioxo-3,6-dioxa-5,10-diazadodecan-12-yl)phenoxy)cyclohex-1-en-1-yl) vinyl)-3,3-dimethyl-1-propyl-3H-indol-1-ium chloride (6). NaH (14.1 mg, 0.588 mmol, 1.70 eq) and 4 (129 mg, 0.398 mmol, 1.15 eq) were added to an oven-dried 25 mL round bottom flask fitted with a magnetic stir bar. Dry DMF (3.0 mL) was added and the mixture was stirred under argon at room temperature for 30 min Meanwhile, IR 780 iodide (5, 230.1 mg, 0.345 mmol, 1.00 eq) was added to a 15 mL oven-dried heart-shaped flask fitted with a magnetic stir bar. DMF (5.0 mL) was added and 5 was stirred under argon at room temperature shielded from light. After 30 min, the solution of 5 was transferred to the NaH mixture via syringe. The heart-shaped flask was rinsed with dry DMF (4×2 mL) and the rinsate was added to the reaction mixture via syringe. The reaction was stirred at room temperature under argon in the dark for 5 h. The reaction was quenched with water (100 mL) and 10% NH$_4$Cl (aqueous, 50 mL). The aqueous mixture was extracted with DCM (1×100 mL, 1×25 mL) until the aqueous layer remained colorless. The combined organic layers were washed with water (2×50 mL) and brine (1×50 mL), dried over MgSO$_4$, filtered, and concentrated. The crude residue was diluted in a minimal amount of eluent and purified by silica gel chromatography with a mobile phase of 1:4:35 methanol (MeOH)/MeCN/DCM gradually increasing to 2:3:15 MeOH/MeCN/DCM. Impure fractions were concentrated and this chromatographic method was repeated one time. Pure fraction were combined and concentrated to afford 6 as an emerald solid (163 mg, 55%). $R_f$=0.15 (MeOH/MeCN/DCM, 1:3:16); $^1$H NMR (400 MHz, CDCl$_3$): δ=8.94 (br s, 1H), 8.78 (br t, J=5.6 Hz, 1H), 7.94 (d, J=14.0 Hz, 2H), 7.55 (d, J=8.4 Hz, 2H), 7.35-7.28 (m, 4H), 7.19 (dd, J=7.6, 7.2 Hz, 2H), 7.05 (d, J=8.0 Hz; 2H), 6.95 (d, J=8.8 Hz, 2H), 5.95 (d, J=14.0 Hz, 2H), 3.96 (t, J=7.2 Hz, 4H), 3.92 (t, J=5.6 Hz, 2H), 3.62 (s, 2H), 3.28 (dt, J=6.0, 6.0 Hz, 2H), 2.67 (dd, J=6.0, 5.6 Hz, 4H), 2.04 (dd, J=6.0, 5.6 Hz, 2H), 1.86 (tq, J=7.6, 7.2 Hz, 4H), 1.70 (tt, J=6.0, 5.6 Hz, 2H), 1.45 (s, 9H), 1.32 (s, 12H), 1.04 (t, J=7.6 Hz, 6H); $^{13}$C NMR (75 MHz, CDCl$_3$): δ=172.1, 171.6, 164.8, 158.3, 156.8, 142.3, 141.9, 140.8, 131.3, 131.2, 128.3, 124.9, 122.1, 121.7, 114.1, 110.2, 99.2, 80.3, 73.5, 48.9, 45.6, 42.3, 35.7, 28.1, 27.6, 27.2, 24.1, 20.9, 20.5, 11.4; MS-ESI: m/z [M]$^+$ calculated for $C_{52}H_{67}N_4O_5^+$: 827.51, found: 827.47.

2-((E)-2-((E)-2-(4-(2-((3-(aminooxy)propyl)amino)-2-oxoethyl)phenoxy)-3-((E)-2-(3,3-dimethyl-1-propylindolin-2-ylidene)ethylidene)cyclohex-1-en-1-yl)vinyl)-3,3-dimethyl-1-propyl-3H-indol-1-ium 2,2,2-trifluoroacetate (7). 6 (23.0 mg, 0.027 mmol, 1.00 eq) was dissolved in DCM (1.0 mL). TFA (1.0 mL, 13.0 mmol, 1.48 g/mL, 480 eq) was added and the solution immediately turned from dark green to dark red. The reaction was stirred for 1 h in the dark. The solvents were removed by rotary evaporation to afford pure 7 as an emerald green solid (16 mg, 71%). $R_f$=0.21 (MeOH/DCM, 1:9); $^1$H NMR (600 MHz, CDCl3): 8.93-8.20 (br s, 2H), 8.0-7.87 (br m, 3H), 7.37-7.26 (m, 6H), 7.19 (dd, J=7.8, 7.2 Hz, 2H), 7.02 (d, J=7.8 Hz, 2H), 6.97 (J=8.4 Hz, 2H), 5.93 (bs d, J=12.6 Hz, 2H), 4.09 (br s, 2H), 3.91 (bs t, J=7.2 Hz, 4H), 3.48 (br s, 2H), 3.23 (br m, 2H), 2.65 (br s, 4H), 2.02 (br m, 2H), 1.83 (tq, J=7.2, 7.2, 4H), 1.67 (br s, 2H), 1.30 (s, 12H), 1.02 (t, J=7.2 Hz, 6H); $^{13}$C NMR (150 MHz, CD$_2$Cl$_2$, −10° C.): δ=174.2, 172.4, 164.7, 161.0, 159.2, 142.5, 141.3, 131.2, 129.6, 128.7, 125.3, 122.6, 122.1, 115.1, 110.7, 99.8, 72.2, 49.3, 46.0, 41.9, 35.8, 27.7, 27.6, 24.4, 21.3, 20.9, 11.7; UV/Vis (EtOH): $\lambda_{max}$ (ε)=705 nm (29200 mol$^{-1}$cm$^{-1}$), 770 nm (127000 mol$^{-1}$cm$^{-1}$); HRMS-ESI: m/z [M]$^+$ calculated for $C_{47}H_{59}N_4O_3^+$: 727.4587, found: 727.4615.

Fluorescence quantum yield measurements. Fluorescent quantum yields determined by a comparative method to an indocyanine green (ICG) standard (F=0.132 in EtOH) with refractive index correction according to the equation:

$$\Phi = \Phi_R \left(\frac{m}{m_R}\right)\left(\frac{n^2}{n_{R^2}}\right)$$

where F is the quantum yield; m is the slope of the integrated fluorescence intensity as a function of absorbance maxima; n is the refractive index of the solvent (EtOH, 1.3611; MeCN, 1.3442; H$_2$O, 1.333; and CHCl3, 1.4459); and R is the reference sample, ICG in EtOH. Data were collected in a quartz cuvette with a 1 cm path length. Absorbance maxima for each sample were kept at or below 0.2 absorbance units to avoid inner filter effects. Fluorophores were excited at 700 nm and emission spectra integrated from 705 to 1000 nm. Solvents used were spectroscopic grade ethanol and HPLC grade acetonitrile, HPLC grade chloroform, and HPLC grade water. For the water solution, Cy7MX was first dissolved in MeCN and diluted at least 200 fold.

SSB Activity Assay

General Procedures

SSB activity assays were performed on a 40-mer duplex DNA synthesized by IDT with the sequence:

5'-[HEX]TCCTGGGTGACAAAGCXAAACACTGTCTCCAAAAAAATT; (SEQ ID NO: 1)

3'-AGGACCCACTGTTTCGYTTTGTGACAGAGGTTTTTTTTAA; (SEQ ID NO: 2)

where X=uracil or thymine and Y=adenine, cytosine, guanine, or thymine. DNA was diluted in dH$_2$O to 500 nM and 5 pmol (10 μL) aliquots were used in each sample. APE (10,000 Units/mL) and UDG (5,000 Units/mL) enzymes and corresponding buffers were purchased from New England BioLabs. UDG storage buffer (10 mM Tris-HCl, 50 mM KCl, 1 mM DTT, 0.1 mM EDTA, 0.1 mg/ml BSA, 50% Glycerol, pH 7.4) and APE storage buffer (10 mM Tris-HCl, 50 mM NaCl, 1 mM DTT, 0.05 mM EDTA, 200 μg/ml BSA, 50% Glycerol, pH 8.0) were prepared according to formulation provided by New England BioLabs to use as blanks, where necessary. The enzymes were not heat inactivated as this was observed to give rise to artifacts. Reaction products were resolved on denaturing 20% polyacrylamide gels (5.3 g urea, 5.0 mL 40% acrylamide, 2.3 mL 5×TBE buffer, 200 μL 10% APS, and 20 μL TEMED). 5×TBE buffer was prepared with tris base (54 g), boric acid (27.5 g), and EDTA (4.65 g) diluted to 1 in water. Loading dye was prepared (300 μL 10M NaOH, 20 mg bromophenol blue, 9.7 mL formamide) and was added to samples (~5 μL) to aid loading and visualization of gel progression. Gel were developed at 300 V for 45 min in the dark and imaged based on the DNA tag on Typhoon Trio+Variable Mode Imager (Amersham Biosciences) in fluorescent mode with 532 nm excitation and 555 nm emission with a 20 nm band pass, PMT set to 400, and pixel size resolution of 100 μm. Gel data were analyzed using ImageQuant software (Amersham Biosciences). DNA cutting was defined as the fluorescence intensity of the 16-mer strand divided by the sum of the fluorescence intensities of the 16- and 40-mer strands. The fluorescence of Cy7MX on the gels was imaged on a Syngene scanner. The image in FIG. 5 was modified in Adobe Photoshop from the original in the following ways: 1) green and red photo filters were applied to corresponding monochrome images for clarity; 2) the HEX image from the Typhoon scanner (green) was scaled to same size as the Cy7MX image from the Syngene G:Box Chemi XT4 scanner (red) to account for different image resolutions and to facilitate co-registration; 3) a levels adjustment filter was applied uniformly to the red image to increase signal-to-noise and improve contrast; 4) the images were cropped to the region of interest; and 5) a "screen" blending mode was applied to the green layer to allow the red layer to be observed beneath it without changing opacity settings. No quantitative measurements were taken from the modified images.

SSB Activity Assay Control Reactions

Samples were prepared in triplicate. To a 0.6 mL Eppendorf tube were added dsDNA (10 μL, 5 pmol), 10×UDG reaction buffer (1 μL), 10×APE reaction buffer (1 μL), H$_2$O (5 μL), Cy7MX or vehicle control (2 μL, 1 nmol; vehicle=1% DMSO in H$_2$O), and UDG or UDG storage buffer (1 μL, 5 Units). Samples were incubated at 37° C. for 1 h in the dark. Then APE (1 μL, 10 Units) or APE storage buffer (1 μL) was added and samples were again incubated at 37° C. for 1 h in the dark.

SSB Activity Assay with Base Pairs

Reaction samples were prepared in triplicate; control samples were prepared singly. To a 0.6 mL Eppendorf tube were added dsDNA (10 μL, 5 pmol), 10×UDG reaction buffer (1 μL), 10×APE reaction buffer (1 μL), H$_2$O (5 μL), Cy7MX or vehicle control (2 μL, 1 nmol; vehicle=1% DMSO in H$_2$O), and UDG (1 μL, 5 Units). Samples were incubated at 37° C. for 10 min, 30 min, 1 h, 2 h, or 3 h in the dark. Then APE (1 μL, 10 Units) was added and samples were again incubated at 37° C. for 1 h in the dark.

SSB Activity Assay UDG Inhibition

Method UDG (10 min)+Cy7MX: All samples were prepared in triplicate. To a 0.6 mL Eppendorf tube were added dsDNA (U:A, 10 μL, 5 pmol), 10×UDG reaction buffer (1 μL), 10×APE reaction buffer (1 μL), H$_2$O (5 μL), and UDG (1 μL, 5 Units). Samples were incubated at 37° C. for 10 min Cy7MX (2 μL, 1 nmol) was added and the samples were incubated at 37° C. in the dark for 2 min, 10 min, 30 min, 60 min, or 180 min. Then APE (1 μL, 10 Units) was added and samples were again incubated at 37° C. for 1 h in the dark.

Method UDG+Cy7MX: All samples were prepared in triplicate. To a 0.6 mL Eppendorf tube were added dsDNA (U:A, 10 μL, 5 pmol), 10×UDG reaction buffer (1 μL), 10×APE reaction buffer (1 μL), H$_2$O (5 μL), Cy7MX (2 μL, 1 nmol), and UDG (1 μL, 5 Units). Samples were incubated at 37° C. in the dark for 2 min, 10 min, 30 min, 60 min, or 180 min. Then APE (1 μL, 10 Units) was added and samples were again incubated at 37° C. for 1 h in the dark.

Method UDG: As in method UDG+Cy7MX except substitute DMSO (2 μL) for Cy7MX.

SSB Activity Assay APE Inhibition

APE (2 μL, 20 Units) and Cy7MX or vehicle (4 μL, 2 nmol; vehicle=1% DMSO in H$_2$O) were mixed and incubated at 37° C. for 0.5 h, 1 h, 1.5 h, 2 h, or 3 h in the dark. Meanwhile, five samples of each DNA reaction were prepared. To a 0.6 mL Eppendorf tube were added dsDNA (U:A, 10 μL, 5 pmol), 10×UDG reaction buffer (1 μL), 10×APE reaction buffer (1 μL), H$_2$O (5 μL), and UDG (1 μL, 5 Units). Samples were incubated at 37° C. for 1 h in the dark. Then APE/Cy7MX mixtures (3 μL) were added and samples were again incubated at 37° C. for 1 h in the dark.

SSB Activity Assay ARP and MX Comparison

Method 1: Stock solutions of probes were prepared at 50 mM. Cy7MX was dissolved in DMSO, MX was dissolved in H$_2$O (pH 7), and ARP was dissolved in H$_2$O. Stock solutions were further diluted with H$_2$O to 500 μM. Water was used as a blank. All samples were prepared in triplicate. To a 0.6 mL Eppendorf tube were added dsDNA (U:A, 10 μL, 5 pmol), 10×UDG reaction buffer (1 μL), 10×APE reaction buffer (1 μL), H$_2$O (5 μL), probe or blank (2 μL, 1 nmol), and UDG (1 μL, 5 Units). Samples were incubated at 37° C. for 10 min, 30 min, 1 h, 2 h, or 3 h in the dark. Then APE (1 μL, 10 Units) was added and samples were again incubated at 37° C. for 1 h in the dark.

Method 2: Stock Solutions of 50 mM ARP and MX were Used without Further Dilution.

Cy7MX was diluted to 500 μM. APE was diluted 10-fold in APE storage buffer. Water was used as a blank. All samples were prepared in triplicate. To a 0.6 mL Eppendorf tube were added dsDNA (U:A, 10 μL, 5 pmol), 10×UDG reaction buffer (1 μL), 10×APE reaction buffer (1 μL), H$_2$O (5 μL), probe or blank (4 μL; 2 nmol Cy7MX, 200 nmol ARP and MX), and UDG (1 μL, 5 Units). Samples were incubated at 37° C. for 10 min, 30 min, 1 h, 2 h, or 3 h in the dark. Then APE (1 μL, 1 Unit) was added and samples were again incubated at 37° C. for 1 h in the dark.

Heat/Acid Treatment of Calf Thymus DNA

Calf thymus DNA was purchased from Sigma and was reconstituted overnight at 4° C. in either $H_2O$ or 500 mM MX (to eliminate basal AP sites) with gentle shaking (1.5 mL water or solution per 5 mg DNA). For samples reconstituted in MX solution, an ethanol precipitation was performed twice before heat and acid treatment (vide infra) then reconstituted in water. The DNA-water solution was aliquoted to 1.5 mL Eppendorf tubes (360 µL) and 10× Citrate buffer (1M NaCl, 100 µM monosodium phosphate, 100 µM monosodium citrate, pH 5.0) was added to a final concentration of 1×. For t=0 min samples, ice-cold 100% EtOH (1.0 mL) was added immediately and the Eppendorf tubes stored at −20° C. Other samples were placed in a 70° C. heating block for 15-90 minutes in 15-minute increments. Samples were removed from heat, precipitated in ice-cold 100% EtOH (1.0 mL), and then chilled at −20° C. for at least 20 minutes. Samples were centrifuged at 12,000×G for 10 min at 4° C. The supernatant was discarded. The process was repeated once beginning with the addition of EtOH (1.0 mL). The DNA pellet was dissolved in 700 µL $H_2O$ or TE buffer. Aliquots of 80 µL were put in 1.5 mL Eppendorf tubes. Any samples not used immediately were stored at −80° C.

Genomic DNA Time Course of Cy7MX Binding

A 100 mM stock solution of Cy7MX in DMSO was diluted to 25 µM in $H_2O$. Heat/acid treated DNA (t=45 min, 80 µL) were warmed to 37° C. In triplicate, Cy7MX (20 µL) was added to the DNA pipetting up and down to mix. Samples were kept at 37° C. in the dark for the following incubation times (min): 0.5, 1, 2, 5, 10, 15, 30, and 60. Immediately after the incubation time, ice-cold EtOH (1.0 mL) was added. Samples were quickly inverted to mix then stored in the dark at −78° C. in a dry ice-EtOH bath. The DNA was then purified by EtOH precipitation three times as described in the heat/acid treatment of genomic DNA. The purified DNA pellets were suspended in 150 µL $H_2O$. Aliquots (125 µL) of the samples were added to a black, clear-bottom 96 well plate (Corning) and analyzed with 750 nm excitation and 800 nm emission. Fluorescence was adjusted to DNA concentration.

Genomic DNA Dose-Response of Cy7MX

Samples were prepared in triplicate. To 90 µL aliquots of heat/acid treated DNA (t=20 min), was added Cy7MX (10 µL) in the following quantities (pmol): 0, 0.05, 0.5, 5, 50, 250, 500, 2500, 5000, 12500, 25000, and 50000. Solutions were kept in the dark. Samples were incubated for 1 h at 37° C. in the dark. Ice-cold EtOH (1.0 mL) was added and the DNA was purified by EtOH precipitation three times as described in the heat/acid treatment of genomic DNA section. DNA was dissolved in 120 µL $H_2O$. Aliquots (100 µL) of the samples were added to a black, clear-bottom 96 well plate (Corning) and analyzed with 750 nm excitation and 800 nm emission. Fluorescence was adjusted to 300 µg/mL DNA concentration.

MX and Cy7MX Genomic DNA Competition Assay

Solutions of MX and Cy7MX were prepared in $H_2O$ varying [MX] from 0-1.9 M and maintaining at 25 µM. CAUTION: Solutions were kept vigorously in the dark as MX was observed to decompose Cy7MX rapidly (on the minute time scale) in the presence of light. The ratios of MX:Cy7MX used in this study were: 0, 0.01, 0.1, 0.5, 1, 5, 10, 50, 100, 250, 500, 1000, 2500, 5000, 10000, 25000, 50000, and 75000. For visual clarity, the data for the ratios 0.01, 0.1, 5, 10, 50, 250, and 500 were omitted as this did not affect the analysis. The following samples were prepared in triplicate: 20 µL of MX/Cy7MX solution was added to 80 µL aliquots of heat/acid treated DNA (t=45 min). Samples were incubated for 1 h at 37° C. in the dark. Ice-cold EtOH (1.0 mL) was added and the DNA was purified by EtOH precipitation three times as described in the heat/acid treatment of genomic DNA section. DNA was dissolved in 150 µL $H_2O$. Aliquots (125 µL) of the samples were added to a black, clear-bottom 96 well plate (Corning) and analyzed with 750 nm excitation and 800 nm emission. Fluorescence was adjusted to DNA concentration.

ARP and Cy7MX Genomic DNA Competition Assay

As before (section 2.3.2) except solutions of ARP and Cy7MX were prepared in $H_2O$ varying [ARP] from 0-75 mM and maintaining at 1 µM. The ratios of ARP:Cy7MX used in this study were: 0, 0.1, 1, 10, 100, 500, 1000, 5000, 10000, 25000, 50000, and 75000.

MX and Cy7MX Genomic DNA Blocking Assay

To 80 µL aliquots of DNA was added either 10 µL of MX (500 mM, pH 7) or vehicle control (500 mM NaCl). TE buffer was used as a-DNA control. Samples were incubated at 37° C. for 30 min. Then, either 10 µL of Cy7MX (500 µM) or 10 µL of 1% DMSO in water was added to samples. Samples were incubated at 37° C. in the dark for 1 h before DNA was purified by ethanol precipitation three times as described in the heat/acid treatment of genomic DNA. The purified DNA pellets were dissolved in 150 µL $H_2O$. Aliquots (125 µL) of the samples were added to a black, clear-bottom 96 well plate (Corning) and analyzed with 700 nm excitation and 790 nm emission. Fluorescence was adjusted to DNA concentration.

AP Site Evaluation in FUDR Treated Cells

Preparation of KD and WT Cells

DLD1 cells (ATCC #CCL-221) were obtained from the laboratory of Sanford Markowitz at Case Western Reserve University. UDG directed shRNA clones and scrambled targeted control shRNA clones were purchased from Sigma-Aldrich. According to manufacturer's instructions from Lipofectamine 2000 (Invitrogen), HEK293 cells were transfected to produce lentiviral particles that were used to infect DLD1 cells. Forty-eight hours after transfection, DLD1 cells were diluted for passage and selected with puromycin. The UDG knockdown levels were verified by RT-PCR and Western blot analysis.

FUDR Treatment, Isolation, and Cy7MX Analysis of DLD1 DNA

DLD1 shUDG (KD) or shControl (WT) cells were plated in Falcon brand 100×20 mm cell culture dishes in 10 mL medium (DMEM supplemented with 10% heat inactivated FBS, penicillin/streptomycin, and nonessential amino acids) and incubated at least 16 h at 37° C. and 5% $CO_2$ to ensure adhesion. To allow for cell proliferation, the following approximate numbers of cells were plated for each time point given in parenthesis: 4 million (24 h), 1 million (48 h), and 0.3 million (72 h). Two mL of medium were removed from each plate and replaced with 2 mL of FUDR solution at a final concentration of 0, 10, 200, or 1000 nM in 10 mL. For each time point, six plates of each FUDR treatment group were prepared for each cell line. Cells were incubated at 37° C. and 5% $CO_2$ with continuous FUDR exposure for 24, 48, or 72 h.

At the time points, the media was removed and cells were rinsed with PBS. Cells were dissociated with 0.25% trypsin (1 mL) and transferred to 15 mL conical tubes in 5 mL PBS. The conical tubes were centrifuged at 1,700 rpm to pellet the cells. The supernatant was removed and discarded. Cell pellets were dissolved in TE buffer (2 mL) then treated with 10% SDS (240 µL) and RNase A (10 µL, 20 mg/mL purchased from Invitrogen) for at least 15 minutes at 37° C.

Then, proteinase K (10 μL, 20 mg/mL purchased from Invitrogen) was added and cell lysates were incubated for a least 15 minutes at 37° C. Cell lysates were transferred to Phase Lock Gel Light 15 mL conical tubes purchased from SPrime. Saturated phenol (2 mL, pH 6.6) was added to the cell lysates and the mixture was shaken vigorously. Chloroform (0.5 mL) was then added and the cell lysate mixtures shaken vigorously. The organic and aqueous phases were separated by centrifuging the gel tubes at 2,000 rpm for 10 minutes. After a second round of phenol-chloroform addition and centrifugation, pure chloroform (2 mL) was added to the cell lysates, shaken, and centrifuged at 2,000 rpm for 10 minutes. The aqueous layer containing the isolated DNA was decanted into a clean 15 mL conical tube and precipitated with 100% EtOH (5 mL) and 3M sodium acetate (100 μL) by gentle rocking at 4° C. for at least 30 minutes. DNA was isolated by centrifuging at 3,000 rpm for 10 minutes. The DNA pellets were washed once with 70% EtOH (1.5 mL) and centrifuged at 3,000 rpm for 10 minutes.

Pure DNA pellets were dissolved in 200 μL 1×UDG buffer. Samples were treated in triplicate with either UDG (1 μL, 5 units) or UDG storage buffer (see SSB activity assay procedures) and incubated at 37° C. for 1 h. After UDG incubation, 10 μL of each solution was removed and set aside for analysis with the ARP assay (Dojindo). A solution of Cy7MX (10 μL, final=25 μM) was added to each sample, keeping the stock solution and all treated samples vigorously in the dark until the final analysis. Samples were incubated with Cy7MX for 1 h at 37° C. in the dark. After incubation, ice cold 100% EtOH (1 mL) and 3M sodium acetate (5 μL) were added to each sample. Samples were inverted to mix then chilled for at least 20 minutes at −20° C. Samples were centrifuged at 12,000 G and 4° C. for 10 minutes. The supernatant was discarded. This EtOH wash was repeated twice with 70% EtOH (1 mL) and no sodium acetate. DNA pellets were dissolved in $H_2O$ (minimum 150 μL). DNA concentrations were measured and adjusted to a maximum of 300 μg/mL. Aliquots (125 μL) of the samples were added to a black, clear-bottom 96 well plate (Corning) and analyzed with 760 nm excitation and emission scan of 790-847 nm with a 3 nm step size. Integrated fluorescence intensities were adjusted to DNA concentration and normalized to the FUDR untreated KD+UDG sample.

ARP Analysis of FUDR Treated DLD1 DNA

DNA aliquots (10 μL) from above were diluted in TE buffer (10 μL). DNA concentrations were measured on a Nanodrop 1000 and adjusted to 100 μg/mL in TE buffer. Samples were prepared for ARP analysis using the ARP DNA Damage Quantification Kit (Dojindo #DK02-12). Samples were prepared and analyzed according to the manufacturer's instructions.

MMS Treatment, Isolation, and Cy7MX Analysis of DLD1 DNA

DLD1 shControl (WT) cells at a density of 3 million cells per dish were plated in Falcon brand 100×20 mm cell culture dishes in 10 mL medium (DMEM supplemented with 10% heat inactivated FBS, penicillin/streptomycin, and nonessential amino acids) and incubated 16 h at 37° C. and 5% $CO_2$ to ensure adhesion. Solutions of MMS were prepared in serum free DMEM medium at concentrations of 0.05, 0.25, 1, 4, and 10 mM. Medium was removed from the cells and replaced with the MMS or a serum free medium vehicle. Three plates were prepared per treatment group. Cells were incubated at 37° C. and 5% $CO_2$ with continuous MMS exposure for 3 h. At the time points, cells were collected and DNA isolated as described above (Treatment of DLD1 cells with FUDR).

Pure DNA pellets were suspended in 190 μL water. A solution of Cy7MX (10 μL, final=25 μM) was added to each sample, keeping the stock solution and all treated samples vigorously in the dark until the final analysis. Samples were incubated with Cy7MX for 1 h at 37° C. in the dark. After incubation, DNA was purified and analyzed as described above.

Results

Chemistry

Synthesis of Cy7MX. The synthetic route used to prepare the fluorescent probe, Cy7MX, is shown in FIG. 3. Compound 3 was synthesized using a modified, two-step procedure, which afforded a higher yield than previously reported. Briefly, compound 2 was prepared by a substitution reaction between N-(3-bromopropyl)phthalimide (1) and N-Boc-hydroxylamine in the presence of 1,8-diazabicyclo[5.4.0]undec-7-ene (DBU). The phthalimide protecting group was removed with hydrazine to afford 3. We observed that the yield of this reaction nearly doubled (49% vs. 88%) when the reaction mixture was diluted from 400 mM to 50 mM, possibly by reducing intermolecular polymerization. An N-(3-dimethylaminopropyl)-N0-ethylcarbodiimide hydrochloride (EDC) and 1-hydroxybenzotriazole hydrate (HOBt) mediated amide coupling reaction between 3 and hydroxyphenylacetic acid gave 4 in excellent yield. The commercially available cyanine dye, 5, was then reacted with 4 in the presence of NaH to give the substitution product, 6. A trifluoroacetic acid (TFA) mediated Boc deprotection of 6 afforded Cy7MX with a 19% overall yield.

Fluorescence Characterization of Cy7MX

Figure 4:
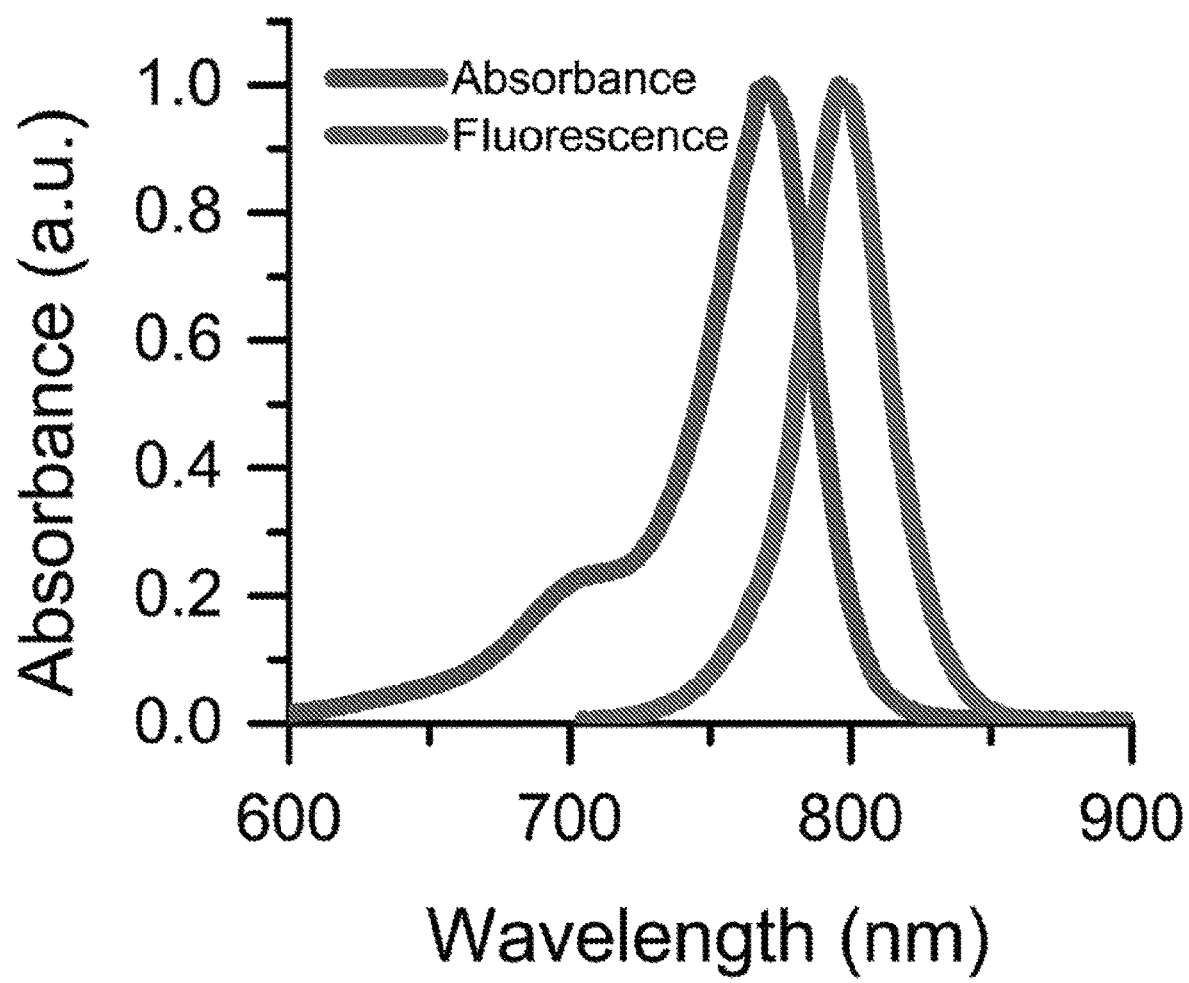
FIG. 4 illustrates the normalized absorbance and fluorescence emission spectra for Cy7MX. Absorbance and fluorescence measured in EtOH.

The absorption and fluorescence properties of Cy7MX were then evaluated in relatively nonpolar ($CHCl_3$), polar aprotic (MeCN), and polar protic (EtOH and $H_2O$) solvents. No solvatochromic shifts were observed between the spectra in these solvents (FIG. 4) with the absorption maximum near 770 nm and emission maximum near 790 nm. Likewise, the quantum yields of Cy7MX in these solvents compare favorably with other cyanine dyes (Table 3).

TABLE 3

Comparison of the optical properties of Cy7MX in various solvents

| Solvent | ε (M−1cm−1) | λabs (nm) | λem (nm) | Φ (%) |
|---|---|---|---|---|
| $H_2O$ | 140,000 | 767 | 790 | 6.6 |
| EtOH | 127,000 | 770 | 796 | 39.3 |
| MeCN | 154,000 | 767 | 789 | 48.7 |
| $CHCl_3$ | Not determined | 770 | 791 | 38.2 |

SSB Assay to Evaluate AP Site Binding Ability

After evaluating the fluorescence properties of Cy7MX, its ability to bind to AP sites was examined We developed an assay using a fluorescently tagged dsDNA (double stranded DNA) oligonucleotide with a single uracil incorporated into the labeled strand (FIG. 5A). A green emitting hexachlorofluorescein (HEX) label was incorporated at the 5' end of the sense strand in order to avoid overlapping with the NIR fluorecent emission of Cy7MX. We expected that treatment of this oligomer with UDG would generate an AP site and subsequent treatment with APE would produce a single strand break. This break could be visualized by denaturing gel electrophoresis to reveal a 16mer single strand DNA (ssDNA) instead of the 40mer parent (FIG. 5B). However, we hypothesized that if the oligomer were treated with Cy7MX prior to APE treatment, the covalent Cy7MX:AP site lesion would not be recognized by APE as a substrate and no SSB would form.

To validate the assay, we first ran a series of controls. As the U:A base pair is most likely to occur when dUTP is incorporated in place of dTTP, we used this as our primary substrate. As expected, we observed no SSB activity when UDG and/or APE were omitted or when a T:A substrate oligomer was used. Likewise, U:A-paired DNA treated with Cy7MX alone (no enzymes) did not lead to a SSB, indicating that the probe itself has no SSB activity. Instead, when the oligomer was treated with both UDG and APE in the absence of Cy7MX, we saw nearly quantitative breaking (FIGS. 5B and 5C). When U:A-paired DNA was treated with Cy7MX together with UDG and APE, the SSB activity was reduced. When the NIR channel emission was overlaid with the green channel (HEX) emission, colocalization is observed only in 40mer strands treated with Cy7MX and both enzymes but not in DNA treated with Cy7MX alone, indicating that Cy7MX is binding to the AP site and not elsewhere along the DNA (FIG. 5B). The base opposite to the uracil does not appear to affect the binding of Cy7MX to the AP site (FIG. 5D and FIG. 6).

Figure 7:
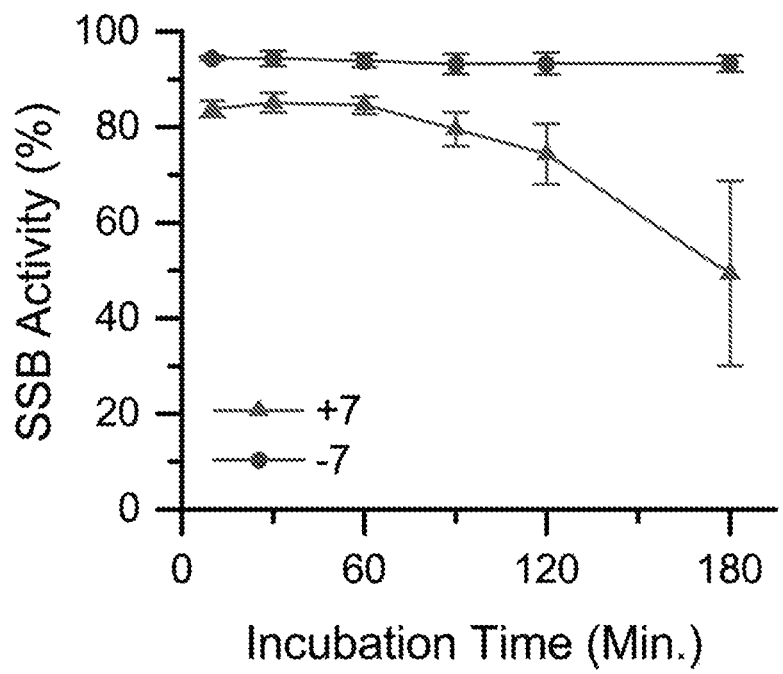
FIG. 7 illustrates the evaluation of APE inhibition by Cy7MX. APE shows mild inhibition by Cy7MX when incubated together before addition of AP-DNA. The SSB activity assay used 60 min APE incubation after treatment of AP-DNA with Cy7MX, which here shows no detectable inhibition. APE is inhibited about 50% after 3 h incubation.

We determined if Cy7MX could inhibit the activity of the enzymes and thereby complicate the results on the assay. While the order of reagent addition in the assay may be structured to avoid enzyme inhibition, Cy7MX is envisioned as an imaging agent in living cells where the enzymes are constantly present. To test the possible inhibition of Cy7MX towards APE, the probe and enzyme were incubated together for a variable period of time then incubated for a fixed period of time with AP DNA (U:A DNA pretreated with UDG). If the two species were only competing for substrate, then the extent of cutting observed would be independent of the APE+Cy7MX incubation time. Conversely, if Cy7MX inhibits the action of APE, then the extent of cutting would vary as a function of APE+Cy7MX incubation time. In either case, some baseline reduction in cutting was expected as Cy7MX and APE competed for substrate. As shown in FIG. 7, there was a change in cutting as APE and Cy7MX incubation time increased, indicating that Cy7MX did have inhibitory effects on APE. However, this effect was only observed after 60 minutes. Thus, the one hour incubation of APE in the cutting assay is not expected to be negatively impacted by the presence of Cy7MX. An additional APE inhibition study using a tetrahydrofuran (THF) base in place of the AP site were conducted and suggest moderate inhibition of APE by Cy7MX for this substrate.

Likewise, the potential of Cy7MX to inhibit UDG, either through direct interaction with the enzyme or by binding to DNA and blocking the uracil substrate, was tested. To accomplish this, U:A DNA was incubated with UDG for a fixed time prior to addition of Cy7MX (FIG. 8, UDG (10 min)+Cy7MX). In this case, Cy7MX could not interfere with the activity of UDG. These data were compared to samples where U:A DNA was treated simultaneously with Cy7MX and UDG (FIG. 8, UDG+Cy7MX). No significant difference in cutting activity was observed between these conditions indicating that Cy7MX does not inhibit UDG activity.

Comparison of Cy7MX to MX and ARP in SSB Assay

We then compared Cy7MX to two AP sitebinding probes that have previously been developed, ARP and MX. Under the same assay conditions of the control experiments (1 nmol probe, 5 pmol DNA, 1×APE), we observed that Cy7MX rapidly blocked the SSB activity of APE while ARP and MX failed to block almost any relative to the control (FIG. 9A). To ensure that this dramatic difference was not an artifact of the assay, we determined conditions under which ARP and MX could be observed to block APE activity. Therefore, we increased the amounts of ARP and MX (100× relative to Cy7MX) and decreased the amount of APE (0.1×), as the enzyme and probes compete for the AP site substrate. Under these conditions, we observed that ARP and MX were able to block the SSB activity of APE (FIG. 9B). Thus, we concluded that Cy7MX binds to AP sites more potently than ARP and MX do in the reaction conditions employed here.

Characterization of AP Site Binding in Calf Thymus DNA

Having established the ability of Cy7MX to recognize and bind AP sites, we also demonstrated that the fluorescence is proportional to the quantity of lesions present in DNA. Following a procedure described by Lindahl and Nyberg, calf thymus DNA was heated at 70° C. in citrate buffer (pH 5.0). This treatment generates a number of AP sites that increases linearly with time. This DNA was incubated with Cy7MX and subsequently purified by ethanol precipitation to remove unreacted Cy7MX. A linear relationship was observed between the fluorescence intensity of Cy7MX and DNA heat/acid treatment time, reflecting the increase of AP sites and indicating that Cy7MX can report on the quantity of AP sites in a genomic sample (FIG. 10). When DNA was pretreated with a large excess of MX (1000×), the fluorescent intensity was significantly reduced, suggesting that MX was able to block the binding of Cy7MX. These studies indicated that Cy7MX binds selectively to AP sites in DNA.

The time course of heat/acid treated DNA was measured to determine directly the rate of Cy7MX binding to AP sites. AP DNA and Cy7MX were incubated at 37° C. for a variable time then quickly precipitated with purified cold ethanol. The fluorescence was measured and from these data (FIG. 11), we calculated reaction half-life ($t\frac{1}{2}$=2.6 min) and observed the reaction was complete after approximately 10 min. In addition, a dose-response curve was generated by varying the quantity of Cy7MX and maintaining a constant quantity of AP DNA. The fluorescence was measured and from these data (FIG. 12), we calculated ED50=2.3 nmol.

Comparison of Cy7MX to MX and ARP Calf Thymus Binding

To verify the results of the SSB assay (FIG. 9), we performed a competition assay between Cy7MX and either ARP or MX. Keeping the molar concentration of Cy7MX constant, the molar concentration of ARP/MX was adjusted so that the MX or ARP: Cy7MX ratio ranged from 0.01 to 75,000. These solutions of MX or ARP/Cy7MX were added to the DNA for 1 h at 37° C. Fluorescence was measured following ethanol precipitation to remove unbound probes. These results (FIG. 13) indicate that the ED50 of Cy7MX was at 3000× excess of MX and 2600× excess of ARP. We presume the increased hydrophobicity of Cy7MX over MX and ARP as well as a mild Coulombic interaction may favor an association of Cy7MX with DNA over bulk solution and contribute to this drastic difference.

Detection of AP Sites in Colon Cancer Cells

Finally, we sought to demonstrate that Cy7MX can report on physiologically relevant quantities of AP sites. To this end, we prepared a shRNA UDG knockdown in the DLD1 colon cancer cell line. DLD1 cells (ATCC #CCL-221) were obtained from the laboratory of Sanford Markowitz at Case Western Reserve University. This knockdown cell line (KD) and its matched, shRNA scrambled control line (WT) were treated with the antimetabolite, 5-fluoro-20-deoxyuridine (FUDR or floxuridine), for 24, 48, and 72 hours. An antimetabolite like aminopterin, FUDR is used clinically to treat colon cancer. FUDR induces DNA damage in two ways: first, by inhibiting thymidylate synthas and decreasing the thymine pool leading to uracil misincorporation; and second, by cellular activation then direct incorporation of 5-fluorodeoxyuracil (FUra) into the DNA chain. Both uracil and FUra lesions are repaired by UDG. Therefore, we hypothesized that following FUDR treatment the KD would accumulate lesions while the WT would repair them effectively. Isolation of DNA from a cell lysate followed by in vitro treatment with purified UDG enzyme (or vehicle control) and Cy7MX would allow us to visualize DNA damage and repair in the DLD1 cell line. Fluorescence measurements of Cy7MX revealed that the KD cells did accumulate damage that was repaired in vitro while WT cell lines did not (FIG. 14). After 72 h of continuous FUDR exposure, the UDG treated KD showed nearly a 9-fold increase in fluorescence intensity, indicating that Cy7MX can report on physiologically relevant concentrations of AP sites. Additionally, this experiment demonstrates a tool that can be used to quantify uracil lesions in DNA. This could be useful to understand the mechanism and response of drug treatment in cancer cells.

Aliquots of each sample were set aside following exogenous UDG treatment but before addition of Cy7MX. These samples were analyzed by the ARP-based DNA Damage Quantification Kit by Dojindo. The results of this assay showed a larger background and lower sensitivity than compound Cy7MX, but confirmed the trends observed in FIG. 13. One advantage of Cy7MX over ARP is that Cy7MX contains both the AP site-binding moiety and the detection tool. ARP binds to AP sites but relies on two additional reagents, HRP-streptavidin and a substrate solution, for detection. Further, in the ARP assay, ten steps that require transfer or dilution of the DNA, which introduce error in the final DNA concentration, follow DNA concentration adjustment to 100 μg/mL. In the assay with Cy7MX, DNA concentration can be adjusted just before analysis to minimize error. The ARP assay takes at least two days to complete but must be analyzed within one hour of addition of the final substrate solution. Conversely, the assay with Cy7MX takes approximately 3 hours and samples are stable for at least two days when stored in the dark (we did not examine stability longer than two days). Therefore, we believe that compound Cy7MX is an attractive alternative to ARP for AP site quantification.

FUDR and DLD1 KD cells were able to elucidate the accumulated effect of a DNA damaging drug over time. However, UDG KD cell lines are not expected in nature. Measurement of the accumulated effect of a drug may not be possible for all purposes. Thus, the ability of Cy7MX to measure AP sites at a single time point was explored.

Methyl methanesulfonate (MMS) is a methylating agent used to induce AP sites in cells. An MMS dose-response in DLD1 WT cells was performed for a 3 h treatment time. The WT cell line has normal BER and is expected to actively undergo repair in response to the drug. Following drug treatment, DNA was extracted by phenol-chloroform and incubated with Cy7MX for 1 h. Fluorescence was measured following ethanol precipitation purification.

The data indicate that Cy7MX was sensitive to the quantity of AP sites induced by mM concentrations of MMS (FIG. 15). These results suggest that Cy7MX can detect physiological concentrations of AP sites at a single time point.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of detecting abasic (AP) sites in DNA from a biological sample, the method comprising: isolating a sample of DNA from the biological sample; contacting the DNA with a fluorescent probe; and detecting fluorescent probe labeled AP sites in the DNA sample, wherein the fluorescent probe has the following formula:

F-L-X where F is a cyanine fluorophore selected from the group consisting of Cy5, Cy5.5, Cy7, Cy7.5, ZW800-1, and CW-800, X is an aminooxy group (—ONH$_2$), and L is a linker that links or couples the fluorescent moiety to the aminooxy group.

2. The method of claim 1, the DNA being extracted from a subject's cells before the contacting step.

3. The method of claim 1, further comprising the step of correlating the number of AP sites in the sample of DNA to the number of AP sites in a control DNA specimen.

4. The method of claim 1, the control DNA specimen comprising an AP-DNA standard having a known concentrations of AP sites.

5. The method of claim 1, the AP sites of the sample DNA and the control DNA specimen being determined substantially simultaneously.

6. The method of claim 1, further comprising removing unbound fluorescent probe from the sample of DNA after contacting the DNA with the fluorescent probe.

7. A method of detecting abasic (AP) sites in DNA from a biological sample, the method comprising: isolating a sample of DNA from the biological sample; contacting the DNA with a fluorescent probe; and detecting fluorescent probe labeled AP sites in the DNA sample, wherein the fluorescent probe is selected from the group consisting of:

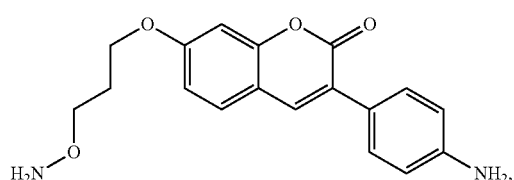

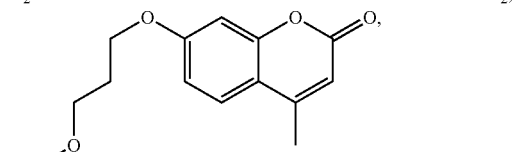

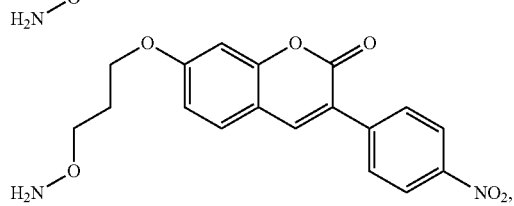

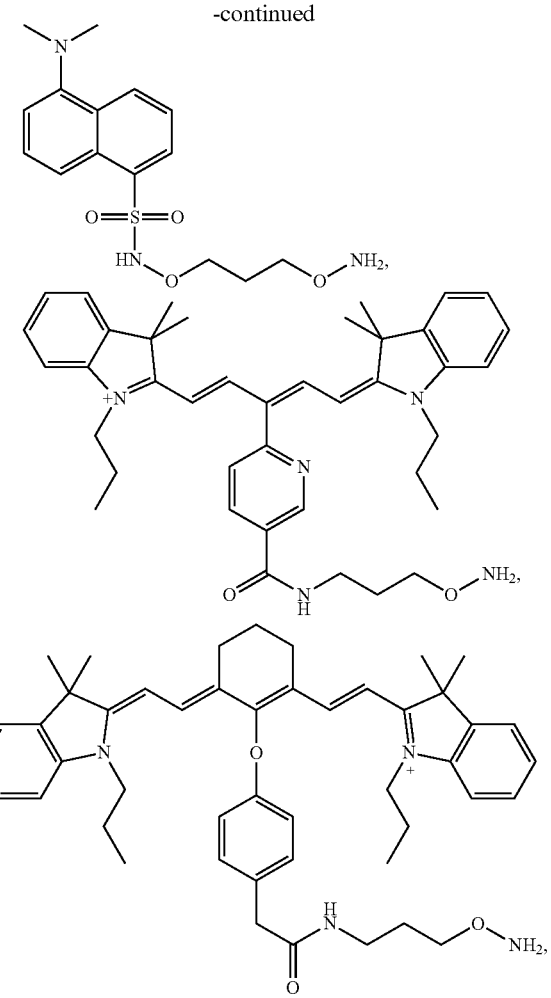

and pharmaceutically acceptable salts thereof.

8. The method of claim 7, the DNA being extracted from a subject's cells before the contacting step.

9. The method of claim 7, further comprising the step of correlating the number of AP sites in the sample of DNA to the number of AP sites in a control DNA specimen.

10. The method of claim 7, the control DNA specimen comprising an AP-DNA standard having a known concentrations of AP sites.

11. The method of claim 7, the AP sites of the sample DNA and the control DNA specimen being determined substantially simultaneously.

12. The method of claim 7, further comprising removing unbound fluorescent probe from the sample of DNA after contacting the DNA with the fluorescent probe.

* * * * *

SEQUENCE LISTING

```
<160> NUMBER OF SEQ ID NOS: 2

<210> SEQ ID NO 1
<211> LENGTH: 40
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (17)..(17)
<223> OTHER INFORMATION: Xaa can be any naturally occurring amino acid

<400> SEQUENCE: 1
tcctgggtga caaagcuaaa cactgtctcc aaaaaaaatt                          40

<210> SEQ ID NO 2
<211> LENGTH: 40
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<223> OTHER INFORMATION: Y= A, C, G, or T
<220> FEATURE:
<221> NAME/KEY: misc_feature
```

```
<222> LOCATION: (17)..(17)
<223> OTHER INFORMATION: Y= A, C, G, or T

<400> SEQUENCE: 2
aggacccact gtttcgyttt gtgacagagg ttttttttaa          40
```